(12) United States Patent
Ohrn et al.

(10) Patent No.: US 10,002,231 B2
(45) Date of Patent: Jun. 19, 2018

(54) SIMPLIFYING RESIDUE RELATIONSHIPS IN PROTEIN DESIGN

(75) Inventors: Anders Ohrn, Vancouver (CA); Gregory Lakatos, Vancouver (CA)

(73) Assignee: ZYMEWORKS INC., Vancouver (CA)

( * ) Notice: Subject to any disclaimer, the term of this patent is extended or adjusted under 35 U.S.C. 154(b) by 752 days.

(21) Appl. No.: 13/822,231

(22) PCT Filed: Sep. 29, 2011

(86) PCT No.: PCT/CA2011/001103
§ 371 (c)(1),
(2), (4) Date: Jun. 3, 2013

(87) PCT Pub. No.: WO2012/040833
PCT Pub. Date: Apr. 5, 2012

(65) Prior Publication Data
US 2013/0245963 A1    Sep. 19, 2013

Related U.S. Application Data

(60) Provisional application No. 61/388,208, filed on Sep. 30, 2010.

(51) Int. Cl.
*G06F 19/16* (2011.01)
*G06F 19/24* (2011.01)
*C07K 1/00* (2006.01)

(52) U.S. Cl.
CPC ............... *G06F 19/24* (2013.01); *C07K 1/00* (2013.01); *G06F 19/16* (2013.01)

(58) Field of Classification Search
None
See application file for complete search history.

(56) References Cited

U.S. PATENT DOCUMENTS

2013/0245963 A1    9/2013  Ohrn et al.

FOREIGN PATENT DOCUMENTS

WO    WO 2012/040833 A1    4/2012

OTHER PUBLICATIONS

Zheng et al . Protein Science, 1993,2, p. 1242-1248.*
Ming et al. BMC Structural Biology, 2008,8(5),1-11.*
Seeliger et al. PLoS Comput. Biol 6(1): 1-9.*
Lippow, S. and Tidor, B., "Progress in computational protein design" *Current Opinion in Biotechnology*, vol. 18, pp. 1-7 (2007).
Lovell, S. et al., "The Penultimate Rotamer Library" *Proteins*, vol. 40, pp. 389-408 (2000).
Pokala, N. and Handel, T., "Energy Functions for Protein Design": Adjustment with Protein-Protein Complex Affinities, Models for the Unfolded State, and Negative Design of Solubility and Specificity *J. Mol. Biol.*, vol. 347, pp. 203-227 (2005).
Ponder, J. and Case, D., "Force Fields for Protein Simulations" *Advances in Protein Chemistry*, vol. 66, pp. 27-85 (2003).
Shannon, C.E., "A Mathematical Theory of Communication" *The Bell System Technical Journal*, vol. 27, pp. 379-423, 623-656 (1948).
Sondermann, P. et al., "The 3.2-Å crystal structure of the human IgG1 Fc fragment-FcγRIII complex" *Nature*, vol. 406, pp. 267-273 (2000).
Tuncbag, N. et al., "Analysis and network representation of hotspots in protein interfaces using minimum cut trees" *Proteins*, vol. 78, pp. 2283-2294 (2010).
Seeliger and de Groot, "Conformational Transitions upon Ligand Binding: Holo-Structure Prediction from Apo Conformations", *PLOS Computational Biology*, vol. 6, Issue 1 (2010).
Stella, L. et al., "Molecular Dynamics Simulations of Human Glutathione Transferase P1-1: Analysis of the Induced-Fit Mechanism by GSH Binding", *Proteins Structure, Function, and Genetics*, vol. 37, pp. 1-9 (1999).
Zheng and Brooks, "Normal-Modes-Based Prediction of Protein Conformational Changes Guided by Distance Constraints", Biophysical Journal, vol. 88, pp. 3109-3117 (2005).

* cited by examiner

*Primary Examiner* — Michael Borin
(74) *Attorney, Agent, or Firm* — Morgan, Lewis & Bockius LLP; Brett Lovejoy

(57) ABSTRACT

The invention provides a method of determining changes in a first set of residues $r_1$ due to changes in a second set of residues $r_2$ in a protein system comprising one or more proteins comprising $r_1$ and $r_2$. In exemplary embodiments, the method comprises optimizing a quality function Q by modifying one or more properties of $r_1$ and $r_2$ in a constrained environment in which all degrees of freedom of the system except those directly involved in the potential coupling between $r_1$ and $r_2$ are removed.

15 Claims, 36 Drawing Sheets

FIGURE 3A

| | ARG | ASN | ASP | CYS | GLN | GLU | HID | HIE | HIP | ILE | LEU | LYS | MET | PHE | SER | THR | TRP | TYR | VAL |
|---|---|---|---|---|---|---|---|---|---|---|---|---|---|---|---|---|---|---|---|
| ARG | 0.053, 0.026, 0.026 | 0.158, 0.079, 0.132 | 0.211, 0.237, 0.184 | 0.237, 0.158, 0.184 | 0.105, 0.184, 0.105 | 0.132, 0.132, 0.184 | 0.237, 0.105, 0.132 | 0.395, 0.105, 0.105 | 0.184, 0.132, 0.184 | 0.211, 0.184, 0.184 | 0.184, 0.079, 0.105 | 0.132, 0.000, 0.053 | 0.158, 0.079, 0.079 | 0.211, 0.158, 0.158 | 0.132, 0.132, 0.158 | 0.237, 0.158, 0.158 | 0.263, 0.105, 0.079 | 0.289, 0.158, 0.184 | 0.237, 0.132, 0.132 |
| ASN | | 0.237, 0.158, 0.105 | 0.289, 0.079, 0.132 | 0.289, 0.237, 0.158 | 0.289, 0.158, 0.079 | 0.079, 0.079, 0.053 | 0.342, 0.158, 0.132 | 0.474, 0.132, 0.132 | 0.263, 0.105, 0.132 | 0.289, 0.263, 0.158 | 0.342, 0.289, 0.211 | 0.342, 0.053, 0.053 | 0.395, 0.105, 0.079 | 0.289, 0.395, 0.342 | 0.263, 0.211, 0.158 | 0.342, 0.263, 0.211 | 0.368, 0.211, 0.184 | 0.316, 0.289, 0.237 | 0.368, 0.316, 0.211 |
| ASP | | | 0.237, 0.053, 0.053 | 0.526, 0.158, 0.237 | 0.289, 0.079, 0.079 | 0.263, 0.053, 0.105 | 0.579, 0.132, 0.158 | 0.526, 0.105, 0.158 | 0.368, 0.158, 0.184 | 0.500, 0.237, 0.263 | 0.553, 0.132, 0.158 | 0.263, 0.053, 0.079 | 0.447, 0.079, 0.132 | 0.447, 0.316, 0.368 | 0.395, 0.211, 0.237 | 0.526, 0.289, 0.342 | 0.526, 0.132, 0.132 | 0.474, 0.316, 0.342 | 0.658, 0.184, 0.289 |
| CYS | | | | 0.579, 0.316, 0.184 | 0.316, 0.289, 0.237 | 0.289, 0.158, 0.184 | 0.553, 0.368, 0.289 | 0.711, 0.368, 0.342 | 0.500, 0.342, 0.263 | 0.395, 0.579, 0.474 | 0.684, 0.368, 0.316 | 0.316, 0.053, 0.000 | 0.342, 0.132, 0.158 | 0.605, 0.526, 0.447 | 0.368, 0.342, 0.263 | 0.526, 0.421, 0.342 | 0.447, 0.447, 0.395 | 0.605, 0.526, 0.447 | 0.632, 0.553, 0.421 |
| GLN | | | | | 0.263, 0.105, 0.105 | 0.211, 0.079, 0.105 | 0.263, 0.053, 0.053 | 0.342, 0.132, 0.105 | 0.342, 0.132, 0.105 | 0.263, 0.158, 0.158 | 0.342, 0.079, 0.053 | 0.211, 0.053, 0.026 | 0.237, 0.053, 0.053 | 0.316, 0.184, 0.211 | 0.263, 0.105, 0.079 | 0.342, 0.184, 0.132 | 0.421, 0.079, 0.132 | 0.316, 0.158, 0.132 | 0.342, 0.184, 0.158 |
| GLU | | | | | | 0.105, 0.000, 0.053 | 0.289, 0.026, 0.079 | 0.263, 0.132, 0.132 | 0.316, 0.158, 0.184 | 0.342, 0.132, 0.158 | 0.368, 0.079, 0.105 | 0.316, 0.053, 0.053 | 0.263, 0.079, 0.105 | 0.263, 0.158, 0.158 | 0.316, 0.079, 0.079 | 0.316, 0.105, 0.184 | 0.289, 0.105, 0.132 | 0.368, 0.132, 0.132 | 0.316, 0.132, 0.105 |
| HID | | | | | | | 0.342, 0.132, 0.132 | 0.474, 0.211, 0.237 | 0.342, 0.158, 0.132 | 0.395, 0.263, 0.263 | 0.447, 0.211, 0.237 | 0.342, 0.000, 0.053 | 0.289, 0.105, 0.132 | 0.263, 0.316, 0.316 | 0.368, 0.211, 0.184 | 0.395, 0.368, 0.395 | 0.526, 0.263, 0.263 | 0.474, 0.342, 0.342 | 0.553, 0.263, 0.289 |
| HIE | | | | | | | | 0.579, 0.184, 0.132 | 0.500, 0.184, 0.132 | 0.553, 0.263, 0.263 | 0.579, 0.211, 0.211 | 0.342, 0.000, 0.000 | 0.500, 0.105, 0.079 | 0.447, 0.342, 0.289 | 0.474, 0.211, 0.184 | 0.579, 0.289, 0.289 | 0.553, 0.316, 0.289 | 0.605, 0.263, 0.263 | 0.553, 0.395, 0.368 |
| HIP | | | | | | | | | 0.421, 0.211, 0.211 | 0.395, 0.263, 0.237 | 0.421, 0.184, 0.184 | 0.211, 0.053, 0.053 | 0.368, 0.132, 0.132 | 0.289, 0.289, 0.263 | 0.421, 0.395, 0.395 | 0.395, 0.342, 0.342 | 0.395, 0.316, 0.289 | 0.500, 0.263, 0.263 | 0.395, 0.395, 0.342 |
| ILE | | | | | | | | | | 0.500, 0.553, 0.474 | 0.526, 0.316, 0.289 | 0.474, 0.026, 0.000 | 0.474, 0.184, 0.184 | 0.395, 0.500, 0.526 | 0.500, 0.316, 0.263 | 0.526, 0.500, 0.500 | 0.553, 0.474, 0.447 | 0.526, 0.421, 0.421 | 0.553, 0.474, 0.474 |
| LEU | | | | | | | | | | | 0.526, 0.263, 0.211 | 0.368, 0.079, 0.053 | 0.395, 0.105, 0.105 | 0.368, 0.316, 0.289 | 0.395, 0.263, 0.237 | 0.474, 0.368, 0.263 | 0.526, 0.342, 0.316 | 0.553, 0.289, 0.368 | 0.474, 0.447, 0.421 |
| LYS | | | | | | | | | | | | 0.211, 0.000, 0.000 | 0.289, 0.053, 0.026 | 0.184, 0.132, 0.184 | 0.237, 0.079, 0.026 | 0.395, 0.105, 0.079 | 0.342, 0.105, 0.079 | 0.316, 0.079, 0.132 | 0.368, 0.158, 0.079 |
| MET | | | | | | | | | | | | | 0.316, 0.079, 0.105 | 0.316, 0.316, 0.316 | 0.316, 0.132, 0.132 | 0.342, 0.289, 0.237 | 0.342, 0.105, 0.079 | 0.342, 0.237, 0.237 | 0.316, 0.184, 0.158 |
| PHE | | | | | | | | | | | | | | 0.474 | 0.474, | 0.474, | 0.474, | 0.500, | 0.500, |

FIGURE 3B

| | ARG | ASN | ASP | CYS | GLN | GLU | HID | HIE | HIP | ILE | LEU | LYS | MET | PHE | SER | THR | TRP | TYR | VAL |
|---|---|---|---|---|---|---|---|---|---|---|---|---|---|---|---|---|---|---|---|
| SER | | | | | | | | | | | | | | 0.368, 0.368 | 0.316, 0.289 | 0.447, 0.395 | 0.342, 0.316 | 0.447, 0.447 | 0.500, 0.500 |
| THR | | | | | | | | | | | | | | | 0.368, 0.289, 0.132 | 0.421, 0.316, 0.211 | 0.526, 0.474, 0.421 | 0.605, 0.421, 0.368 | 0.526, 0.447, 0.368 |
| TRP | | | | | | | | | | | | | | | | 0.579, 0.421, 0.395 | 0.658, 0.474, 0.395 | 0.632, 0.579, 0.553 | 0.553, 0.526, 0.474 |
| TYR | | | | | | | | | | | | | | | | | 0.395, 0.237, 0.289 | 0.500, 0.342, 0.342 | 0.500, 0.421, 0.368 |
| VAL | | | | | | | | | | | | | | | | | | 0.474, 0.500, 0.500 | 0.447, 0.579, 0.579 |
| | | | | | | | | | | | | | | | | | | | 0.632, 0.579, 0.579 |

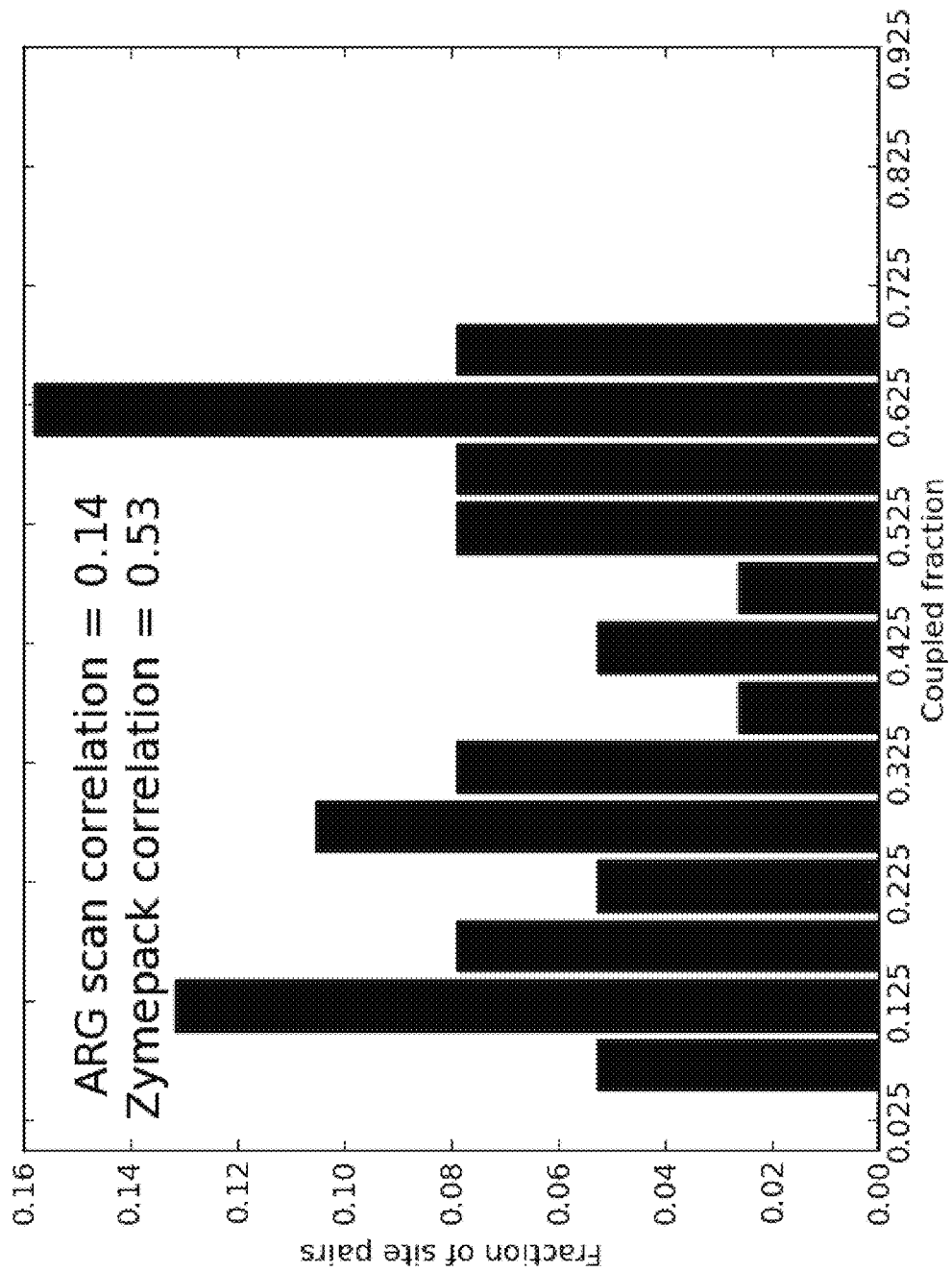

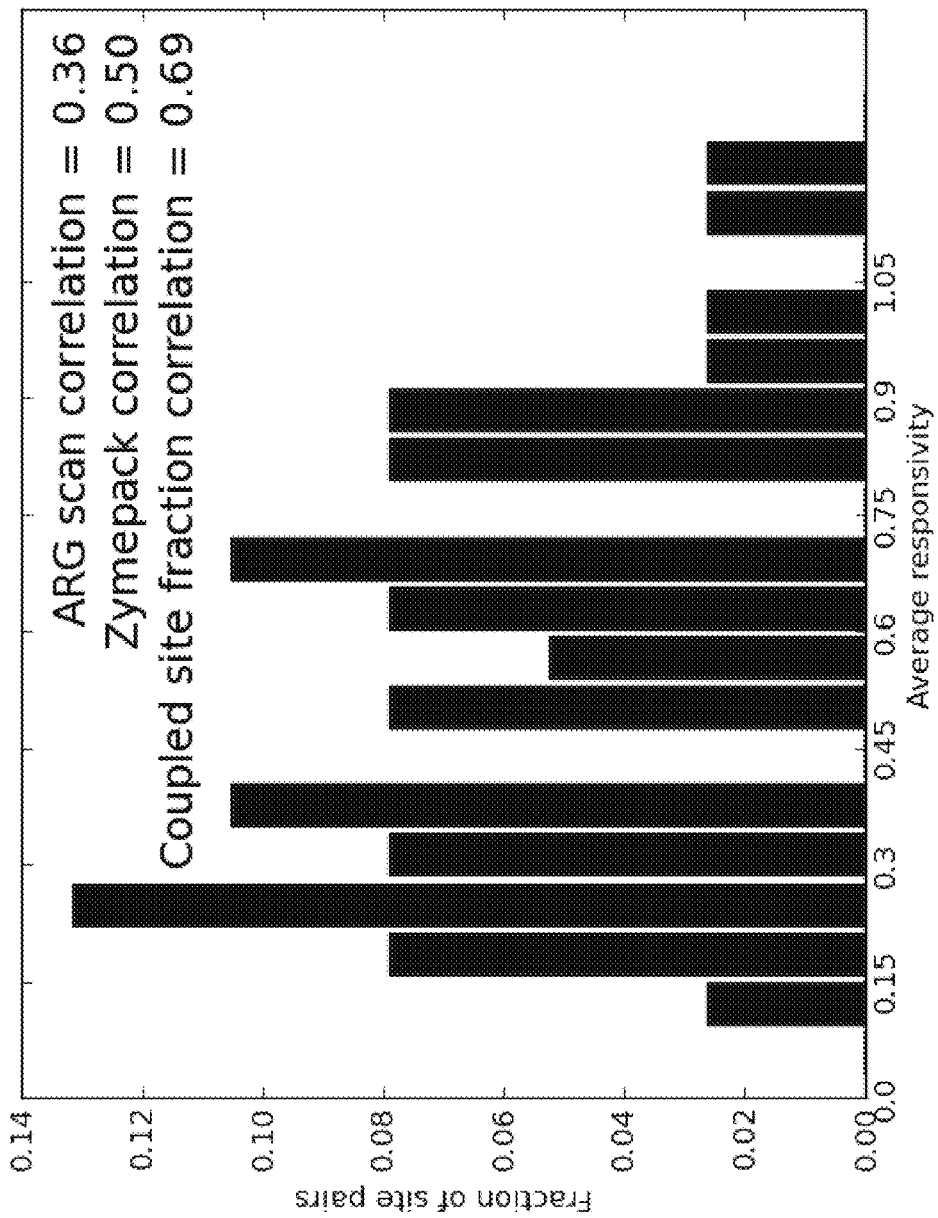

FIGURE 7A

TABLE 1: SHANNON'S ENTROPY AND CLASH COUNT FOR THE ZERO SIDE-CHAIN FRICTION LIMIT CALCULATION

| Position | Substate | A/235 | A/236 | A/237 | A/239 | A/266 | A/267 | A/325 | A/327 | A/328 | Average |
|---|---|---|---|---|---|---|---|---|---|---|---|
| A/235 | ALA | - | 0.0 (0.0) | 0.0 (0.0) | 0.0 (0.0) | 0.0 (0.0) | 0.0 (0.0) | 0.0 (0.0) | 0.0 (0.0) | 0.0 (0.0) | 0.0 (0.0) |
| | ARG | - | 0.4 (0.0) | 0.0 (0.0) | 0.0 (0.0) | 0.0 (0.0) | 0.2 (0.0) | 0.0 (0.0) | 0.2 (0.0) | 0.0 (0.0) | 0.1 (0.0) |
| | ASN | - | 0.4 (0.0) | 0.3 (0.0) | 0.3 (0.0) | 0.3 (0.0) | 0.4 (0.0) | 0.2 (0.0) | 0.5 (0.0) | 0.0 (0.0) | 0.3 (0.0) |
| | ASP | - | 0.3 (0.1) | 0.0 (0.0) | 0.0 (0.0) | 0.0 (0.0) | 0.2 (0.0) | 0.0 (0.0) | 0.3 (0.0) | 0.0 (0.0) | 0.1 (0.0) |
| | CYS | - | 0.0 (0.0) | 0.0 (0.0) | 0.0 (0.0) | 0.0 (0.0) | 0.0 (0.0) | 0.0 (0.0) | 0.0 (0.0) | 0.0 (0.0) | 0.0 (0.0) |
| | GLN | - | 0.3 (0.0) | 0.3 (0.0) | 0.2 (0.0) | 0.0 (0.0) | 0.4 (0.0) | 0.0 (0.0) | 0.4 (0.0) | 0.0 (0.0) | 0.2 (0.0) |
| | GLU | - | 0.7 (0.0) | 0.5 (0.0) | 0.7 (0.0) | 0.6 (0.0) | 0.7 (0.0) | 0.7 (0.0) | 0.6 (0.0) | 0.6 (0.0) | 0.6 (0.0) |
| | GLY | - | 0.0 (0.0) | 0.0 (0.0) | 0.0 (0.0) | 0.0 (0.0) | 0.0 (0.0) | 0.0 (0.0) | 0.0 (0.0) | 0.0 (0.0) | 0.0 (0.0) |
| | HID | - | 0.0 (0.0) | 0.0 (0.0) | 0.0 (0.0) | 0.0 (0.0) | 0.0 (0.0) | 0.0 (0.0) | 0.0 (0.0) | 0.0 (0.0) | 0.0 (0.0) |
| | HIE | - | 0.0 (0.0) | 0.0 (0.0) | 0.0 (0.0) | 0.0 (0.0) | 0.4 (0.0) | 0.0 (0.0) | 0.4 (0.0) | 0.0 (0.0) | 0.1 (0.0) |
| | HIP | - | 0.0 (0.0) | 0.0 (0.0) | 0.0 (0.0) | 0.0 (0.0) | 0.0 (0.0) | 0.0 (0.0) | 0.0 (0.0) | 0.0 (0.0) | 0.0 (0.0) |
| | ILE | - | 0.2 (0.0) | 0.0 (0.0) | 0.0 (0.0) | 0.0 (0.0) | 0.0 (0.0) | 0.0 (0.0) | 0.0 (0.0) | 0.0 (0.0) | 0.0 (0.0) |
| | LEU | - | 0.0 (0.0) | 0.0 (0.0) | 0.0 (0.0) | 0.0 (0.0) | 0.0 (0.0) | 0.0 (0.0) | 0.0 (0.0) | 0.0 (0.0) | 0.0 (0.0) |
| | LYS | - | 0.4 (0.0) | 0.3 (0.0) | 0.3 (0.0) | 0.2 (0.0) | 0.0 (0.0) | 0.2 (0.0) | 0.2 (0.0) | 0.0 (0.0) | 0.1 (0.0) |
| | MET | - | 0.5 (0.0) | 0.0 (0.0) | 0.0 (0.0) | 0.0 (0.0) | 0.0 (0.0) | 0.0 (0.0) | 0.0 (0.0) | 0.3 (0.0) | 0.3 (0.0) |
| | PHE | - | 0.0 (0.0) | 0.0 (0.0) | 0.0 (0.0) | 0.0 (0.0) | 0.0 (0.0) | 0.0 (0.0) | 0.0 (0.0) | 0.0 (0.0) | 0.0 (0.0) |
| | SER | - | 0.0 (0.0) | 0.0 (0.0) | 0.0 (0.0) | 0.0 (0.0) | 0.3 (0.0) | 0.0 (0.0) | 0.3 (0.0) | 0.0 (0.0) | 0.1 (0.0) |
| | THR | - | 0.2 (0.0) | 0.0 (0.0) | 0.0 (0.0) | 0.0 (0.0) | 0.0 (0.0) | 0.0 (0.0) | 0.0 (0.0) | 0.0 (0.0) | 0.0 (0.0) |
| | TRP | - | 0.0 (0.0) | 0.0 (0.0) | 0.0 (0.0) | 0.0 (0.0) | 0.0 (0.0) | 0.0 (0.0) | 0.0 (0.0) | 0.0 (0.0) | 0.0 (0.0) |
| | TYR | - | 0.4 (0.0) | 0.2 (0.0) | 0.0 (0.0) | 0.4 (0.0) | 0.4 (0.0) | 0.4 (0.0) | 0.4 (0.0) | 0.4 (0.0) | 0.3 (0.0) |
| | VAL | - | 0.2 (0.0) | 0.0 (0.0) | 0.2 (0.0) | 0.0 (0.0) | 0.0 (0.0) | 0.0 (0.0) | 0.0 (0.0) | 0.0 (0.0) | 0.0 (0.0) |
| | | - | 0.2 (0.0) | 0.1 (0.0) | 0.1 (0.0) | 0.1 (0.0) | 0.1 (0.0) | 0.1 (0.0) | 0.2 (0.0) | 0.1 (0.0) | |
| A/236 | ALA | 0.0 (0.0) | - | 0.0 (0.0) | 0.0 (0.0) | 0.0 (0.0) | 0.0 (0.0) | 0.0 (0.0) | 0.0 (0.0) | 0.0 (0.0) | 0.0 (0.0) |
| | ARG | 0.2 (0.0) | - | 0.4 (0.0) | 1.0 (0.0) | 0.0 (0.0) | 0.0 (0.0) | 0.4 (0.0) | 0.0 (0.0) | 0.4 (0.0) | 0.3 (0.0) |
| | ASN | 0.0 (0.0) | - | 0.0 (0.0) | 0.0 (0.0) | 0.0 (0.0) | 0.2 (0.0) | 0.0 (0.0) | 0.2 (0.0) | 0.0 (0.0) | 0.0 (0.0) |
| | ASP | 0.0 (0.0) | - | 0.0 (0.0) | 0.2 (0.0) | 0.0 (0.0) | 0.0 (0.0) | 0.0 (0.0) | 0.0 (0.0) | 0.0 (0.0) | 0.0 (0.0) |
| | CYS | 0.0 (0.0) | - | 0.0 (0.0) | 0.0 (0.0) | 0.0 (0.0) | 0.0 (0.0) | 0.0 (0.0) | 0.0 (0.0) | 0.0 (0.0) | 0.0 (0.0) |

FIGURE 7B

| Position | Substrate | A/235 | A/236 | A/237 | A/239 | A/266 | A/267 | A/325 | A/327 | A/328 | Average |
|---|---|---|---|---|---|---|---|---|---|---|---|
| | GLN | 0.0 (0.0) | - | 0.3 (0.0) | 0.4 (0.0) | 0.0 (0.0) | 0.0 (0.0) | 0.0 (0.0) | 0.0 (0.0) | 0.0 (0.0) | 0.1 (0.0) |
| | GLU | 0.4 (0.0) | - | 0.5 (0.0) | 1.1 (0.0) | 0.0 (0.0) | 0.4 (0.0) | 0.0 (0.0) | 0.4 (0.0) | 0.3 (0.0) | 0.4 (0.0) |
| | GLY | 0.0 (0.0) | - | 0.0 (0.0) | 0.0 (0.0) | 0.0 (0.0) | 0.0 (0.0) | 0.0 (0.0) | 0.0 (0.0) | 0.0 (0.0) | 0.0 (0.0) |
| | HID | 0.0 (0.0) | - | 0.0 (0.0) | 0.0 (0.0) | 0.0 (0.0) | 0.0 (0.0) | 0.0 (0.0) | 0.0 (0.0) | 0.0 (0.0) | 0.0 (0.0) |
| | HIE | 0.0 (0.0) | - | 0.0 (0.0) | 0.0 (0.0) | 0.0 (0.0) | 0.0 (0.0) | 0.0 (0.0) | 0.0 (0.0) | 0.0 (0.0) | 0.0 (0.0) |
| | HIP | 0.0 (0.0) | - | 0.0 (0.0) | 0.0 (0.0) | 0.0 (0.0) | 0.0 (0.0) | 0.0 (0.0) | 0.0 (0.0) | 0.0 (0.0) | 0.0 (0.0) |
| | ILE | 0.0 (3.0) | - | 0.0 (3.0) | 0.0 (3.0) | 0.0 (3.0) | 0.0 (3.0) | 0.0 (3.0) | 0.0 (3.0) | 0.0 (3.0) | 0.0 (3.0) |
| | LEU | 0.0 (0.0) | - | 0.0 (0.0) | 0.0 (0.0) | 0.0 (0.0) | 0.0 (0.0) | 0.0 (0.0) | 0.0 (0.0) | 0.0 (0.0) | 0.0 (0.0) |
| | LYS | 0.2 (0.0) | - | 0.4 (0.0) | 1.2 (0.0) | 0.4 (0.0) | 0.7 (0.0) | 0.4 (0.0) | 0.4 (0.0) | 0.4 (0.0) | 0.5 (0.0) |
| | MET | 0.0 (0.0) | - | 0.2 (0.0) | 0.2 (0.0) | 0.0 (0.0) | 0.0 (0.0) | 0.0 (0.0) | 0.0 (0.0) | 0.0 (0.0) | 0.0 (0.0) |
| | PHE | 0.0 (0.0) | - | 0.0 (0.0) | 0.0 (0.0) | 0.0 (0.0) | 0.0 (0.0) | 0.0 (0.0) | 0.0 (0.0) | 0.0 (0.0) | 0.0 (0.0) |
| | SER | 0.0 (0.0) | - | 0.0 (0.0) | 0.0 (0.0) | 0.0 (0.0) | 0.0 (0.0) | 0.0 (0.0) | 0.0 (0.0) | 0.0 (0.0) | 0.0 (0.0) |
| | THR | 0.0 (0.0) | - | 0.6 (0.0) | 0.7 (0.0) | 0.0 (0.0) | 0.4 (0.0) | 0.4 (0.0) | 0.4 (0.0) | 0.4 (0.0) | 0.4 (0.0) |
| | TRP | 0.0 (0.0) | - | 0.0 (0.0) | 0.0 (0.0) | 0.0 (0.0) | 0.0 (0.0) | 0.0 (0.0) | 0.0 (0.0) | 0.0 (0.0) | 0.0 (0.0) |
| | TYR | 0.2 (1.0) | - | 1.2 (1.4) | 0.7 (1.0) | 0.2 (1.0) | 0.3 (1.0) | 0.2 (1.0) | 0.3 (1.0) | 0.3 (1.0) | 0.4 (1.0) |
| | VAL | 0.0 (0.0) | - | 0.0 (0.0) | 0.0 (0.0) | 0.0 (0.0) | 0.0 (0.0) | 0.0 (0.0) | 0.0 (0.0) | 0.0 (0.0) | 0.0 (0.0) |
| A/237 | | 0.0 (0.2) | - | 0.2 (0.2) | 0.3 (0.2) | 0.0 (0.2) | 0.1 (0.2) | 0.0 (0.2) | 0.1 (0.2) | 0.1 (0.2) | | 
| | ALA | 0.0 (0.0) | 0.0 (0.0) | - | 0.0 (0.0) | 0.0 (0.0) | 0.0 (0.0) | 0.0 (0.0) | 0.0 (0.0) | 0.0 (0.2) | 0.0 (0.0) |
| | ARG | 0.0 (0.0) | 0.9 (0.0) | - | 0.9 (0.0) | 0.3 (0.0) | 0.0 (0.0) | 0.7 (0.0) | 0.2 (0.0) | 1.6 (0.2) | 0.6 (0.0) |
| | ASN | 0.0 (0.0) | 0.4 (0.0) | - | 0.0 (0.0) | 0.0 (0.0) | 0.0 (0.0) | 0.3 (0.0) | 0.0 (0.0) | 1.2 (0.5) | 0.2 (0.1) |
| | ASP | 0.0 (0.0) | 0.2 (0.0) | - | 0.2 (0.0) | 0.0 (0.0) | 0.0 (0.0) | 0.0 (0.0) | 0.0 (0.0) | 0.7 (0.5) | 0.1 (0.1) |
| | CYS | 0.0 (0.0) | 0.2 (0.0) | - | 0.0 (0.0) | 0.0 (0.0) | 0.0 (0.0) | 0.0 (0.0) | 0.0 (0.0) | 0.5 (0.3) | 0.1 (0.0) |
| | GLN | 0.4 (0.0) | 0.7 (0.0) | - | 0.6 (0.0) | 0.0 (0.0) | 0.4 (0.0) | 0.4 (0.0) | 0.0 (0.0) | 1.3 (0.2) | 0.3 (0.0) |
| | GLU | 0.0 (0.0) | 0.0 (0.0) | - | 0.4 (0.0) | 0.0 (0.0) | 0.0 (0.0) | 0.9 (0.0) | 0.5 (0.0) | 1.7 (0.3) | 0.6 (0.0) |
| | GLY | 0.0 (0.0) | 0.2 (0.1) | - | 0.0 (0.0) | 0.0 (0.0) | 0.0 (0.0) | 0.0 (0.0) | 0.0 (0.0) | 0.0 (0.0) | 0.0 (0.0) |
| | HID | 0.0 (0.0) | 0.2 (0.1) | - | 0.0 (0.0) | 0.0 (0.0) | 0.4 (0.0) | 0.2 (0.0) | 0.0 (0.0) | 0.6 (0.2) | 0.1 (0.0) |
| | HIE | 0.0 (0.0) | 0.0 (0.0) | - | 0.0 (0.0) | 0.0 (0.0) | 0.0 (0.0) | 0.0 (0.0) | 0.0 (0.0) | 0.8 (0.2) | 0.1 (0.0) |
| | HIP | 0.0 (0.0) | 0.2 (0.0) | - | 0.2 (0.0) | 0.0 (0.0) | 0.0 (0.0) | 0.0 (0.0) | 0.0 (0.0) | 0.6 (0.2) | 0.1 (0.0) |
| | ILE | 0.0 (0.0) | 0.0 (0.0) | - | 0.0 (0.0) | 0.0 (0.0) | 0.0 (0.0) | 0.2 (0.0) | 0.0 (0.0) | 0.8 (0.2) | 0.1 (0.0) |
| | LEU | 0.0 (0.0) | 0.3 (0.0) | - | 0.0 (0.0) | 0.0 (0.0) | 0.0 (0.0) | 0.3 (0.0) | 0.0 (0.0) | 0.0 (0.5) | 0.1 (0.1) |

FIGURE 7C

| Position | Substate | A/235 | A/236 | A/237 | A/239 | A/266 | A/267 | A/325 | A/327 | A/328 | Average |
|---|---|---|---|---|---|---|---|---|---|---|---|
| | LYS | 0.0 (0.0) | 0.4 (0.0) | - | 0.8 (0.0) | 0.2 (0.0) | 0.0 (0.0) | 0.8 (0.0) | 0.0 (0.0) | 1.7 (0.2) | 0.5 (0.0) |
| | MET | 0.0 (0.0) | 0.4 (0.0) | - | 0.4 (0.0) | 0.0 (0.0) | 0.0 (0.0) | 0.0 (0.0) | 0.0 (0.0) | 1.6 (0.3) | 0.3 (0.0) |
| | PHE | 0.0 (0.0) | 0.0 (0.0) | - | 0.0 (0.0) | 0.0 (0.0) | 0.0 (0.0) | 0.0 (0.0) | 0.0 (0.0) | 0.2 (0.2) | 0.0 (0.0) |
| | SER | 0.4 (0.0) | 0.8 (0.0) | - | 0.7 (0.0) | 0.3 (0.0) | 0.8 (0.0) | 1.2 (0.0) | 0.8 (0.0) | 1.5 (0.3) | 0.8 (0.0) |
| | THR | 0.0 (0.0) | 0.4 (0.0) | - | 0.5 (0.0) | 0.0 (0.0) | 0.0 (0.0) | 0.5 (0.0) | 0.2 (0.0) | 1.0 (0.4) | 0.3 (0.0) |
| | TRP | 0.0 (0.0) | 0.0 (0.0) | - | 0.0 (0.0) | 0.0 (0.0) | 0.0 (0.0) | 0.0 (0.0) | 0.0 (0.0) | 0.0 (0.2) | 0.0 (0.0) |
| | TYR | 0.3 (0.0) | 0.5 (0.0) | - | 0.5 (0.0) | 0.0 (0.0) | 0.0 (0.0) | 0.3 (0.0) | 0.0 (0.0) | 0.4 (0.3) | 0.3 (0.0) |
| | VAL | 0.0 (0.0) | 0.2 (0.0) | - | 0.0 (0.0) | 0.0 (0.0) | 0.0 (0.0) | 0.5 (0.0) | 0.0 (0.0) | 0.7 (0.2) | 0.2 (0.0) |
| A/239 | | 0.1 (0.0) | 0.3 (0.0) | - | 0.2 (0.0) | 0.0 (0.0) | 0.1 (0.0) | 0.3 (0.0) | 0.1 (0.0) | 0.8 (0.3) | |
| | ALA | 0.0 (0.0) | 0.0 (0.0) | 0.0 (0.0) | - | 0.0 (0.0) | 0.0 (0.0) | 0.0 (0.0) | 0.0 (0.0) | 0.0 (0.0) | 0.0 (0.0) |
| | ARG | 0.0 (0.0) | 0.8 (0.0) | 1.5 (0.0) | - | 0.0 (0.0) | 0.0 (0.0) | 0.4 (0.0) | 0.0 (0.0) | 0.4 (0.0) | 0.4 (0.0) |
| | ASN | 0.3 (0.0) | 0.8 (0.0) | 1.2 (0.0) | - | 0.3 (0.0) | 0.3 (0.0) | 0.6 (0.0) | 0.3 (0.0) | 0.7 (0.0) | 0.6 (0.0) |
| | ASP | 0.0 (0.0) | 0.5 (0.0) | 0.7 (0.0) | - | 0.3 (0.0) | 0.3 (0.0) | 0.2 (0.0) | 0.0 (0.0) | 0.3 (0.0) | 0.3 (0.0) |
| | CYS | 0.0 (0.0) | 0.6 (0.0) | 0.0 (0.0) | - | 0.0 (0.0) | 0.0 (0.0) | 0.0 (0.0) | 0.0 (0.0) | 0.0 (0.0) | 0.1 (0.0) |
| | GLN | 0.0 (0.0) | 0.8 (0.0) | 1.7 (0.0) | - | 0.3 (0.0) | 0.2 (0.0) | 0.4 (0.0) | 0.2 (0.0) | 0.2 (0.0) | 0.4 (0.0) |
| | GLU | 0.4 (0.0) | 1.5 (0.0) | 0.9 (0.0) | - | 0.3 (0.0) | 0.3 (0.0) | 0.4 (0.0) | 0.4 (0.0) | 0.4 (0.0) | 0.6 (0.0) |
| | GLY | 0.0 (0.0) | 0.0 (0.0) | 0.0 (0.0) | - | 0.0 (0.0) | 0.0 (0.0) | 0.0 (0.0) | 0.0 (0.0) | 0.0 (0.0) | 0.0 (0.0) |
| | HID | 0.0 (0.0) | 1.0 (0.0) | 0.5 (0.0) | - | 0.2 (0.0) | 0.2 (0.0) | 0.0 (0.0) | 0.0 (0.0) | 0.0 (0.0) | 0.2 (0.0) |
| | HIE | 0.3 (0.0) | 1.0 (0.0) | 0.4 (0.0) | - | 0.0 (0.0) | 0.3 (0.0) | 0.4 (0.0) | 0.4 (0.0) | 0.3 (0.0) | 0.4 (0.0) |
| | HIP | 0.3 (0.0) | 0.5 (0.0) | 1.4 (0.0) | - | 0.2 (0.0) | 0.3 (0.0) | 0.3 (0.0) | 0.3 (0.0) | 0.7 (0.0) | 0.5 (0.0) |
| | ILE | 0.0 (0.0) | 0.5 (0.0) | 0.2 (0.0) | - | 0.0 (0.0) | 0.0 (0.0) | 0.0 (0.0) | 0.0 (0.0) | 0.0 (0.0) | 0.1 (0.0) |
| | LEU | 0.0 (0.0) | 0.5 (0.0) | 0.7 (0.0) | - | 0.0 (0.0) | 0.0 (0.0) | 0.0 (0.0) | 0.0 (0.0) | 0.3 (0.0) | 0.2 (0.0) |
| | LYS | 0.7 (0.0) | 1.2 (0.0) | 1.2 (0.0) | - | 0.2 (0.0) | 0.8 (0.0) | 0.7 (0.0) | 0.5 (0.0) | 1.1 (0.0) | 0.8 (0.0) |
| | MET | 0.0 (0.0) | 1.7 (0.0) | 0.6 (0.0) | - | 0.0 (0.0) | 0.0 (0.0) | 0.0 (0.0) | 0.0 (0.0) | 0.2 (0.0) | 0.3 (0.0) |
| | PHE | 0.0 (0.0) | 0.5 (0.0) | 0.0 (0.0) | - | 0.0 (0.0) | 0.0 (0.0) | 0.0 (0.0) | 0.0 (0.0) | 0.0 (0.0) | 0.1 (0.0) |
| | SER | 0.0 (0.0) | 0.8 (0.0) | 0.4 (0.0) | - | 0.4 (0.0) | 0.3 (0.0) | 0.0 (0.0) | 0.2 (0.0) | 0.2 (0.0) | 0.3 (0.0) |
| | THR | 0.4 (0.0) | 1.1 (0.0) | 0.5 (0.0) | - | 0.3 (0.0) | 0.3 (0.0) | 0.5 (0.0) | 0.0 (0.0) | 0.6 (0.0) | 0.5 (0.0) |
| | TRP | 0.0 (0.0) | 0.4 (0.0) | 0.5 (0.0) | - | 0.0 (0.0) | 0.0 (0.0) | 0.4 (0.0) | 0.2 (0.0) | 0.4 (0.0) | 0.2 (0.0) |
| | TYR | 0.0 (0.0) | 0.6 (0.0) | 0.0 (0.0) | - | 0.0 (0.0) | 0.0 (0.0) | 0.0 (0.0) | 0.0 (0.0) | 0.0 (0.0) | 0.1 (0.0) |
| | VAL | 0.0 (0.0) | 0.2 (0.0) | 0.0 (0.0) | - | 0.0 (0.0) | 0.0 (0.0) | 0.0 (0.0) | 0.0 (0.0) | 0.0 (0.0) | 0.0 (0.0) |

FIGURE 7D

| Position | Substrate | A/235 | A/236 | A/237 | A/239 | A/266 | A/267 | A/325 | A/327 | A/328 | Average |
|---|---|---|---|---|---|---|---|---|---|---|---|
| A/266 | ALA | 0.1 (0.0) | 0.7 (0.0) | 0.6 (0.0) | - | 0.1 (0.0) | 0.2 (0.0) | 0.2 (0.0) | 0.1 (0.0) | 0.3 (0.0) | 0.0 (0.0) |
| | ARG | 0.0 (0.0) | 0.0 (0.0) | 0.0 (0.0) | 0.0 (0.0) | | 0.0 (0.0) | 0.0 (0.0) | 0.0 (0.0) | 0.0 (0.0) | 0.0 (0.0) |
| | ASN | 0.0 (2.0) | 0.0 (2.0) | 0.0 (2.0) | 0.0 (2.0) | - | 0.0 (2.0) | 0.8 (1.5) | 0.0 (2.0) | 0.3 (1.8) | 0.1 (1.9) |
| | ASP | 0.0 (0.0) | 0.0 (0.0) | 0.0 (0.0) | 0.0 (0.0) | - | 0.2 (0.0) | 0.4 (0.0) | 0.2 (0.0) | 0.3 (0.0) | 0.1 (0.0) |
| | CYS | 0.0 (0.0) | 0.0 (0.0) | 0.0 (0.0) | 0.0 (0.0) | - | 0.0 (0.0) | 0.2 (0.0) | 0.0 (0.0) | 0.2 (0.0) | 0.0 (0.0) |
| | GLN | 0.0 (0.0) | 0.0 (0.0) | 0.0 (0.0) | 0.0 (0.0) | - | 0.0 (0.0) | 0.0 (0.0) | 0.0 (0.0) | 0.0 (0.0) | 0.0 (0.0) |
| | GLU | 0.0 (0.0) | 0.4 (0.0) | 0.4 (0.0) | 0.4 (0.0) | - | 0.5 (0.0) | 0.7 (0.0) | 0.4 (0.0) | 0.4 (0.0) | 0.4 (0.0) |
| | GLY | 0.0 (0.0) | 0.4 (0.0) | 0.4 (0.0) | 0.3 (0.0) | - | 0.4 (0.0) | 0.5 (0.0) | 0.4 (0.0) | 0.4 (0.0) | 0.4 (0.0) |
| | HID | 0.0 (0.0) | 0.0 (0.0) | 0.0 (0.0) | 0.0 (0.0) | - | 0.0 (0.0) | 0.0 (0.0) | 0.0 (0.0) | 0.0 (0.0) | 0.0 (0.0) |
| | HIE | 0.0 (1.0) | 0.0 (1.0) | 0.0 (1.0) | 0.0 (1.0) | - | 0.0 (1.0) | 0.0 (1.0) | 0.0 (1.0) | 0.0 (1.0) | 0.0 (1.0) |
| | HIP | 0.0 (1.0) | 0.0 (1.0) | 0.0 (1.0) | 0.0 (1.0) | - | 0.0 (1.0) | 0.0 (1.0) | 0.0 (1.0) | 0.0 (1.0) | 0.0 (1.0) |
| | ILE | 0.0 (0.0) | 0.0 (0.0) | 0.0 (0.0) | 0.0 (0.0) | - | 0.0 (0.0) | 0.0 (0.0) | 0.0 (0.0) | 0.0 (0.0) | 0.0 (0.0) |
| | LEU | 0.0 (0.0) | 0.0 (0.0) | 0.0 (0.0) | 0.0 (0.0) | - | 0.2 (0.0) | 0.3 (0.0) | 0.0 (0.0) | 0.0 (0.0) | 0.1 (0.0) |
| | LYS | 0.0 (0.0) | 0.0 (0.0) | 0.0 (0.0) | 0.0 (0.0) | - | 0.0 (0.0) | 0.3 (0.0) | 0.0 (0.0) | 0.0 (0.0) | 0.0 (0.0) |
| | MET | 0.0 (0.0) | 0.0 (0.0) | 0.0 (0.0) | 0.0 (0.0) | - | 0.3 (0.0) | 0.8 (0.0) | 0.0 (0.0) | 0.0 (0.0) | 0.1 (0.0) |
| | PHE | 0.0 (8.0) | 0.0 (8.0) | 0.0 (8.0) | 0.0 (8.0) | - | 0.0 (8.0) | 0.0 (8.0) | 0.0 (8.0) | 0.0 (8.0) | 0.0 (8.0) |
| | SER | 0.0 (0.0) | 0.3 (0.0) | 0.0 (0.0) | 0.0 (0.0) | - | 0.2 (0.0) | 0.3 (0.0) | 0.0 (0.0) | 0.0 (0.0) | 0.1 (0.0) |
| | THR | 0.0 (0.0) | 0.4 (0.0) | 0.0 (0.0) | 0.2 (0.0) | - | 0.0 (0.0) | 0.3 (0.0) | 0.0 (0.0) | 0.0 (0.0) | 0.1 (0.0) |
| | TRP | 0.0 (1.0) | 0.0 (1.0) | 0.0 (1.0) | 0.0 (1.0) | - | 0.0 (1.0) | 0.3 (1.6) | 0.0 (1.0) | 0.0 (1.0) | 0.0 (1.1) |
| | TYR | 0.0 (17.0) | 0.0 (17.0) | 0.0 (17.0) | 0.0 (17.0) | - | 0.0 (17.0) | 0.0 (17.0) | 0.0 (17.0) | 0.0 (17.0) | 0.0 (17.0) |
| | VAL | 0.0 (1.5) | 0.1 (1.5) | 0.0 (1.5) | 0.0 (1.5) | - | 0.1 (1.5) | 0.2 (1.5) | 0.0 (1.5) | 0.1 (1.5) | 0.0 (0.0) |
| A/267 | ALA | 0.0 (0.0) | 0.0 (0.0) | 0.0 (0.0) | 0.0 (0.0) | 0.0 (0.0) | - | 0.0 (0.0) | 0.0 (0.0) | 0.0 (0.0) | 0.0 (0.0) |
| | ARG | 0.3 (0.0) | 0.0 (0.0) | 0.0 (0.0) | 0.0 (0.0) | 0.0 (0.0) | - | 0.0 (0.0) | 1.3 (0.0) | 0.0 (0.0) | 0.2 (0.0) |
| | ASN | 0.6 (0.0) | 0.4 (0.0) | 0.3 (0.0) | 0.5 (0.0) | 0.7 (0.0) | - | 0.8 (0.0) | 1.0 (0.0) | 0.5 (0.0) | 0.6 (0.0) |
| | ASP | 0.0 (0.0) | 0.0 (0.0) | 0.0 (0.0) | 0.0 (0.0) | 0.0 (0.0) | - | 0.2 (0.0) | 0.5 (0.0) | 0.0 (0.0) | 0.1 (0.0) |
| | CYS | 0.0 (0.0) | 0.0 (0.0) | 0.0 (0.0) | 0.0 (0.0) | 0.0 (0.0) | - | 0.0 (0.0) | 0.2 (0.0) | 0.0 (0.0) | 0.0 (0.0) |
| | GLN | 0.4 (0.0) | 0.0 (0.0) | 0.0 (0.0) | 0.0 (0.0) | 0.7 (0.0) | - | 0.7 (0.0) | 0.8 (0.0) | 0.2 (0.0) | 0.4 (0.0) |
| | GLU | 0.3 (0.0) | 0.7 (0.0) | 0.4 (0.0) | 0.6 (0.0) | 0.5 (0.0) | - | 0.7 (0.0) | 0.9 (0.0) | 0.4 (0.0) | 0.6 (0.0) |

FIGURE 7E

| Position | Substrate | A/235 | A/236 | A/237 | A/239 | A/266 | A/267 | A/325 | A/327 | A/328 | Average |
|---|---|---|---|---|---|---|---|---|---|---|---|
| | GLY | 0.0 (0.0) | 0.0 (0.0) | 0.0 (0.0) | 0.0 (0.0) | 0.0 (0.0) | - | 0.0 (0.0) | 0.0 (0.0) | 0.0 (0.0) | 0.0 (0.0) |
| | HID | 0.0 (0.0) | 0.4 (0.0) | 0.4 (0.0) | 0.3 (0.0) | 0.4 (0.0) | - | 0.5 (0.0) | 0.9 (1.0) | 0.4 (0.0) | 0.4 (0.1) |
| | HIE | 0.0 (0.0) | 0.0 (0.0) | 0.0 (0.0) | 0.0 (0.0) | 0.3 (0.0) | - | 0.0 (0.0) | 0.9 (1.3) | 0.0 (0.0) | 0.2 (0.2) |
| | HIP | 0.0 (0.0) | 0.0 (0.0) | 0.0 (0.0) | 0.0 (0.0) | 0.0 (0.0) | - | 0.0 (0.0) | 0.9 (1.2) | 0.0 (0.0) | 0.1 (0.1) |
| | ILE | 0.0 (0.0) | 0.0 (0.0) | 0.0 (0.0) | 0.0 (0.0) | 0.3 (0.0) | - | 0.0 (0.0) | 0.2 (0.0) | 0.0 (0.0) | 0.1 (0.0) |
| | LEU | 0.0 (0.0) | 0.0 (0.0) | 0.0 (0.0) | 0.0 (0.0) | 0.0 (0.0) | - | 0.0 (0.0) | 0.7 (0.0) | 0.0 (0.0) | 0.1 (0.0) |
| | LYS | 0.0 (0.0) | 0.5 (0.1) | 0.0 (0.0) | 0.0 (0.0) | 0.0 (0.0) | - | 0.2 (0.0) | 1.6 (0.3) | 0.0 (0.0) | 0.3 (0.0) |
| | MET | 0.0 (0.0) | 0.0 (0.0) | 0.0 (0.0) | 0.0 (0.0) | 0.0 (0.0) | - | 0.0 (0.0) | 0.7 (0.0) | 0.0 (0.0) | 0.1 (0.0) |
| | PHE | 0.0 (0.0) | 0.0 (0.0) | 0.0 (0.0) | 0.0 (0.0) | 0.0 (0.0) | - | 0.0 (0.0) | 0.6 (2.3) | 0.0 (0.0) | 0.1 (0.3) |
| | SER | 0.0 (0.0) | 0.0 (0.0) | 0.0 (0.0) | 0.0 (0.0) | 0.2 (0.0) | - | 0.0 (0.0) | 0.4 (0.0) | 0.0 (0.0) | 0.1 (0.0) |
| | THR | 0.0 (0.0) | 0.2 (0.0) | 0.0 (0.0) | 0.0 (0.0) | 0.5 (0.0) | - | 0.5 (0.0) | 0.5 (0.0) | 0.3 (0.0) | 0.3 (0.0) |
| | TRP | 0.0 (0.0) | 0.0 (0.0) | 0.0 (0.0) | 0.0 (0.0) | 0.0 (0.0) | - | 0.0 (0.0) | 1.0 (1.9) | 0.0 (0.0) | 0.1 (0.2) |
| | TYR | 0.0 (2.0) | 0.0 (2.0) | 0.3 (2.0) | 0.0 (2.0) | 0.0 (2.0) | - | 0.3 (2.0) | 0.7 (3.0) | 0.2 (2.0) | 0.2 (2.1) |
| | VAL | 0.0 (0.0) | 0.0 (0.0) | 0.0 (0.0) | 0.0 (0.0) | 0.0 (0.0) | - | 0.2 (0.0) | 0.0 (0.0) | 0.0 (0.0) | 0.0 (0.0) |
| A/325 | ALA | 0.1 (0.1) | 0.1 (0.1) | 0.1 (0.1) | 0.1 (0.1) | 0.2 (0.1) | 0.0 (0.0) | 0.2 (0.1) | 0.7 (0.5) | 0.1 (0.1) | 0.0 (0.0) |
| | ARG | 0.0 (0.0) | 0.0 (0.0) | 0.0 (0.0) | 0.0 (0.0) | 0.0 (0.0) | 0.0 (0.0) | - | 0.0 (0.0) | 0.0 (0.0) | 0.0 (0.0) |
| | ASN | 0.0 (0.0) | 0.0 (0.0) | 0.2 (0.0) | 0.0 (0.0) | 0.2 (0.0) | 0.0 (0.0) | - | 0.0 (0.0) | 1.0 (0.2) | 0.2 (0.0) |
| | ASP | 0.0 (0.0) | 0.3 (0.0) | 0.3 (0.0) | 0.3 (0.0) | 0.7 (0.0) | 0.4 (0.0) | - | 0.4 (0.0) | 0.4 (0.0) | 0.4 (0.0) |
| | CYS | 0.0 (0.0) | 0.0 (0.0) | 0.4 (0.0) | 0.2 (0.0) | 1.0 (0.0) | 0.0 (0.0) | - | 0.2 (0.0) | 0.0 (0.0) | 0.2 (0.0) |
| | GLN | 0.0 (0.0) | 0.0 (0.0) | 0.0 (0.0) | 0.0 (0.0) | 0.3 (0.0) | 0.0 (0.0) | - | 0.0 (0.0) | 0.5 (0.0) | 0.1 (0.0) |
| | GLU | 0.4 (0.0) | 0.4 (0.0) | 0.7 (0.0) | 0.6 (0.0) | 0.6 (0.0) | 0.5 (0.0) | - | 0.7 (0.0) | 0.8 (0.0) | 0.6 (0.0) |
| | GLY | 0.0 (0.0) | 0.0 (0.0) | 0.0 (0.0) | 0.0 (0.0) | 1.0 (0.2) | 0.0 (0.0) | - | 0.0 (0.0) | 0.0 (0.0) | 0.1 (0.0) |
| | HID | 0.0 (0.0) | 0.0 (0.0) | 0.0 (0.0) | 0.0 (0.0) | 0.0 (0.0) | 0.0 (0.0) | - | 0.0 (0.0) | 0.0 (0.0) | 0.0 (0.0) |
| | HIE | 0.0 (0.0) | 0.3 (0.0) | 0.0 (0.0) | 0.3 (0.0) | 0.0 (0.0) | 0.4 (0.0) | - | 0.0 (0.0) | 0.4 (0.3) | 0.1 (0.0) |
| | HIP | 0.0 (0.0) | 0.0 (0.0) | 0.0 (0.0) | 0.2 (0.0) | 0.0 (0.0) | 0.0 (0.0) | - | 0.2 (0.0) | 0.3 (0.2) | 0.0 (0.0) |
| | ILE | 0.0 (0.0) | 0.0 (0.0) | 0.0 (0.0) | 0.0 (0.0) | 0.0 (0.0) | 0.0 (0.0) | - | 0.0 (0.0) | 0.3 (0.2) | 0.0 (0.0) |
| | LEU | 0.0 (1.0) | 0.0 (1.0) | 0.0 (1.0) | 0.0 (1.0) | 0.5 (0.1) | 0.0 (0.0) | - | 0.0 (0.0) | 0.0 (0.0) | 0.1 (0.0) |
| | LEU | 0.0 (0.0) | 0.0 (1.0) | 0.0 (1.0) | 0.0 (1.0) | 0.2 (1.0) | 0.2 (1.0) | - | 0.2 (1.0) | 0.0 (1.0) | 0.1 (1.0) |
| | LYS | 0.0 (0.0) | 0.4 (0.0) | 0.6 (0.0) | 0.4 (0.0) | 0.8 (0.0) | 0.7 (0.0) | - | 0.6 (0.0) | 0.7 (0.0) | 0.5 (0.0) |
| | MET | 0.0 (0.0) | 0.0 (0.0) | 0.0 (0.0) | 0.0 (0.0) | 0.5 (0.0) | 0.0 (0.0) | - | 0.0 (0.0) | 0.2 (0.0) | 0.1 (0.0) |

FIGURE 7F

| Position | Substrate | A/235 | A/236 | A/237 | A/239 | A/266 | A/267 | A/325 | A/327 | A/328 | Average |
|---|---|---|---|---|---|---|---|---|---|---|---|
| | PHE | 0.0 (1.0) | 0.0 (1.0) | 0.5 (4.2) | 0.0 (1.0) | 0.0 (1.0) | 0.0 (1.0) | - | 0.0 (1.0) | 0.2 (1.3) | 0.1 (1.4) |
| | SER | 0.0 (0.0) | 0.0 (0.0) | 0.0 (0.0) | 0.0 (0.0) | 0.5 (0.0) | 0.2 (0.0) | - | 0.2 (0.0) | 0.4 (0.0) | 0.2 (0.0) |
| | THR | 0.0 (0.0) | 0.0 (0.0) | 0.0 (0.0) | 0.0 (0.0) | 0.6 (0.1) | 0.0 (0.0) | - | 0.2 (0.0) | 1.0 (0.0) | 0.2 (0.0) |
| | TRP | 0.0 (0.0) | 0.0 (0.0) | 0.0 (0.0) | 0.0 (0.0) | 0.0 (0.0) | 0.0 (0.0) | - | 0.0 (0.0) | 0.2 (0.3) | 0.0 (0.0) |
| | TYR | 0.0 (10.0) | 0.0 (10.0) | 0.0 (10.0) | 0.0 (10.0) | 0.3 (9.3) | 0.2 (9.7) | - | 0.0 (10.0) | 0.6 (7.7) | 0.1 (9.6) |
| | VAL | 0.0 (0.0) | 0.1 (0.6) | 0.1 (0.7) | 0.1 (0.6) | 0.3 (0.6) | 0.1 (0.6) | - | 0.1 (0.6) | 0.5 (0.0) | 0.1 (0.0) |
| A/327 | ALA | 0.0 (0.6) | 0.0 (0.0) | 0.0 (0.0) | 0.0 (0.0) | 0.0 (0.0) | 0.0 (0.0) | 0.0 (0.0) | | 0.4 (0.5) | |
| | ARG | 0.0 (0.0) | 0.2 (0.0) | 0.2 (0.0) | 0.0 (0.0) | 0.3 (0.0) | 1.0 (0.2) | 0.3 (0.0) | - | 0.0 (0.0) | 0.0 (0.0) |
| | ASN | 0.4 (0.0) | 0.3 (0.0) | 0.4 (0.0) | 0.3 (0.0) | 0.3 (0.0) | 1.6 (0.3) | 0.9 (0.0) | - | 0.0 (0.0) | 0.3 (0.0) |
| | ASP | 0.2 (0.0) | 0.0 (0.0) | 0.0 (0.0) | 0.0 (0.0) | 0.0 (0.0) | 0.8 (0.4) | 0.2 (0.0) | - | 0.2 (0.0) | 0.5 (0.0) |
| | CYS | 0.0 (0.0) | 0.0 (0.0) | 0.0 (0.0) | 0.0 (0.0) | 0.0 (0.0) | 0.9 (0.3) | 0.2 (0.0) | - | 0.0 (0.0) | 0.1 (0.0) |
| | GLN | 0.0 (0.0) | 0.0 (0.0) | 0.0 (0.0) | 0.0 (0.0) | 0.2 (0.0) | 1.5 (0.7) | 0.3 (0.0) | - | 0.0 (0.0) | 0.1 (0.0) |
| | GLU | 0.0 (0.0) | 0.0 (0.0) | 0.0 (0.0) | 0.0 (0.0) | 0.0 (0.0) | 1.7 (0.1) | 0.2 (0.0) | - | 0.0 (0.0) | 0.2 (0.1) |
| | GLY | 0.0 (0.0) | 0.0 (0.0) | 0.0 (0.0) | 0.0 (0.0) | 0.0 (0.0) | 0.0 (0.0) | 0.0 (0.0) | - | 0.0 (0.0) | 0.2 (0.0) |
| | HID | 0.0 (1.0) | 0.0 (1.0) | 0.0 (1.0) | 0.0 (1.0) | 0.0 (1.0) | 0.5 (1.2) | 0.0 (1.0) | - | 0.0 (1.0) | 0.0 (0.0) |
| | HIE | 0.0 (1.0) | 0.0 (1.0) | 0.0 (1.0) | 0.0 (1.0) | 0.0 (1.0) | 0.4 (1.5) | 0.0 (1.0) | - | 0.0 (1.0) | 0.1 (1.0) |
| | HIP | 0.0 (1.0) | 0.0 (1.0) | 0.0 (1.0) | 0.0 (1.0) | 0.0 (1.0) | 0.3 (1.7) | 0.0 (1.0) | - | 0.0 (1.0) | 0.1 (1.1) |
| | ILE | 0.0 (0.0) | 0.0 (0.0) | 0.0 (0.0) | 0.0 (0.0) | 0.0 (0.0) | 0.9 (0.5) | 0.0 (0.0) | - | 0.0 (0.0) | 0.0 (1.1) |
| | LEU | 0.0 (0.0) | 0.0 (0.0) | 0.0 (0.0) | 0.0 (0.0) | 0.0 (0.0) | 0.5 (0.0) | 0.0 (0.0) | - | 0.0 (1.0) | 0.1 (0.1) |
| | LYS | 0.0 (0.0) | 0.0 (0.0) | 0.0 (0.0) | 0.0 (0.0) | 0.0 (0.0) | 1.1 (0.0) | 0.0 (0.0) | - | 0.0 (1.0) | 0.1 (0.0) |
| | MET | 0.0 (0.0) | 0.0 (0.0) | 0.0 (0.0) | 0.0 (0.0) | 0.0 (0.0) | 1.1 (0.2) | 0.2 (0.0) | - | 0.0 (0.0) | 0.1 (0.0) |
| | PHE | 0.0 (2.0) | 0.0 (2.0) | 0.0 (2.0) | 0.0 (2.0) | 0.0 (2.0) | 0.6 (3.1) | 0.0 (2.0) | - | 0.0 (2.0) | 0.2 (0.0) |
| | SER | 0.0 (0.0) | 0.0 (0.0) | 0.0 (0.0) | 0.0 (0.0) | 0.2 (0.0) | 1.2 (0.0) | 0.4 (0.0) | - | 0.0 (0.0) | 0.1 (2.1) |
| | THR | 0.0 (0.0) | 0.0 (0.0) | 0.0 (0.0) | 0.0 (0.0) | 0.3 (0.0) | 1.2 (0.3) | 0.5 (0.0) | - | 0.0 (0.0) | 0.2 (0.0) |
| | TRP | 0.0 (2.0) | 0.0 (2.0) | 0.0 (2.0) | 0.0 (2.0) | 0.0 (2.0) | 0.0 (3.4) | 0.0 (2.0) | - | 0.0 (2.0) | 0.3 (0.0) |
| | TYR | 0.0 (4.0) | 0.0 (4.0) | 0.0 (4.0) | 0.0 (4.0) | 0.0 (4.0) | 0.4 (4.5) | 0.0 (4.0) | - | 0.0 (4.0) | 0.0 (2.2) |
| | VAL | 0.0 (0.0) | 0.0 (0.0) | 0.0 (0.0) | 0.0 (0.0) | 0.0 (0.0) | 0.8 (0.2) | 0.0 (0.0) | - | 0.0 (0.0) | 0.1 (4.1) |
| | | 0.0 (0.5) | 0.0 (0.5) | 0.0 (0.5) | 0.0 (0.5) | 0.1 (0.5) | 0.8 (0.9) | 0.1 (0.5) | - | 0.0 (0.5) | 0.1 (0.0) |
| A/328 | ALA | 0.0 (0.0) | 0.0 (0.0) | 0.0 (0.0) | 0.0 (0.0) | 0.0 (0.0) | 0.0 (0.0) | 0.0 (0.0) | 0.0 (0.0) | - | 0.0 (0.0) |

FIGURE 7G

| Position | Substate | A/235 | A/236 | A/237 | A/239 | A/266 | A/267 | A/325 | A/327 | A/328 | Average |
|---|---|---|---|---|---|---|---|---|---|---|---|
| | ARG | 0.0 (0.0) | 0.0 (0.0) | 0.9 (0.0) | 0.0 (0.0) | 0.0 (0.0) | 0.0 (0.0) | 0.8 (0.4) | 0.0 (0.0) | - | 0.2 (0.0) |
| | ASN | 0.3 (0.0) | 0.3 (0.0) | 0.2 (3.0) | 0.3 (0.0) | 0.4 (0.0) | 0.3 (0.0) | 1.2 (1.6) | 0.3 (0.0) | - | 0.4 (0.6) |
| | ASP | 0.0 (0.0) | 0.0 (0.0) | 0.4 (0.1) | 0.2 (0.0) | 0.0 (0.0) | 0.0 (0.0) | 0.7 (0.7) | 0.0 (0.0) | - | 0.2 (0.1) |
| | CYS | 0.0 (0.0) | 0.0 (0.0) | 0.2 (0.0) | 0.0 (0.0) | 0.0 (0.0) | 0.0 (0.0) | 0.6 (0.1) | 0.0 (0.0) | - | 0.1 (0.0) |
| | GLN | 0.0 (0.0) | 0.3 (0.0) | 0.2 (0.1) | 0.2 (0.0) | 0.4 (0.0) | 0.4 (0.0) | 0.9 (0.3) | 0.4 (0.0) | - | 0.3 (0.1) |
| | GLU | 0.0 (0.0) | 0.0 (0.0) | 0.7 (0.0) | 0.0 (0.0) | 0.2 (0.0) | 0.0 (0.0) | 1.1 (0.6) | 0.0 (0.0) | - | 0.2 (0.1) |
| | GLY | 0.0 (0.0) | 0.0 (0.0) | 0.0 (0.0) | 0.0 (0.0) | 0.0 (0.0) | 0.0 (0.0) | 0.0 (0.0) | 0.0 (0.0) | - | 0.0 (0.0) |
| | HID | 0.0 (0.0) | 0.0 (0.0) | 0.2 (2.0) | 0.2 (0.0) | 0.0 (0.0) | 0.0 (0.0) | 0.7 (0.8) | 0.0 (0.0) | - | 0.1 (0.4) |
| | HIE | 0.0 (1.0) | 0.4 (0.9) | 0.0 (2.0) | 0.4 (0.9) | 0.3 (0.9) | 0.2 (1.0) | 1.1 (1.1) | 0.3 (0.9) | - | 0.3 (1.1) |
| | HIP | 0.0 (0.0) | 0.0 (0.0) | 0.2 (2.0) | 0.0 (0.0) | 0.2 (0.0) | 0.0 (0.0) | 1.1 (1.0) | 0.2 (0.0) | - | 0.2 (0.4) |
| | ILE | 0.0 (0.0) | 0.0 (0.0) | 0.6 (0.3) | 0.0 (0.0) | 0.0 (0.0) | 0.0 (0.0) | 0.3 (0.1) | 0.0 (0.0) | - | 0.1 (0.1) |
| | LEU | 0.0 (0.0) | 0.0 (0.0) | 0.6 (0.2) | 0.0 (0.0) | 0.6 (0.0) | 0.0 (0.0) | 0.7 (0.0) | 0.0 (0.0) | - | 0.2 (0.0) |
| | LYS | 0.0 (0.0) | 0.0 (0.0) | 0.8 (0.0) | 0.2 (0.0) | 0.0 (0.0) | 0.0 (0.0) | 1.1 (0.2) | 0.0 (0.0) | - | 0.3 (0.0) |
| | MET | 0.0 (0.0) | 0.0 (0.0) | 0.6 (0.1) | 0.0 (0.0) | 0.0 (0.0) | 0.0 (0.0) | 0.6 (0.0) | 0.0 (0.0) | - | 0.1 (0.0) |
| | PHE | 0.0 (4.0) | 0.0 (4.0) | 0.0 (4.0) | 0.0 (4.0) | 0.0 (4.0) | 0.0 (4.0) | 0.0 (4.0) | 0.0 (4.0) | - | 0.0 (4.0) |
| | SER | 0.0 (0.0) | 0.0 (0.0) | 1.0 (0.0) | 0.0 (0.0) | 0.0 (0.0) | 0.0 (0.0) | 1.3 (0.1) | 0.2 (0.0) | - | 0.3 (0.0) |
| | THR | 0.0 (0.0) | 0.0 (0.0) | 0.7 (0.4) | 0.0 (0.0) | 0.3 (0.0) | 0.3 (0.0) | 0.9 (0.4) | 0.3 (0.0) | - | 0.3 (0.1) |
| | TRP | 0.0 (2.0) | 0.0 (2.0) | 0.3 (7.8) | 0.0 (2.0) | 0.0 (2.0) | 0.0 (2.0) | 0.3 (2.8) | 0.0 (2.0) | - | 0.1 (2.8) |
| | TYR | 0.0 (2.0) | 0.0 (2.0) | 0.0 (2.0) | 0.0 (2.0) | 0.0 (2.0) | 0.0 (2.0) | 0.0 (2.0) | 0.0 (2.0) | - | 0.0 (2.0) |
| | VAL | 0.0 (0.0) | 0.0 (0.0) | 0.2 (0.0) | 0.0 (0.0) | 0.0 (0.0) | 0.0 (0.0) | 0.5 (0.2) | 0.0 (0.0) | - | 0.1 (0.0) |
| | | 0.0 (0.4) | 0.0 (0.4) | 0.4 (1.2) | 0.1 (0.4) | 0.1 (0.4) | 0.1 (0.4) | 0.7 (0.8) | 0.1 (0.4) | - | |

TABLE 2: SHANNON'S ENTROPY AND CLASH COUNT FOR THE MIXED SIDE-CHAIN FRICTION CALCULATION

| Position | Substate | A/235 | A/236 | A/237 | A/239 | A/266 | A/267 | A/325 | A/327 | A/328 | Average |
|---|---|---|---|---|---|---|---|---|---|---|---|
| A/235 | ALA | - | 0.0 (0.0) | 0.0 (0.0) | 0.0 (0.0) | 0.0 (0.0) | 0.0 (0.0) | 0.0 (0.0) | 0.0 (0.0) | 0.0 (0.0) | 0.0 (0.0) |
| | ARG | - | 0.6 (0.0) | 0.0 (0.0) | 0.0 (0.0) | 0.0 (0.0) | 0.3 (0.0) | 0.0 (0.0) | 0.3 (0.0) | 0.0 (0.0) | 0.2 (0.0) |
| | ASN | - | 0.6 (0.0) | 0.3 (0.0) | 0.0 (0.0) | 0.0 (0.0) | 0.4 (0.0) | 0.0 (0.0) | 0.4 (0.0) | 0.0 (0.0) | 0.2 (0.0) |
| | ASP | - | 0.9 (0.5) | 0.4 (0.9) | 0.3 (0.9) | 0.2 (1.0) | 0.3 (0.9) | 0.2 (1.0) | 0.5 (0.9) | 0.3 (0.9) | 0.4 (0.9) |

FIGURE 7H

| Position | Substate | A/235 | A/236 | A/237 | A/239 | A/266 | A/267 | A/325 | A/327 | A/328 | Average |
|---|---|---|---|---|---|---|---|---|---|---|---|
| | CYS | - | 0.0 (0.0) | 0.0 (0.0) | 0.0 (0.0) | 0.0 (0.0) | 0.0 (0.0) | 0.0 (0.0) | 0.0 (0.0) | 0.0 (0.0) | 0.0 (0.0) |
| | GLN | - | 0.3 (0.0) | 0.0 (0.0) | 0.0 (0.0) | 0.0 (0.0) | 0.0 (0.0) | 0.0 (0.0) | 0.2 (0.0) | 0.0 (0.0) | 0.1 (0.0) |
| | GLU | - | 0.3 (0.0) | 0.0 (0.0) | 0.0 (0.0) | 0.0 (0.0) | 0.4 (0.0) | 0.0 (0.0) | 0.5 (0.0) | 0.0 (0.0) | 0.2 (0.0) |
| | GLY | - | 0.0 (0.0) | 0.0 (0.0) | 0.0 (0.0) | 0.0 (0.0) | 0.0 (0.0) | 0.0 (0.0) | 0.0 (0.0) | 0.0 (0.0) | 0.0 (0.0) |
| | HID | - | 0.2 (0.0) | 0.0 (0.0) | 0.2 (0.0) | 0.0 (0.0) | 0.3 (0.0) | 0.2 (0.0) | 0.3 (0.0) | 0.0 (0.0) | 0.2 (0.0) |
| | HIE | - | 0.2 (0.0) | 0.0 (0.0) | 0.0 (0.0) | 0.0 (0.0) | 0.0 (0.0) | 0.0 (0.0) | 0.2 (0.0) | 0.0 (0.0) | 0.0 (0.0) |
| | HIP | - | 0.0 (0.0) | 0.0 (0.0) | 0.0 (0.0) | 0.0 (0.0) | 0.0 (0.0) | 0.0 (0.0) | 0.3 (0.0) | 0.0 (0.0) | 0.0 (0.0) |
| | ILE | - | 0.4 (0.1) | 0.0 (0.0) | 0.0 (0.0) | 0.0 (0.0) | 0.0 (0.0) | 0.0 (0.0) | 0.0 (0.0) | 0.0 (0.0) | 0.1 (0.0) |
| | LEU | - | 0.2 (0.0) | 0.0 (0.0) | 0.0 (0.0) | 0.0 (0.0) | 0.0 (0.0) | 0.0 (0.0) | 0.0 (0.0) | 0.0 (0.0) | 0.0 (0.0) |
| | LYS | - | 0.5 (0.0) | 0.0 (0.0) | 0.0 (0.0) | 0.0 (0.0) | 0.2 (0.0) | 0.0 (0.0) | 0.2 (0.0) | 0.0 (0.0) | 0.1 (0.0) |
| | MET | - | 0.4 (0.0) | 0.0 (0.0) | 0.0 (0.0) | 0.0 (0.0) | 0.0 (0.0) | 0.0 (0.0) | 0.0 (0.0) | 0.0 (0.0) | 0.0 (0.0) |
| | PHE | - | 0.0 (0.0) | 0.0 (0.0) | 0.0 (0.0) | 0.0 (0.0) | 0.0 (0.0) | 0.0 (0.0) | 0.0 (0.0) | 0.0 (0.0) | 0.0 (0.0) |
| | SER | - | 0.5 (0.0) | 0.0 (0.0) | 0.0 (0.0) | 0.0 (0.0) | 0.4 (0.0) | 0.0 (0.0) | 0.4 (0.0) | 0.0 (0.0) | 0.2 (0.0) |
| | THR | - | 0.6 (0.1) | 0.0 (0.0) | 0.0 (0.0) | 0.0 (0.0) | 0.0 (0.0) | 0.0 (0.0) | 0.0 (0.0) | 0.0 (0.0) | 0.1 (0.0) |
| | TRP | - | 0.0 (0.0) | 0.0 (0.0) | 0.0 (0.0) | 0.0 (0.0) | 0.0 (0.0) | 0.0 (0.0) | 0.0 (0.0) | 0.0 (0.0) | 0.0 (0.0) |
| | TYR | - | 0.0 (0.0) | 0.0 (0.0) | 0.0 (0.0) | 0.0 (0.0) | 0.4 (0.0) | 0.0 (0.0) | 0.2 (0.0) | 0.0 (0.0) | 0.1 (0.0) |
| | VAL | - | 0.5 (0.1) | 0.0 (0.0) | 0.0 (0.0) | 0.0 (0.0) | 0.0 (0.0) | 0.0 (0.0) | 0.0 (0.0) | 0.0 (0.0) | 0.1 (0.0) |
| A/236 | ALA | 0.0 (0.0) | 0.3 (0.1) | 0.0 (0.0) | 0.0 (0.0) | 0.0 (0.0) | 0.1 (0.0) | 0.0 (0.0) | 0.2 (0.0) | 0.0 (0.0) | 0.1 (0.0) |
| | ARG | 0.0 (1.0) | - | 0.0 (1.0) | 0.0 (1.0) | 0.0 (1.0) | 0.0 (1.0) | 0.0 (1.0) | 0.0 (1.0) | 0.0 (1.0) | 0.0 (1.0) |
| | ASN | 0.0 (7.0) | - | 0.0 (7.0) | 0.0 (7.0) | 0.0 (7.0) | 0.0 (7.1) | 0.0 (7.0) | 0.0 (7.0) | 0.0 (7.0) | 0.0 (7.0) |
| | ASP | 0.0 (4.0) | - | 0.0 (4.0) | 0.0 (4.0) | 0.0 (4.0) | 0.0 (4.0) | 0.0 (4.0) | 0.0 (4.0) | 0.0 (4.0) | 0.0 (4.0) |
| | CYS | 0.0 (4.0) | - | 0.0 (4.0) | 0.0 (4.0) | 0.0 (4.0) | 0.0 (4.0) | 0.0 (4.0) | 0.0 (4.0) | 0.0 (4.0) | 0.0 (4.0) |
| | GLN | 0.0 (2.0) | - | 0.0 (2.0) | 0.0 (2.0) | 0.0 (2.0) | 0.0 (2.0) | 0.0 (2.0) | 0.0 (2.0) | 0.0 (2.0) | 0.0 (2.0) |
| | GLU | 0.0 (5.0) | - | 0.0 (5.0) | 0.0 (5.0) | 0.0 (5.0) | 0.0 (5.0) | 0.0 (5.0) | 0.0 (5.0) | 0.0 (5.0) | 0.0 (5.0) |
| | GLY | 0.0 (4.0) | - | 0.0 (4.0) | 0.0 (4.0) | 0.0 (4.0) | 0.0 (4.0) | 0.0 (4.0) | 0.0 (4.0) | 0.0 (4.0) | 0.0 (4.0) |
| | HID | 0.0 (0.0) | - | 0.0 (0.0) | 0.0 (0.0) | 0.0 (0.0) | 0.0 (0.0) | 0.0 (0.0) | 0.0 (0.0) | 0.0 (0.0) | 0.0 (0.0) |
| | HIE | 0.0 (9.0) | - | 0.0 (9.0) | 0.0 (9.0) | 0.0 (9.0) | 0.0 (9.0) | 0.0 (9.0) | 0.0 (9.0) | 0.0 (9.0) | 0.0 (9.0) |
| | HIP | 0.0 (9.0) | - | 0.0 (9.0) | 0.0 (9.0) | 0.0 (9.0) | 0.0 (9.0) | 0.0 (9.0) | 0.0 (9.0) | 0.0 (9.0) | 0.0 (9.0) |
| | ILE | 0.0 (5.0) | - | 0.0 (5.0) | 0.0 (5.0) | 0.0 (5.0) | 0.0 (5.0) | 0.0 (5.0) | 0.0 (5.0) | 0.0 (5.0) | 0.0 (5.0) |

FIGURE 7I

| Position | Substate | A/235 | A/236 | A/237 | A/239 | A/266 | A/267 | A/325 | A/327 | A/328 | Average |
|---|---|---|---|---|---|---|---|---|---|---|---|
| | LEU | 0.0 (8.0) | - | 0.0 (8.0) | 0.0 (8.0) | 0.0 (8.0) | 0.0 (8.0) | 0.0 (8.0) | 0.0 (8.0) | 0.0 (8.0) | 0.0 (8.0) |
| | LYS | 0.2 (8.8) | - | 0.0 (9.0) | 0.0 (9.0) | 0.0 (9.0) | 0.0 (9.0) | 0.0 (9.0) | 0.0 (9.0) | 0.0 (9.0) | 0.0 (9.0) |
| | MET | 0.2 (3.1) | - | 0.0 (3.0) | 0.0 (3.0) | 0.0 (3.0) | 0.0 (3.0) | 0.0 (3.0) | 0.0 (3.0) | 0.0 (3.0) | 0.0 (3.0) |
| | PHE | 0.0 (10.0) | - | 0.0 (10.0) | 0.0 (10.0) | 0.0 (10.0) | 0.0 (10.0) | 0.0 (10.0) | 0.0 (10.0) | 0.0 (10.0) | 0.0 (10.0) |
| | SER | 0.2 (2.0) | - | 0.0 (2.0) | 0.0 (2.0) | 0.0 (2.0) | 0.0 (2.0) | 0.0 (2.0) | 0.0 (2.0) | 0.0 (2.0) | 0.0 (2.0) |
| | THR | 0.5 (3.0) | - | 0.6 (3.0) | 0.4 (3.0) | 0.4 (3.0) | 0.2 (3.0) | 0.4 (3.0) | 0.3 (3.0) | 0.5 (3.0) | 0.4 (3.0) |
| | TRP | 0.0 (8.0) | - | 0.0 (8.0) | 0.0 (8.0) | 0.0 (8.0) | 0.0 (8.0) | 0.0 (8.0) | 0.0 (8.0) | 0.0 (8.0) | 0.0 (8.0) |
| | TYR | 0.0 (8.0) | - | 0.0 (8.0) | 0.0 (8.0) | 0.0 (8.0) | 0.0 (8.0) | 0.0 (8.0) | 0.0 (8.0) | 0.0 (8.0) | 0.0 (8.0) |
| | VAL | 0.0 (3.0) | - | 0.0 (3.0) | 0.0 (3.0) | 0.0 (3.0) | 0.0 (3.0) | 0.0 (3.0) | 0.0 (3.0) | 0.0 (3.0) | 0.0 (3.0) |
| A/237 | ALA | 0.1 (5.4) | 0.0 (0.0) | 0.0 (5.4) | 0.0 (5.4) | 0.0 (5.4) | 0.0 (5.4) | 0.0 (5.4) | 0.0 (5.4) | 0.0 (5.4) | |
| | ARG | 0.0 (0.0) | 0.0 (0.0) | - | 0.0 (0.0) | 0.0 (0.0) | 0.0 (0.0) | 0.0 (0.0) | 0.0 (0.0) | 0.0 (0.2) | 0.0 (0.0) |
| | ASN | 0.0 (0.0) | 0.0 (0.0) | - | 0.3 (0.0) | 0.3 (0.0) | 0.0 (0.0) | 0.2 (0.0) | 0.0 (0.0) | 1.2 (0.2) | 0.3 (0.0) |
| | ASP | 0.0 (0.0) | 0.0 (0.0) | - | 0.0 (0.0) | 0.0 (0.0) | 0.0 (0.0) | 0.0 (0.0) | 0.0 (0.0) | 0.5 (0.4) | 0.1 (0.1) |
| | CYS | 0.0 (0.0) | 0.0 (0.0) | - | 0.0 (0.0) | 0.0 (0.0) | 0.0 (0.0) | 0.0 (0.0) | 0.0 (0.0) | 0.4 (0.3) | 0.1 (0.0) |
| | GLN | 0.4 (0.0) | 0.5 (0.0) | - | 0.3 (0.0) | 0.3 (0.0) | 0.4 (0.0) | 0.6 (0.0) | 0.7 (0.0) | 0.2 (0.3) | 0.0 (0.0) |
| | GLU | 0.0 (0.0) | 0.0 (0.0) | - | 0.4 (0.0) | 0.0 (0.0) | 0.0 (0.0) | 0.3 (0.0) | 0.0 (0.0) | 0.8 (0.2) | 0.5 (0.0) |
| | GLY | 0.0 (0.0) | 0.0 (0.0) | - | 0.0 (0.0) | 0.0 (0.0) | 0.0 (0.0) | 0.0 (0.0) | 0.0 (0.0) | 1.1 (0.7) | 0.2 (0.1) |
| | HID | 0.0 (0.0) | 0.0 (0.0) | - | 0.0 (0.0) | 0.0 (0.0) | 0.0 (0.0) | 0.0 (0.0) | 0.0 (0.0) | 0.0 (0.0) | 0.0 (0.0) |
| | HIE | 0.0 (0.0) | 0.0 (0.0) | - | 0.3 (0.0) | 0.2 (0.0) | 0.0 (0.0) | 0.4 (0.0) | 0.0 (0.0) | 0.6 (0.2) | 0.1 (0.0) |
| | HIP | 0.0 (0.0) | 0.0 (0.0) | - | 0.0 (0.0) | 0.0 (0.0) | 0.0 (0.0) | 0.0 (0.0) | 0.0 (0.0) | 0.8 (0.3) | 0.2 (0.0) |
| | ILE | 0.0 (1.0) | 0.0 (1.0) | - | 0.0 (1.0) | 0.0 (1.0) | 0.0 (1.0) | 0.0 (1.0) | 0.0 (1.0) | 0.8 (0.3) | 0.1 (0.0) |
| | LEU | 0.0 (0.0) | 0.0 (0.0) | - | 0.0 (0.0) | 0.0 (0.0) | 0.0 (0.0) | 0.7 (1.0) | 0.0 (1.0) | 0.9 (1.0) | 0.2 (1.0) |
| | LYS | 0.0 (0.0) | 0.2 (0.0) | - | 0.3 (0.0) | 0.3 (0.0) | 0.0 (0.0) | 0.0 (0.0) | 0.0 (0.0) | 0.2 (0.5) | 0.0 (0.1) |
| | MET | 0.4 (0.0) | 0.7 (0.0) | - | 0.6 (0.0) | 0.6 (0.0) | 0.5 (0.0) | 0.5 (0.0) | 0.0 (0.0) | 1.2 (0.5) | 0.3 (0.1) |
| | PHE | 0.0 (0.0) | 0.0 (0.0) | - | 0.0 (0.0) | 0.0 (0.0) | 0.0 (0.0) | 0.0 (0.0) | 0.7 (0.0) | 1.4 (0.8) | 0.7 (0.1) |
| | SER | 0.4 (0.0) | 0.7 (0.0) | - | 0.4 (0.0) | 0.6 (0.0) | 0.7 (0.0) | 0.8 (0.0) | 0.0 (0.0) | 0.4 (0.3) | 0.0 (0.0) |
| | THR | 0.6 (0.0) | 0.7 (0.0) | - | 0.5 (0.0) | 0.7 (0.0) | 0.6 (0.0) | 0.6 (0.4) | 0.8 (0.0) | 1.1 (0.4) | 0.7 (0.1) |
| | TRP | 0.0 (0.0) | 0.0 (0.0) | - | 0.0 (0.0) | 0.0 (0.0) | 0.0 (0.0) | 0.0 (0.0) | 0.7 (0.0) | 0.9 (0.4) | 0.1 (0.1) |
| | TYR | 0.0 (0.0) | 0.0 (0.0) | - | 0.5 (0.0) | 0.0 (0.0) | 0.0 (0.0) | 0.2 (0.0) | 0.0 (0.0) | 0.6 (0.4) | 0.2 (0.0) |

FIGURE 7J

| Position | Substrate | A/235 | A/236 | A/237 | A/239 | A/266 | A/267 | A/325 | A/327 | A/328 | Average |
|---|---|---|---|---|---|---|---|---|---|---|---|
| | VAL | 0.0 (0.0) | 0.0 (0.0) | - | 0.0 (0.0) | 0.0 (0.0) | 0.0 (0.0) | 0.3 (0.1) | 0.0 (0.0) | 0.0 (0.0) | 0.0 (0.0) |
| A/239 | ALA | 0.1 (0.0) | 0.1 (0.0) | 0.0 (0.0) | 0.2 (0.0) | 0.1 (0.0) | 0.1 (0.0) | 0.3 (0.1) | 0.1 (0.0) | 0.7 (0.4) | |
| | ARG | 0.0 (0.0) | 0.0 (0.0) | 0.6 (0.0) | - | 0.0 (0.0) | 0.0 (0.0) | 0.0 (0.0) | 0.0 (0.0) | 0.3 (0.0) | 0.1 (0.0) |
| | ASN | 0.0 (0.0) | 0.0 (0.0) | 0.0 (0.0) | - | 0.0 (0.0) | 0.0 (0.0) | 0.2 (0.0) | 0.0 (0.0) | 0.0 (0.0) | 0.0 (0.0) |
| | ASP | 0.0 (0.0) | 0.0 (0.0) | 0.2 (0.0) | - | 0.0 (0.0) | 0.0 (0.0) | 0.0 (0.0) | 0.0 (0.0) | 0.0 (0.0) | 0.0 (0.0) |
| | CYS | 0.0 (0.0) | 0.0 (0.0) | 0.0 (0.0) | - | 0.0 (0.0) | 0.0 (0.0) | 0.0 (0.0) | 0.0 (0.0) | 0.0 (0.0) | 0.0 (0.0) |
| | GLN | 0.0 (0.0) | 0.0 (0.0) | 0.0 (0.0) | - | 0.0 (0.0) | 0.0 (0.0) | 0.0 (0.0) | 0.0 (0.0) | 0.0 (0.0) | 0.0 (0.0) |
| | GLU | 0.0 (0.0) | 0.2 (0.0) | 0.3 (0.0) | - | 0.3 (0.0) | 0.3 (0.0) | 0.0 (0.0) | 0.2 (0.0) | 0.0 (0.0) | 0.2 (0.0) |
| | GLY | 0.0 (0.0) | 0.0 (0.0) | 0.0 (0.0) | - | 0.0 (0.0) | 0.0 (0.0) | 0.0 (0.0) | 0.0 (0.0) | 0.0 (0.0) | 0.0 (0.0) |
| | HID | 0.0 (0.0) | 0.0 (0.0) | 0.0 (0.0) | - | 0.0 (0.0) | 0.0 (0.0) | 0.0 (0.0) | 0.0 (0.0) | 0.0 (0.0) | 0.0 (0.0) |
| | HIE | 0.0 (0.0) | 0.0 (0.0) | 0.0 (0.0) | - | 0.0 (0.0) | 0.0 (0.0) | 0.0 (0.0) | 0.0 (0.0) | 0.0 (0.0) | 0.0 (0.0) |
| | HIP | 0.0 (0.0) | 0.2 (0.0) | 0.5 (0.0) | - | 0.2 (0.0) | 0.0 (0.0) | 0.2 (0.0) | 0.0 (0.0) | 0.3 (0.0) | 0.2 (0.0) |
| | ILE | 0.0 (0.0) | 0.0 (0.0) | 0.0 (0.0) | - | 0.0 (0.0) | 0.0 (0.0) | 0.0 (0.0) | 0.0 (0.0) | 0.0 (0.0) | 0.0 (0.0) |
| | LEU | 0.0 (0.0) | 0.0 (0.0) | 0.2 (0.0) | - | 0.0 (0.0) | 0.0 (0.0) | 0.0 (0.0) | 0.0 (0.0) | 0.0 (0.0) | 0.0 (0.0) |
| | LYS | 0.0 (0.0) | 0.5 (0.0) | 0.9 (0.0) | - | 0.4 (0.0) | 0.4 (0.0) | 0.5 (0.0) | 0.4 (0.0) | 0.5 (0.0) | 0.5 (0.0) |
| | MET | 0.0 (0.0) | 0.0 (0.0) | 0.0 (0.0) | - | 0.0 (0.0) | 0.0 (0.0) | 0.0 (0.0) | 0.0 (0.0) | 0.0 (0.0) | 0.0 (0.0) |
| | PHE | 0.0 (0.0) | 0.2 (0.0) | 0.3 (0.0) | - | 0.2 (0.0) | 0.0 (0.0) | 0.0 (0.0) | 0.0 (0.0) | 0.0 (0.0) | 0.1 (0.0) |
| | SER | 0.0 (0.0) | 0.0 (0.0) | 0.0 (0.0) | - | 0.0 (0.0) | 0.0 (0.0) | 0.0 (0.0) | 0.0 (0.0) | 0.0 (0.0) | 0.0 (0.0) |
| | THR | 0.0 (0.0) | 0.0 (0.0) | 0.3 (0.0) | - | 0.0 (0.0) | 0.0 (0.0) | 0.0 (0.0) | 0.2 (0.0) | 0.2 (0.0) | 0.1 (0.0) |
| | TRP | 0.0 (0.0) | 0.0 (0.0) | 0.7 (0.0) | - | 0.0 (0.0) | 0.0 (0.0) | 0.0 (0.0) | 0.0 (0.0) | 0.0 (0.0) | 0.1 (0.0) |
| | TYR | 0.0 (0.0) | 0.2 (0.0) | 0.8 (0.0) | - | 0.4 (0.0) | 0.0 (0.0) | 0.0 (0.0) | 0.0 (0.0) | 0.2 (0.0) | 0.2 (0.0) |
| | VAL | 0.0 (0.0) | 0.0 (0.0) | 0.0 (0.0) | 0.0 (0.0) | 0.0 (0.0) | 0.0 (0.0) | 0.0 (0.0) | 0.0 (0.0) | 0.0 (0.0) | 0.0 (0.0) |
| A/266 | ALA | 0.0 (0.0) | 0.1 (0.0) | 0.2 (0.0) | 0.0 (0.0) | 0.1 (0.0) | 0.0 (0.0) | 0.0 (0.0) | 0.0 (0.0) | 0.1 (0.0) | 0.0 (0.0) |
| | ARG | 0.0 (2.0) | 0.0 (2.0) | 0.0 (2.0) | 0.0 (2.0) | - | 0.0 (2.0) | 0.0 (0.0) | 0.0 (2.0) | 0.3 (1.8) | 0.1 (1.9) |
| | ASN | 0.0 (0.0) | 0.0 (0.0) | 0.0 (0.0) | 0.0 (0.0) | - | 0.2 (0.0) | 0.8 (1.2) | 0.2 (0.0) | 0.3 (0.0) | 0.1 (0.0) |
| | ASP | 0.0 (0.0) | 0.0 (0.0) | 0.0 (0.0) | 0.0 (0.0) | - | 0.0 (0.0) | 0.4 (0.0) | 0.2 (0.0) | 0.2 (0.0) | 0.1 (0.0) |
| | CYS | 0.0 (0.0) | 0.0 (0.0) | 0.0 (0.0) | 0.0 (0.0) | - | 0.0 (0.0) | 0.4 (0.0) | 0.0 (0.0) | 0.0 (0.0) | 0.0 (0.0) |
| | GLN | 0.3 (0.0) | 0.4 (0.0) | 0.5 (0.0) | 0.4 (0.0) | - | 1.0 (0.0) | 0.6 (0.0) | 0.8 (0.0) | 0.7 (0.0) | 0.6 (0.0) |

FIGURE 7K

| Position | Substate | A/235 | A/236 | A/237 | A/239 | A/266 | A/267 | A/325 | A/327 | A/328 | Average |
|---|---|---|---|---|---|---|---|---|---|---|---|
| | GLU | 0.2 (0.0) | 0.3 (0.0) | 0.3 (0.0) | 0.3 (0.0) | - | 0.3 (0.0) | 0.6 (0.0) | 0.3 (0.0) | 0.3 (0.0) | 0.3 (0.0) |
| | GLY | 0.0 (0.0) | 0.0 (0.0) | 0.0 (0.0) | 0.0 (0.0) | - | 0.0 (0.0) | 0.0 (0.0) | 0.0 (0.0) | 0.0 (0.0) | 0.0 (0.0) |
| | HID | 0.0 (1.0) | 0.0 (1.0) | 0.0 (1.0) | 0.0 (1.0) | - | 0.0 (1.0) | 0.0 (1.0) | 0.0 (1.0) | 0.0 (1.0) | 0.0 (1.0) |
| | HIE | 0.0 (1.0) | 0.0 (1.0) | 0.0 (1.0) | 0.0 (1.0) | - | 0.0 (1.0) | 0.0 (1.0) | 0.0 (1.0) | 0.0 (1.0) | 0.0 (1.0) |
| | HIP | 0.0 (1.0) | 0.0 (1.0) | 0.0 (1.0) | 0.0 (1.0) | - | 0.0 (1.0) | 0.0 (1.0) | 0.0 (1.0) | 0.0 (1.0) | 0.0 (1.0) |
| | ILE | 0.0 (0.0) | 0.0 (0.0) | 0.0 (0.0) | 0.0 (0.0) | - | 0.0 (0.0) | 0.0 (0.0) | 0.0 (0.0) | 0.0 (0.0) | 0.0 (0.0) |
| | LEU | 0.0 (0.0) | 0.0 (0.0) | 0.0 (0.0) | 0.0 (0.0) | - | 0.2 (0.0) | 0.3 (0.0) | 0.0 (0.0) | 0.0 (0.0) | 0.1 (0.0) |
| | LYS | 0.0 (0.0) | 0.2 (0.0) | 0.3 (0.0) | 0.0 (0.0) | - | 0.4 (0.0) | 0.4 (0.0) | 0.3 (0.0) | 0.4 (0.0) | 0.3 (0.0) |
| | MET | 0.0 (0.0) | 0.0 (0.0) | 0.0 (0.0) | 0.0 (0.0) | - | 0.3 (0.0) | 0.8 (0.0) | 0.0 (0.0) | 0.0 (0.0) | 0.1 (0.0) |
| | PHE | 0.0 (8.0) | 0.0 (8.0) | 0.0 (8.0) | 0.0 (8.0) | - | 0.0 (8.0) | 0.0 (8.0) | 0.0 (8.0) | 0.0 (8.0) | 0.0 (8.0) |
| | SER | 0.0 (0.0) | 0.3 (0.0) | 0.2 (0.0) | 0.3 (0.0) | - | 0.2 (0.0) | 0.6 (0.0) | 0.0 (0.0) | 0.0 (0.0) | 0.2 (0.0) |
| | THR | 0.0 (0.0) | 0.2 (0.0) | 0.0 (0.0) | 0.3 (0.0) | - | 0.0 (0.0) | 0.2 (0.0) | 0.0 (0.0) | 0.0 (0.0) | 0.1 (0.0) |
| | TRP | 0.0 (1.0) | 0.0 (1.0) | 0.0 (1.0) | 0.0 (1.0) | - | 0.0 (1.0) | 0.3 (1.6) | 0.0 (1.0) | 0.0 (1.0) | 0.0 (1.1) |
| | TYR | 0.0 (17.0) | 0.0 (17.0) | 0.0 (17.0) | 0.0 (17.0) | - | 0.0 (17.0) | 0.0 (17.0) | 0.0 (17.0) | 0.0 (17.0) | 0.0 (17.0) |
| | VAL | 0.0 (0.0) | 0.0 (0.0) | 0.0 (0.0) | 0.0 (0.0) | - | 0.0 (0.0) | 0.0 (0.0) | 0.0 (0.0) | 0.0 (0.0) | 0.0 (0.0) |
| A/267 | ALA | 0.0 (1.5) | 0.1 (1.5) | 0.1 (1.5) | 0.1 (1.5) | 0.0 (0.0) | 0.1 (1.5) | 0.3 (1.5) | 0.1 (1.5) | 0.1 (1.5) | |
| | ARG | 0.0 (0.0) | 0.0 (0.0) | 0.0 (0.0) | 0.0 (0.0) | 0.0 (0.0) | - | 0.0 (0.0) | 0.0 (0.0) | 0.0 (0.0) | 0.0 (0.0) |
| | ASN | 0.5 (0.0) | 0.4 (0.0) | 0.4 (0.0) | 0.0 (0.0) | 0.3 (0.0) | - | 0.4 (0.0) | 1.0 (0.0) | 0.4 (0.0) | 0.4 (0.0) |
| | ASP | 0.0 (0.0) | 0.4 (0.0) | 0.3 (0.0) | 0.2 (0.0) | 0.0 (0.0) | - | 0.4 (0.0) | 1.3 (0.0) | 0.3 (0.0) | 0.4 (0.0) |
| | CYS | 0.2 (0.0) | 0.2 (0.0) | 0.0 (0.0) | 0.0 (0.0) | 0.0 (0.0) | - | 0.2 (0.0) | 0.6 (0.0) | 0.0 (0.0) | 0.1 (0.0) |
| | GLN | 0.0 (0.0) | 0.0 (0.0) | 0.0 (0.0) | 0.0 (0.0) | 0.7 (0.0) | - | 0.0 (0.0) | 0.2 (0.0) | 0.0 (0.0) | 0.0 (0.0) |
| | GLU | 0.4 (0.0) | 0.5 (0.0) | 0.0 (0.0) | 0.3 (0.0) | 0.7 (0.0) | - | 0.7 (0.0) | 1.3 (0.0) | 0.5 (0.0) | 0.5 (0.0) |
| | GLY | 0.6 (0.0) | 0.4 (0.0) | 0.2 (0.0) | 0.0 (0.0) | 0.7 (0.0) | - | 0.4 (0.0) | 1.0 (0.0) | 0.5 (0.0) | 0.5 (0.0) |
| | HID | 0.0 (0.0) | 0.0 (0.0) | 0.0 (0.0) | 0.4 (0.0) | 0.0 (0.0) | - | 0.0 (0.0) | 0.0 (0.0) | 0.0 (0.0) | 0.0 (0.0) |
| | HIE | 0.6 (0.0) | 0.5 (0.0) | 0.3 (0.0) | 0.0 (0.0) | 0.6 (0.0) | - | 0.7 (0.0) | 1.1 (1.3) | 0.6 (0.2) | 0.6 (0.2) |
| | HIP | 0.0 (0.0) | 0.2 (0.0) | 0.0 (0.0) | 0.0 (0.0) | 0.4 (0.0) | - | 0.2 (0.0) | 1.0 (1.0) | 0.2 (0.0) | 0.2 (0.1) |
| | ILE | 0.0 (0.0) | 0.0 (0.0) | 0.0 (0.0) | 0.0 (0.0) | 0.0 (0.0) | - | 0.0 (0.0) | 1.0 (1.3) | 0.0 (0.0) | 0.1 (0.2) |
| | LEU | 0.0 (0.0) | 0.0 (0.0) | 0.0 (0.0) | 0.0 (0.0) | 0.3 (0.0) | - | 0.0 (0.0) | 0.2 (0.0) | 0.0 (0.0) | 0.1 (0.0) |
| | LYS | 0.5 (0.0) | 0.6 (0.0) | 0.4 (0.0) | 0.4 (0.0) | 0.4 (0.0) | - | 0.4 (0.0) | 1.5 (0.0) | 0.4 (0.0) | 0.6 (0.0) |

FIGURE 7L

| Position | Substate | A/235 | A/236 | A/237 | A/239 | A/266 | A/267 | A/325 | A/327 | A/328 | Average |
|---|---|---|---|---|---|---|---|---|---|---|---|
| | MET | 0.0 (0.0) | 0.2 (0.0) | 0.0 (0.0) | 0.0 (0.0) | 0.0 (0.0) | - | 0.0 (0.0) | 1.0 (0.0) | 0.0 (0.0) | 0.2 (0.0) |
| | PHE | 0.0 (0.0) | 0.0 (0.0) | 0.0 (0.0) | 0.0 (0.0) | 0.0 (0.0) | - | 0.0 (0.0) | 0.5 (2.1) | 0.0 (0.0) | 0.1 (0.3) |
| | SER | 0.0 (0.0) | 0.2 (0.0) | 0.0 (0.0) | 0.0 (0.0) | 0.2 (0.0) | - | 0.4 (0.0) | 0.6 (0.0) | 0.0 (0.0) | 0.2 (0.0) |
| | THR | 0.0 (0.0) | 0.3 (0.0) | 0.4 (0.0) | 0.4 (0.0) | 0.6 (0.0) | - | 0.5 (0.0) | 0.6 (0.0) | 0.4 (0.0) | 0.4 (0.0) |
| | TRP | 0.0 (0.0) | 0.0 (0.0) | 0.0 (0.0) | 0.0 (0.0) | 0.0 (0.0) | - | 0.0 (0.0) | 1.0 (1.9) | 0.0 (0.0) | 0.1 (0.2) |
| | TYR | 0.0 (2.0) | 0.2 (2.1) | 0.0 (2.0) | 0.0 (2.0) | 0.0 (2.0) | - | 0.3 (2.0) | 0.8 (3.4) | 0.0 (2.0) | 0.2 (2.2) |
| | VAL | 0.0 (0.0) | 0.0 (0.0) | 0.0 (0.0) | 0.0 (0.0) | 0.0 (0.0) | - | 0.2 (0.0) | 0.0 (0.0) | 0.0 (0.0) | 0.0 (0.0) |
| A/325 | | 0.1 (0.1) | 0.2 (0.1) | 0.1 (0.1) | 0.1 (0.1) | 0.2 (0.1) | 0.0 (0.0) | 0.2 (0.1) | 0.7 (0.5) | 0.2 (0.1) | |
| | ALA | 0.0 (0.0) | 0.0 (0.0) | 0.0 (0.0) | 0.0 (0.0) | 0.0 (0.0) | 0.0 (0.0) | - | 0.0 (0.0) | 0.0 (0.0) | 0.0 (0.0) |
| | ARG | 0.0 (0.0) | 0.0 (0.0) | 0.3 (0.1) | 0.0 (0.0) | 0.2 (0.0) | 0.0 (0.0) | - | 0.0 (0.0) | 1.1 (0.8) | 0.2 (0.1) |
| | ASN | 0.0 (0.0) | 0.0 (0.0) | 0.0 (0.0) | 0.0 (0.0) | 0.5 (0.0) | 0.0 (0.0) | - | 0.2 (0.0) | 0.0 (0.0) | 0.1 (0.0) |
| | ASP | 0.0 (0.0) | 0.4 (0.0) | 0.5 (0.0) | 0.4 (0.0) | 0.9 (0.0) | 0.4 (0.0) | - | 0.6 (0.0) | 0.2 (0.0) | 0.4 (0.0) |
| | CYS | 0.0 (0.0) | 0.0 (0.0) | 0.0 (0.0) | 0.0 (0.0) | 0.0 (0.0) | 0.0 (0.0) | - | 0.0 (0.0) | 0.5 (0.0) | 0.1 (0.0) |
| | GLN | 0.0 (0.0) | 0.0 (0.0) | 0.6 (0.0) | 0.3 (0.0) | 0.9 (0.0) | 0.3 (0.0) | - | 0.4 (0.0) | 0.7 (0.0) | 0.4 (0.0) |
| | GLU | 0.0 (0.0) | 0.0 (0.0) | 0.0 (0.0) | 0.0 (0.0) | 0.8 (0.2) | 0.0 (0.0) | - | 0.0 (0.0) | 0.0 (0.0) | 0.1 (0.0) |
| | GLY | 0.0 (0.0) | 0.0 (0.0) | 0.0 (0.0) | 0.0 (0.0) | 0.0 (0.0) | 0.0 (0.0) | - | 0.0 (0.0) | 0.0 (0.0) | 0.0 (0.0) |
| | HID | 0.0 (0.0) | 0.0 (0.0) | 0.2 (0.1) | 0.0 (0.0) | 0.5 (0.1) | 0.0 (0.0) | - | 0.0 (0.0) | 0.3 (0.2) | 0.1 (0.0) |
| | HIE | 0.0 (0.0) | 0.0 (0.0) | 0.0 (0.1) | 0.0 (0.0) | 0.0 (0.0) | 0.0 (0.0) | - | 0.0 (0.0) | 0.4 (0.3) | 0.1 (0.0) |
| | HIP | 0.0 (0.0) | 0.0 (0.0) | 0.0 (0.1) | 0.0 (0.0) | 0.0 (0.0) | 0.0 (0.0) | - | 0.0 (0.0) | 0.4 (0.3) | 0.1 (0.0) |
| | ILE | 0.0 (0.0) | 0.0 (0.0) | 0.0 (0.0) | 0.0 (0.0) | 0.5 (0.1) | 0.0 (0.0) | - | 0.0 (0.0) | 0.0 (0.0) | 0.1 (0.0) |
| | LEU | 0.0 (1.0) | 0.0 (1.0) | 0.0 (1.0) | 0.0 (1.0) | 0.2 (1.0) | 0.2 (1.0) | - | 0.2 (1.0) | 0.0 (1.0) | 0.1 (1.0) |
| | LYS | 0.0 (0.0) | 0.0 (0.0) | 0.5 (0.0) | 0.3 (0.0) | 0.8 (0.0) | 0.4 (0.0) | - | 0.3 (0.0) | 0.4 (0.0) | 0.3 (0.0) |
| | MET | 0.0 (0.0) | 0.0 (0.0) | 0.0 (0.0) | 0.0 (0.0) | 0.5 (0.0) | 0.0 (0.0) | - | 0.0 (0.0) | 0.0 (0.0) | 0.1 (0.0) |
| | PHE | 0.0 (1.0) | 0.0 (1.0) | 0.3 (4.6) | 0.0 (1.0) | 0.0 (1.0) | 0.0 (1.0) | - | 0.0 (1.0) | 0.3 (1.5) | 0.1 (1.5) |
| | SER | 0.0 (0.0) | 0.0 (0.0) | 0.0 (0.0) | 0.0 (0.0) | 0.4 (0.0) | 0.0 (0.0) | - | 0.0 (0.0) | 0.2 (0.0) | 0.1 (0.0) |
| | THR | 0.0 (0.0) | 0.0 (0.0) | 0.0 (0.0) | 0.0 (0.0) | 0.4 (0.1) | 0.0 (0.0) | - | 0.2 (0.0) | 0.9 (0.0) | 0.2 (0.0) |
| | TRP | 0.0 (0.0) | 0.0 (0.0) | 0.2 (0.3) | 0.0 (0.0) | 0.0 (0.0) | 0.0 (0.0) | - | 0.0 (0.0) | 0.4 (0.7) | 0.1 (0.1) |
| | TYR | 0.0 (10.0) | 0.0 (10.0) | 0.0 (10.0) | 0.0 (10.0) | 0.3 (9.3) | 0.2 (9.7) | - | 0.0 (10.0) | 0.6 (7.7) | 0.1 (9.6) |
| | VAL | 0.0 (0.0) | 0.0 (0.0) | 0.0 (0.0) | 0.0 (0.0) | 0.0 (0.0) | 0.0 (0.0) | - | 0.0 (0.0) | 0.5 (0.0) | 0.1 (0.0) |
| | | 0.0 (0.6) | 0.0 (0.6) | 0.1 (0.8) | 0.0 (0.6) | 0.3 (0.6) | 0.1 (0.6) | 0.0 (0.0) | 0.1 (0.6) | 0.3 (0.6) | |

FIGURE 7M

| Position | Substate | A/235 | A/236 | A/237 | A/239 | A/266 | A/267 | A/325 | A/327 | A/328 | Average |
|---|---|---|---|---|---|---|---|---|---|---|---|
| A/327 | ALA | 0.0 (0.0) | 0.0 (0.0) | 0.0 (0.0) | 0.0 (0.0) | 0.0 (0.0) | 0.0 (0.0) | 0.0 (0.0) | - | 0.0 (0.0) | 0.0 (0.0) |
|  | ARG | 0.5 (0.0) | 0.6 (0.0) | 0.5 (0.0) | 0.4 (0.0) | 0.5 (0.0) | 1.3 (0.1) | 0.9 (0.0) | - | 0.7 (0.0) | 0.7 (0.0) |
|  | ASN | 0.0 (0.0) | 0.2 (0.0) | 0.2 (0.0) | 0.0 (0.0) | 0.3 (0.0) | 1.9 (0.3) | 0.5 (0.0) | - | 0.2 (0.0) | 0.4 (0.0) |
|  | ASP | 0.0 (0.0) | 0.2 (0.0) | 0.0 (0.0) | 0.0 (0.0) | 0.0 (0.0) | 1.1 (0.3) | 0.2 (0.0) | - | 0.0 (0.0) | 0.2 (0.0) |
|  | CYS | 0.0 (0.0) | 0.2 (0.0) | 0.0 (0.0) | 0.0 (0.0) | 0.0 (0.0) | 0.9 (0.3) | 0.3 (0.0) | - | 0.0 (0.0) | 0.2 (0.0) |
|  | GLN | 0.4 (0.0) | 0.7 (0.0) | 0.4 (0.0) | 0.4 (0.0) | 0.3 (0.0) | 1.3 (0.6) | 0.8 (0.0) | - | 0.6 (0.0) | 0.6 (0.1) |
|  | GLU | 0.0 (0.0) | 0.0 (0.0) | 0.0 (0.0) | 0.0 (0.0) | 0.0 (0.0) | 1.6 (0.2) | 0.3 (0.0) | - | 0.0 (0.0) | 0.2 (0.0) |
|  | GLY | 0.0 (0.0) | 0.0 (0.0) | 0.0 (0.0) | 0.0 (0.0) | 0.0 (0.0) | 0.0 (0.0) | 0.0 (0.0) | - | 0.0 (0.0) | 0.0 (0.0) |
|  | HID | 0.0 (1.0) | 0.0 (1.0) | 0.0 (1.0) | 0.0 (1.0) | 0.0 (1.0) | 0.4 (1.5) | 0.0 (1.0) | - | 0.0 (1.0) | 0.1 (1.1) |
|  | HIE | 0.0 (1.0) | 0.0 (1.0) | 0.0 (1.0) | 0.0 (1.0) | 0.0 (1.0) | 0.3 (1.6) | 0.0 (1.0) | - | 0.0 (1.0) | 0.0 (1.1) |
|  | HIP | 0.0 (1.0) | 0.0 (1.0) | 0.0 (1.0) | 0.0 (1.0) | 0.0 (1.0) | 0.4 (1.4) | 0.0 (1.0) | - | 0.0 (1.0) | 0.1 (1.1) |
|  | ILE | 0.0 (0.0) | 0.0 (0.0) | 0.0 (0.0) | 0.0 (0.0) | 0.0 (0.0) | 1.1 (0.5) | 0.0 (0.0) | - | 0.0 (0.0) | 0.1 (0.1) |
|  | LEU | 0.0 (0.0) | 0.0 (0.0) | 0.0 (0.0) | 0.0 (0.0) | 0.0 (0.0) | 0.5 (0.0) | 0.0 (0.0) | - | 0.0 (0.0) | 0.1 (0.0) |
|  | LYS | 0.6 (0.0) | 0.6 (0.0) | 0.4 (0.0) | 0.0 (0.0) | 0.3 (0.0) | 1.4 (0.0) | 0.6 (0.0) | - | 0.4 (0.0) | 0.5 (0.0) |
|  | MET | 0.2 (0.0) | 0.5 (0.0) | 0.0 (0.0) | 0.0 (0.0) | 0.2 (0.0) | 1.1 (0.1) | 0.2 (0.0) | - | 0.0 (0.0) | 0.3 (0.0) |
|  | PHE | 0.0 (2.0) | 0.2 (2.0) | 0.0 (2.0) | 0.0 (2.0) | 0.0 (2.0) | 0.5 (3.0) | 0.0 (2.0) | - | 0.0 (2.0) | 0.1 (2.1) |
|  | SER | 0.0 (0.0) | 0.2 (0.0) | 0.0 (0.0) | 0.0 (0.0) | 0.2 (0.0) | 1.3 (0.0) | 0.4 (0.0) | - | 0.0 (0.0) | 0.3 (0.0) |
|  | THR | 0.0 (0.0) | 0.0 (0.0) | 0.0 (0.0) | 0.0 (0.0) | 0.3 (0.0) | 1.2 (0.3) | 0.4 (0.0) | - | 0.0 (0.0) | 0.2 (0.0) |
|  | TRP | 0.0 (2.0) | 0.0 (2.0) | 0.0 (2.0) | 0.0 (2.0) | 0.0 (2.0) | 0.0 (3.4) | 0.0 (2.0) | - | 0.0 (2.0) | 0.0 (2.2) |
|  | TYR | 0.0 (4.0) | 0.0 (4.0) | 0.0 (4.0) | 0.0 (4.0) | 0.0 (4.0) | 0.4 (4.8) | 0.0 (4.0) | - | 0.0 (4.0) | 0.1 (4.1) |
|  | VAL | 0.0 (0.0) | 0.0 (0.0) | 0.0 (0.0) | 0.0 (0.0) | 0.0 (0.0) | 0.8 (0.2) | 0.0 (0.0) | - | 0.0 (0.0) | 0.1 (0.0) |
| A/328 | ALA | 0.1 (0.5) | 0.2 (0.5) | 0.1 (0.5) | 0.0 (0.5) | 0.1 (0.5) | 0.8 (0.9) | 0.2 (0.5) | 0.0 (0.0) | 0.1 (0.5) | 0.0 (0.0) |
|  | ARG | 0.0 (0.0) | 0.0 (0.0) | 0.0 (0.0) | 0.0 (0.0) | 0.0 (0.0) | 0.0 (0.0) | 0.0 (0.0) | 0.0 (0.0) | - | 0.0 (0.0) |
|  | ASN | 0.0 (0.0) | 0.0 (0.0) | 1.0 (0.0) | 0.0 (0.0) | 0.0 (0.0) | 0.2 (0.0) | 1.0 (0.5) | 0.0 (0.0) | - | 0.3 (0.1) |
|  | ASP | 0.0 (0.0) | 0.0 (0.0) | 0.4 (2.9) | 0.0 (0.0) | 0.4 (0.0) | 0.0 (0.0) | 0.9 (1.6) | 0.3 (0.0) | - | 0.3 (0.6) |
|  | CYS | 0.0 (0.0) | 0.0 (0.0) | 0.7 (0.4) | 0.0 (0.0) | 0.0 (0.0) | 0.0 (0.0) | 0.7 (0.7) | 0.0 (0.0) | - | 0.2 (0.1) |
|  | GLN | 0.3 (0.0) | 0.4 (0.0) | 0.2 (0.0) | 0.0 (0.0) | 0.0 (0.0) | 0.0 (0.0) | 0.6 (0.1) | 0.4 (0.0) | - | 0.1 (0.0) |
|  | GLU | 0.0 (0.0) | 0.4 (0.0) | 0.7 (0.4) | 0.3 (0.0) | 0.8 (0.0) | 0.3 (0.0) | 1.5 (0.3) | 0.4 (0.0) | - | 0.6 (0.1) |
|  | GLY | 0.0 (0.0) | 0.0 (0.0) | 1.0 (0.3) | 0.0 (0.0) | 0.2 (0.0) | 0.3 (0.0) | 1.4 (0.6) | 0.4 (0.0) | - | 0.5 (0.1) |
|  |  | 0.0 (0.0) | 0.0 (0.0) | 0.0 (0.0) | 0.0 (0.0) | 0.0 (0.0) | 0.0 (0.0) | 0.0 (0.0) | 0.0 (0.0) | - | 0.0 (0.0) |

FIGURE 7N

| Position | Substate | A/235 | A/236 | A/237 | A/239 | A/266 | A/267 | A/325 | A/327 | A/328 | Average |
|---|---|---|---|---|---|---|---|---|---|---|---|
| | HID | 0.0 (0.0) | 0.0 (0.0) | 0.6 (2.2) | 0.0 (0.0) | 0.3 (0.1) | 0.0 (0.0) | 1.0 (0.9) | 0.0 (0.0) | - | 0.2 (0.4) |
| | HIE | 0.0 (0.0) | 0.0 (0.0) | 0.7 (2.2) | 0.0 (0.0) | 0.3 (0.1) | 0.0 (0.0) | 1.0 (0.9) | 0.0 (0.0) | - | 0.2 (0.4) |
| | HIP | 0.3 (0.9) | 0.3 (0.9) | 0.4 (2.2) | 0.2 (1.0) | 0.5 (0.8) | 0.3 (0.9) | 1.2 (1.1) | 0.5 (0.8) | - | 0.5 (1.1) |
| | ILE | 0.0 (0.0) | 0.0 (0.0) | 0.8 (0.4) | 0.0 (0.0) | 0.0 (0.0) | 0.0 (0.0) | 0.0 (0.0) | 0.0 (0.0) | - | 0.1 (0.1) |
| | LEU | 0.0 (0.0) | 0.0 (0.0) | 0.4 (0.1) | 0.0 (0.0) | 0.0 (0.0) | 0.0 (0.0) | 0.7 (0.0) | 0.0 (0.0) | - | 0.1 (0.0) |
| | LYS | 0.0 (0.0) | 0.3 (0.0) | 1.3 (0.1) | 0.4 (0.0) | 0.2 (0.0) | 0.0 (0.0) | 0.8 (0.1) | 0.0 (0.0) | - | 0.4 (0.0) |
| | MET | 0.0 (0.0) | 0.0 (0.0) | 0.9 (0.1) | 0.0 (0.0) | 0.0 (0.0) | 0.0 (0.0) | 0.6 (0.0) | 0.0 (0.0) | - | 0.2 (0.0) |
| | PHE | 0.0 (4.0) | 0.0 (4.0) | 0.0 (4.0) | 0.0 (4.0) | 0.0 (4.0) | 0.0 (4.0) | 0.0 (4.0) | 0.0 (4.0) | - | 0.0 (4.0) |
| | SER | 0.0 (0.0) | 0.0 (0.0) | 0.6 (0.0) | 0.0 (0.0) | 0.0 (0.0) | 0.0 (0.0) | 1.1 (0.1) | 0.0 (0.0) | - | 0.2 (0.0) |
| | THR | 0.0 (0.0) | 0.0 (0.0) | 0.7 (0.6) | 0.0 (0.0) | 0.0 (0.0) | 0.0 (0.0) | 0.8 (0.3) | 0.0 (0.0) | - | 0.2 (0.1) |
| | TRP | 0.0 (2.0) | 0.0 (2.0) | 0.8 (7.9) | 0.0 (2.0) | 0.0 (2.0) | 0.0 (2.0) | 0.5 (3.3) | 0.0 (2.0) | - | 0.2 (2.9) |
| | TYR | 0.0 (2.0) | 0.0 (2.0) | 0.0 (2.0) | 0.0 (2.0) | 0.0 (2.0) | 0.0 (2.0) | 0.0 (2.0) | 0.0 (2.0) | - | 0.0 (2.0) |
| | VAL | 0.0 (0.0) | 0.0 (0.0) | 0.4 (0.1) | 0.0 (0.0) | 0.0 (0.0) | 0.0 (0.0) | 0.6 (0.3) | 0.0 (0.0) | - | 0.1 (0.1) |
| | | 0.0 (0.4) | 0.1 (0.4) | 0.5 (1.2) | 0.0 (0.4) | 0.1 (0.4) | 0.1 (0.4) | 0.7 (0.8) | 0.1 (0.4) | 0.0 (0.0) | |

TABLE 3: SHANNON'S ENTROPY AND CLASH COUNT FOR THE INFINITE FRICTION LIMIT ENVIRONMENT

| Position | Substate | A/235 | A/236 | A/237 | A/239 | A/266 | A/267 | A/325 | A/327 | A/328 | Average |
|---|---|---|---|---|---|---|---|---|---|---|---|
| A/235 | ALA | - | 0.0 (0.0) | 0.0 (0.0) | 0.0 (0.0) | 0.0 (0.0) | 0.0 (0.0) | 0.0 (0.0) | 0.0 (0.0) | 0.0 (0.0) | 0.0 (0.0) |
| | ARG | - | 0.7 (0.0) | 0.0 (0.0) | 0.0 (0.0) | 0.0 (0.0) | 0.4 (0.0) | 0.4 (0.0) | 0.4 (0.0) | 0.0 (0.0) | 0.2 (0.0) |
| | ASN | - | 0.5 (0.0) | 0.0 (0.0) | 0.0 (0.0) | 0.0 (0.0) | 0.0 (0.0) | 0.0 (0.0) | 0.0 (0.0) | 0.0 (0.0) | 0.1 (0.0) |
| | ASP | - | 0.3 (0.0) | 0.0 (0.0) | 0.0 (0.0) | 0.0 (0.0) | 0.0 (0.0) | 0.0 (0.0) | 0.0 (0.0) | 0.0 (0.0) | 0.0 (0.0) |
| | CYS | - | 0.0 (0.0) | 0.4 (0.0) | 0.0 (0.0) | 0.0 (0.0) | 0.0 (0.0) | 0.0 (0.0) | 0.0 (0.0) | 0.0 (0.0) | 0.1 (0.0) |
| | GLN | - | 0.2 (0.0) | 0.0 (0.0) | 0.0 (0.0) | 0.0 (0.0) | 0.0 (0.0) | 0.0 (0.0) | 0.0 (0.0) | 0.0 (0.0) | 0.0 (0.0) |
| | GLU | - | 0.0 (0.0) | 0.0 (0.0) | 0.0 (0.0) | 0.0 (0.0) | 0.0 (0.0) | 0.0 (0.0) | 0.3 (0.0) | 0.0 (0.0) | 0.0 (0.0) |
| | GLY | - | 0.0 (0.0) | 0.0 (0.0) | 0.0 (0.0) | 0.0 (0.0) | 0.0 (0.0) | 0.0 (0.0) | 0.0 (0.0) | 0.0 (0.0) | 0.0 (0.0) |
| | HID | - | 0.0 (0.0) | 0.0 (0.0) | 0.0 (0.0) | 0.0 (0.0) | 0.0 (0.0) | 0.0 (0.0) | 0.0 (0.0) | 0.0 (0.0) | 0.0 (0.0) |
| | HIE | - | 0.0 (0.0) | 0.0 (0.0) | 0.0 (0.0) | 0.0 (0.0) | 0.0 (0.0) | 0.0 (0.0) | 0.0 (0.0) | 0.0 (0.0) | 0.0 (0.0) |
| | HIP | - | 0.0 (0.0) | 0.0 (0.0) | 0.0 (0.0) | 0.0 (0.0) | 0.0 (0.0) | 0.0 (0.0) | 0.0 (0.0) | 0.0 (0.0) | 0.0 (0.0) |
| | ILE | - | 0.6 (0.1) | 0.0 (0.0) | 0.0 (0.0) | 0.0 (0.0) | 0.0 (0.0) | 0.0 (0.0) | 0.0 (0.0) | 0.0 (0.0) | 0.1 (0.0) |

FIGURE 7O

| Position | Substrate | A/235 | A/236 | A/237 | A/239 | A/266 | A/267 | A/325 | A/327 | A/328 | Average |
|---|---|---|---|---|---|---|---|---|---|---|---|
| | LEU | - | 0.2 (0.0) | 0.0 (0.0) | 0.0 (0.0) | 0.0 (0.0) | 0.0 (0.0) | 0.0 (0.0) | 0.0 (0.0) | 0.0 (0.0) | 0.0 (0.0) |
| | LYS | - | 0.9 (0.0) | 0.0 (0.0) | 0.2 (0.0) | 0.0 (0.0) | 0.4 (0.0) | 0.4 (0.0) | 0.6 (0.0) | 0.0 (0.0) | 0.3 (0.0) |
| | MET | - | 0.0 (0.0) | 0.0 (0.0) | 0.0 (0.0) | 0.0 (0.0) | 0.0 (0.0) | 0.0 (0.0) | 0.0 (0.0) | 0.0 (0.0) | 0.0 (0.0) |
| | PHE | - | 0.0 (0.0) | 0.0 (0.0) | 0.0 (0.0) | 0.0 (0.0) | 0.0 (0.0) | 0.0 (0.0) | 0.0 (0.0) | 0.0 (0.0) | 0.0 (0.0) |
| | SER | - | 0.5 (0.0) | 0.0 (0.0) | 0.0 (0.0) | 0.0 (0.0) | 0.4 (0.0) | 0.0 (0.0) | 0.5 (0.0) | 0.0 (0.0) | 0.2 (0.0) |
| | THR | - | 0.8 (0.0) | 0.4 (0.0) | 0.0 (0.0) | 0.0 (0.0) | 0.0 (0.0) | 0.0 (0.0) | 0.0 (0.0) | 0.0 (0.0) | 0.1 (0.0) |
| | TRP | - | 0.0 (0.0) | 0.0 (0.0) | 0.0 (0.0) | 0.0 (0.0) | 0.0 (0.0) | 0.0 (0.0) | 0.0 (0.0) | 0.0 (0.0) | 0.0 (0.0) |
| | TYR | - | 0.0 (0.0) | 0.0 (0.0) | 0.0 (0.0) | 0.0 (0.0) | 0.0 (0.0) | 0.0 (0.0) | 0.0 (0.0) | 0.0 (0.0) | 0.0 (0.0) |
| | VAL | - | 0.6 (0.1) | 0.0 (0.0) | 0.0 (0.0) | 0.0 (0.0) | 0.1 (0.0) | 0.0 (0.0) | 0.1 (0.0) | 0.0 (0.0) | 0.1 (0.0) |
| A/236 | ALA | 0.0 (0.0) | 0.3 (0.0) | | | | | | | | |
| | ARG | 0.0 (1.0) | - | 0.0 (1.0) | 0.0 (1.0) | 0.0 (1.0) | 0.0 (1.0) | 0.0 (1.0) | 0.0 (1.0) | 0.0 (1.0) | 0.0 (1.0) |
| | ASN | 0.0 (7.0) | - | 0.0 (7.0) | 0.0 (7.0) | 0.0 (7.0) | 0.0 (7.1) | 0.0 (7.0) | 0.2 (6.9) | 0.0 (7.0) | 0.0 (7.0) |
| | ASP | 0.0 (4.0) | - | 0.0 (4.0) | 0.0 (4.0) | 0.0 (4.0) | 0.0 (4.0) | 0.0 (4.0) | 0.0 (4.0) | 0.0 (4.0) | 0.0 (4.0) |
| | CYS | 0.0 (4.0) | - | 0.0 (4.0) | 0.0 (4.0) | 0.0 (4.0) | 0.0 (4.0) | 0.0 (4.0) | 0.0 (4.0) | 0.0 (4.0) | 0.0 (4.0) |
| | GLN | 0.0 (2.0) | - | 0.0 (2.0) | 0.0 (2.0) | 0.0 (2.0) | 0.0 (2.0) | 0.0 (2.0) | 0.0 (2.0) | 0.0 (2.0) | 0.0 (2.0) |
| | GLU | 0.0 (5.0) | - | 0.0 (5.0) | 0.0 (5.0) | 0.0 (5.0) | 0.0 (5.0) | 0.0 (5.0) | 0.0 (5.0) | 0.0 (5.0) | 0.0 (5.0) |
| | GLY | 0.0 (4.0) | - | 0.0 (4.0) | 0.0 (4.0) | 0.0 (4.0) | 0.0 (4.0) | 0.0 (4.0) | 0.0 (4.0) | 0.0 (4.0) | 0.0 (4.0) |
| | HID | 0.0 (0.0) | - | 0.0 (0.0) | 0.0 (0.0) | 0.0 (0.0) | 0.0 (0.0) | 0.0 (0.0) | 0.0 (0.0) | 0.0 (0.0) | 0.0 (0.0) |
| | HIE | 0.0 (9.0) | - | 0.0 (9.0) | 0.0 (9.0) | 0.0 (9.0) | 0.0 (9.0) | 0.0 (9.0) | 0.0 (9.0) | 0.0 (9.0) | 0.0 (9.0) |
| | HIP | 0.0 (9.0) | - | 0.0 (9.0) | 0.0 (9.0) | 0.0 (9.0) | 0.0 (9.0) | 0.0 (9.0) | 0.0 (9.0) | 0.0 (9.0) | 0.0 (9.0) |
| | ILE | 0.0 (5.0) | - | 0.0 (5.0) | 0.0 (5.0) | 0.0 (5.0) | 0.0 (5.0) | 0.0 (5.0) | 0.0 (5.0) | 0.0 (5.0) | 0.0 (5.0) |
| | LEU | 0.0 (8.0) | - | 0.0 (8.0) | 0.0 (8.0) | 0.0 (8.0) | 0.0 (8.0) | 0.0 (8.0) | 0.0 (8.0) | 0.0 (8.0) | 0.0 (8.0) |
| | LYS | 0.2 (8.7) | - | 0.0 (3.0) | 0.0 (3.0) | 0.0 (3.0) | 0.0 (3.0) | 0.0 (3.0) | 0.0 (3.0) | 0.0 (3.0) | 0.0 (3.7) |
| | MET | 0.2 (3.2) | - | 0.0 (3.0) | 0.0 (3.0) | 0.0 (3.0) | 0.0 (3.0) | 0.0 (3.0) | 0.0 (3.0) | 0.0 (3.0) | 0.0 (3.0) |
| | PHE | 0.0 (12.0) | - | 0.0 (12.0) | 0.0 (12.0) | 0.0 (12.0) | 0.0 (12.0) | 0.0 (12.0) | 0.0 (12.0) | 0.0 (12.0) | 0.0 (12.0) |
| | SER | 0.0 (2.0) | - | 0.0 (2.0) | 0.0 (2.0) | 0.0 (2.0) | 0.0 (2.0) | 0.0 (2.0) | 0.0 (2.0) | 0.0 (2.0) | 0.0 (2.0) |
| | THR | 0.3 (3.0) | - | 0.3 (3.0) | 0.3 (3.0) | 0.0 (3.0) | 0.2 (3.0) | 0.0 (3.0) | 0.2 (3.0) | 0.3 (3.0) | 0.2 (3.0) |
| | TRP | 0.0 (10.0) | - | 0.0 (10.0) | 0.0 (10.0) | 0.0 (10.0) | 0.0 (10.0) | 0.0 (10.0) | 0.0 (10.0) | 0.0 (10.0) | 0.0 (10.0) |
| | TYR | 0.5 (13.0) | - | 0.7 (14.3) | 0.0 (13.0) | 0.0 (13.0) | 0.0 (13.0) | 0.0 (13.0) | 0.0 (13.0) | 0.0 (13.0) | 0.1 (13.2) |

FIGURE 7P

| Position | Substate | A/235 | A/236 | A/237 | A/239 | A/266 | A/267 | A/325 | A/327 | A/328 | Average |
|---|---|---|---|---|---|---|---|---|---|---|---|
|  | VAL | 0.0 (3.0) | - | 0.0 (3.0) | 0.0 (3.0) | 0.0 (3.0) | 0.0 (3.0) | 0.0 (3.0) | 0.0 (3.0) | 0.0 (3.0) | 0.0 (3.0) |
| A/237 |  | 0.1 (5.8) | 0.0 (0.0) | 0.0 (5.6) | 0.0 (5.5) | 0.0 (5.5) | 0.0 (5.5) | 0.0 (5.5) | 0.0 (5.5) | 0.0 (5.5) |  |
|  | ALA | 0.0 (1.0) | 0.0 (1.0) | - | 0.0 (1.0) | 0.0 (1.0) | 0.0 (1.0) | 0.0 (1.0) | 0.0 (1.0) | 0.0 (0.2) | 0.0 (0.9) |
|  | ARG | 0.0 (2.0) | 0.2 (2.3) | - | 0.0 (2.0) | 0.0 (2.0) | 0.0 (2.0) | 0.0 (2.0) | 0.0 (2.0) | 1.0 (0.2) | 0.1 (1.8) |
|  | ASN | 0.0 (1.0) | 0.0 (1.0) | - | 0.0 (1.0) | 0.0 (1.0) | 0.0 (1.0) | 0.0 (1.0) | 0.0 (1.0) | 1.0 (0.6) | 0.1 (1.0) |
|  | ASP | 0.0 (1.0) | 0.0 (1.4) | - | 0.0 (1.0) | 0.0 (1.0) | 0.0 (1.0) | 0.0 (1.0) | 0.0 (1.0) | 0.6 (0.4) | 0.1 (1.0) |
|  | CYS | 0.0 (1.0) | 0.0 (1.1) | - | 0.0 (1.0) | 0.0 (1.0) | 0.0 (1.0) | 0.0 (1.0) | 0.0 (1.0) | 0.0 (0.2) | 0.0 (0.9) |
|  | GLN | 0.0 (2.0) | 0.2 (2.2) | - | 0.0 (2.0) | 0.0 (2.0) | 0.0 (2.0) | 0.0 (2.0) | 0.0 (2.0) | 0.2 (0.0) | 0.0 (1.8) |
|  | GLU | 0.0 (4.0) | 0.0 (4.1) | - | 0.0 (4.0) | 0.0 (4.0) | 0.0 (4.0) | 0.0 (4.0) | 0.0 (4.0) | 0.5 (0.3) | 0.1 (3.6) |
|  | GLY | 0.0 (0.0) | 0.0 (0.0) | - | 0.0 (0.0) | 0.0 (0.0) | 0.0 (0.0) | 0.0 (0.0) | 0.0 (0.0) | 0.0 (0.0) | 0.0 (0.0) |
|  | HID | 0.0 (1.0) | 0.0 (1.0) | - | 0.0 (1.0) | 0.0 (1.0) | 0.0 (1.0) | 0.0 (1.0) | 0.0 (1.0) | 0.4 (0.3) | 0.0 (0.9) |
|  | HIE | 0.0 (1.0) | 0.0 (1.0) | - | 0.0 (1.0) | 0.0 (1.0) | 0.0 (1.0) | 0.0 (1.0) | 0.0 (1.0) | 0.4 (0.3) | 0.0 (0.9) |
|  | HIP | 0.0 (1.0) | 0.0 (1.0) | - | 0.0 (1.0) | 0.0 (1.0) | 0.0 (1.0) | 0.0 (1.0) | 0.0 (1.0) | 0.9 (1.0) | 0.1 (2.8) |
|  | ILE | 0.0 (3.0) | 0.0 (3.0) | - | 0.0 (3.0) | 0.0 (3.0) | 0.0 (3.0) | 0.0 (3.0) | 0.0 (3.0) | 0.7 (0.0) | 0.1 (1.8) |
|  | LEU | 0.0 (2.0) | 0.0 (2.0) | - | 0.0 (2.0) | 0.0 (2.0) | 0.0 (2.0) | 0.0 (2.0) | 0.0 (2.0) | 1.3 (0.3) | 0.2 (1.8) |
|  | LYS | 0.0 (2.0) | 0.0 (2.0) | - | 0.0 (2.0) | 0.0 (2.0) | 0.0 (2.0) | 0.0 (2.0) | 0.0 (2.0) | 0.6 (0.6) | 0.1 (1.8) |
|  | MET | 0.0 (2.0) | 0.0 (2.0) | - | 0.0 (2.0) | 0.0 (2.0) | 0.0 (2.0) | 0.0 (2.0) | 0.0 (2.0) | 0.2 (0.3) | 0.0 (0.9) |
|  | PHE | 0.0 (1.0) | 0.0 (1.0) | - | 0.0 (1.0) | 0.0 (1.0) | 0.0 (1.0) | 0.0 (1.0) | 0.0 (1.0) | 1.1 (0.4) | 0.1 (0.9) |
|  | SER | 0.0 (1.0) | 0.0 (1.0) | - | 0.0 (1.0) | 0.0 (1.0) | 0.0 (1.0) | 0.0 (1.0) | 0.0 (1.0) | 0.6 (0.4) | 0.1 (3.6) |
|  | THR | 0.0 (4.0) | 0.0 (4.0) | - | 0.0 (4.0) | 0.0 (4.0) | 0.0 (4.0) | 0.0 (4.0) | 0.0 (4.0) | 0.4 (0.7) | 0.0 (5.3) |
|  | TRP | 0.0 (6.0) | 0.0 (6.0) | - | 0.0 (6.0) | 0.0 (6.0) | 0.0 (6.0) | 0.0 (6.0) | 0.0 (6.0) | 0.0 (0.3) | 0.0 (0.9) |
|  | TYR | 0.0 (1.0) | 0.0 (1.0) | - | 0.3 (1.0) | 0.0 (1.0) | 0.0 (1.0) | 0.0 (1.0) | 0.0 (1.0) | 0.3 (0.1) | 0.0 (2.6) |
|  | VAL | 0.0 (3.0) | 0.0 (3.1) | - | 0.0 (3.0) | 0.0 (3.0) | 0.0 (3.0) | 0.0 (3.0) | 0.0 (3.0) | 0.5 (0.3) |  |
| A/239 |  | 0.0 (1.9) | 0.0 (2.0) | 0.0 (0.0) | 0.0 (1.9) | 0.0 (1.9) | 0.0 (1.9) | 0.0 (1.9) | 0.0 (1.9) |  |  |
|  | ALA | 0.0 (0.0) | 0.0 (0.0) | 0.0 (0.0) | - | 0.0 (0.0) | 0.0 (0.0) | 0.0 (0.0) | 0.0 (0.0) | 0.0 (0.0) | 0.0 (0.0) |
|  | ARG | 0.0 (0.0) | 0.0 (0.0) | 0.0 (0.0) | - | 0.0 (0.0) | 0.0 (0.0) | 0.0 (0.0) | 0.0 (0.0) | 0.0 (0.0) | 0.0 (0.0) |
|  | ASN | 0.4 (0.0) | 0.4 (0.0) | 0.8 (0.0) | - | 0.3 (0.0) | 0.0 (0.0) | 0.0 (0.0) | 0.0 (0.0) | 0.2 (0.0) | 0.3 (0.0) |
|  | ASP | 0.0 (0.0) | 0.0 (0.0) | 0.2 (0.0) | - | 0.0 (0.0) | 0.0 (0.0) | 0.0 (0.0) | 0.0 (0.0) | 0.0 (0.0) | 0.0 (0.0) |
|  | CYS | 0.0 (0.0) | 0.0 (0.0) | 0.0 (0.0) | - | 0.0 (0.0) | 0.0 (0.0) | 0.0 (0.0) | 0.0 (0.0) | 0.0 (0.0) | 0.0 (0.0) |
|  | GLN | 0.0 (0.0) | 0.3 (0.0) | 0.0 (0.0) | - | 0.0 (0.0) | 0.0 (0.0) | 0.0 (0.0) | 0.0 (0.0) | 0.0 (0.0) | 0.0 (0.0) |

FIGURE 7Q

| Position | Substate | A/235 | A/236 | A/237 | A/239 | A/266 | A/267 | A/325 | A/327 | A/328 | Average |
|---|---|---|---|---|---|---|---|---|---|---|---|
| | GLU | 0.0 (0.0) | 0.0 (0.0) | 0.8 (0.0) | - | 0.0 (0.0) | 0.0 (0.0) | 0.0 (0.0) | 0.0 (0.0) | 0.0 (0.0) | 0.1 (0.0) |
| | GLY | 0.0 (0.0) | 0.0 (0.0) | 0.0 (0.0) | - | 0.0 (0.0) | 0.0 (0.0) | 0.0 (0.0) | 0.0 (0.0) | 0.0 (0.0) | 0.0 (0.0) |
| | HID | 0.0 (0.0) | 0.0 (0.0) | 0.0 (0.0) | - | 0.0 (0.0) | 0.0 (0.0) | 0.0 (0.0) | 0.0 (0.0) | 0.0 (0.0) | 0.0 (0.0) |
| | HIE | 0.0 (0.0) | 0.0 (0.0) | 0.0 (0.0) | - | 0.0 (0.0) | 0.0 (0.0) | 0.0 (0.0) | 0.0 (0.0) | 0.0 (0.0) | 0.0 (0.0) |
| | HIP | 0.0 (0.0) | 0.0 (0.0) | 0.0 (0.0) | - | 0.0 (0.0) | 0.0 (0.0) | 0.0 (0.0) | 0.0 (0.0) | 0.0 (0.0) | 0.0 (0.0) |
| | ILE | 0.0 (0.0) | 0.0 (0.0) | 0.0 (0.0) | - | 0.0 (0.0) | 0.0 (0.0) | 0.0 (0.0) | 0.0 (0.0) | 0.0 (0.0) | 0.0 (0.0) |
| | LEU | 0.0 (0.0) | 0.0 (0.0) | 0.2 (0.0) | - | 0.0 (0.0) | 0.0 (0.0) | 0.0 (0.0) | 0.0 (0.0) | 0.0 (0.0) | 0.0 (0.0) |
| | LYS | 0.0 (0.0) | 0.0 (0.0) | 0.0 (0.0) | - | 0.0 (0.0) | 0.0 (0.0) | 0.0 (0.0) | 0.0 (0.0) | 0.0 (0.0) | 0.0 (0.0) |
| | MET | 0.0 (0.0) | 0.0 (0.0) | 0.7 (0.0) | - | 0.0 (0.0) | 0.0 (0.0) | 0.0 (0.0) | 0.2 (0.0) | 0.0 (0.0) | 0.1 (0.0) |
| | PHE | 0.0 (0.0) | 0.0 (0.0) | 0.2 (0.0) | - | 0.0 (0.0) | 0.0 (0.0) | 0.0 (0.0) | 0.0 (0.0) | 0.0 (0.0) | 0.0 (0.0) |
| | SER | 0.2 (0.0) | 0.5 (0.0) | 0.6 (0.0) | - | 0.7 (0.0) | 0.4 (0.0) | 0.3 (0.0) | 0.5 (0.0) | 0.7 (0.0) | 0.5 (0.0) |
| | THR | 0.0 (0.0) | 0.0 (0.0) | 0.0 (0.0) | - | 0.0 (0.0) | 0.0 (0.0) | 0.0 (0.0) | 0.0 (0.0) | 0.0 (0.0) | 0.0 (0.0) |
| | TRP | 0.0 (0.0) | 0.0 (0.0) | 0.6 (0.1) | - | 0.0 (0.0) | 0.0 (0.0) | 0.0 (0.0) | 0.0 (0.0) | 0.0 (0.0) | 0.1 (0.0) |
| | TYR | 0.0 (1.0) | 0.0 (1.0) | 0.2 (1.0) | - | 0.0 (1.0) | 0.0 (1.0) | 0.0 (1.0) | 0.0 (1.0) | 0.0 (1.0) | 0.0 (1.0) |
| | VAL | 0.0 (0.0) | 0.0 (0.0) | 0.0 (0.0) | 0.0 (0.0) | 0.0 (0.0) | 0.0 (0.0) | 0.0 (0.0) | 0.0 (0.0) | 0.0 (0.0) | 0.0 (0.0) |
| A/266 | ALA | 0.0 (0.0) | 0.1 (0.0) | 0.2 (0.1) | 0.0 (0.0) | - | 0.0 (0.0) | 0.0 (0.0) | 0.0 (0.0) | 0.0 (0.0) | 0.0 (0.0) |
| | ARG | 0.0 (3.0) | 0.0 (3.0) | 0.0 (3.0) | 0.0 (3.0) | - | 0.0 (3.0) | 0.9 (2.8) | 0.0 (3.0) | 0.0 (3.0) | 0.1 (3.0) |
| | ASN | 0.0 (0.0) | 0.0 (0.0) | 0.0 (0.0) | 0.0 (0.0) | - | 0.2 (0.0) | 0.9 (0.0) | 0.0 (0.0) | 0.0 (0.0) | 0.1 (0.0) |
| | ASP | 0.0 (0.0) | 0.0 (0.0) | 0.0 (0.0) | 0.0 (0.0) | - | 0.0 (0.0) | 0.2 (0.0) | 0.0 (0.0) | 0.0 (0.0) | 0.0 (0.0) |
| | CYS | 0.0 (0.0) | 0.0 (0.0) | 0.0 (0.0) | 0.0 (0.0) | - | 0.0 (0.0) | 0.2 (0.0) | 0.0 (0.0) | 0.0 (0.0) | 0.0 (0.0) |
| | GLN | 0.0 (1.0) | 0.0 (1.0) | 0.0 (0.0) | 0.0 (1.0) | - | 0.6 (0.9) | 0.7 (1.0) | 0.0 (1.0) | 0.0 (1.0) | 0.2 (1.0) |
| | GLU | 0.2 (0.0) | 0.3 (0.0) | 0.2 (0.0) | 0.0 (0.0) | - | 0.7 (0.0) | 0.8 (0.0) | 0.4 (0.0) | 0.4 (0.0) | 0.4 (0.0) |
| | GLY | 0.0 (0.0) | 0.0 (0.0) | 0.0 (0.0) | 0.0 (0.0) | - | 0.0 (0.0) | 0.0 (0.0) | 0.0 (0.0) | 0.0 (0.0) | 0.0 (0.0) |
| | HID | 0.0 (5.0) | 0.0 (5.0) | 0.0 (5.0) | 0.0 (5.0) | - | 0.0 (5.0) | 0.0 (5.2) | 0.0 (5.0) | 0.0 (5.0) | 0.0 (5.0) |
| | HIE | 0.0 (5.0) | 0.0 (5.0) | 0.0 (5.0) | 0.0 (5.0) | - | 0.0 (5.0) | 0.2 (5.2) | 0.0 (5.0) | 0.0 (5.0) | 0.0 (5.0) |
| | HIP | 0.0 (5.0) | 0.0 (5.0) | 0.0 (5.0) | 0.0 (5.0) | - | 0.0 (5.0) | 0.2 (5.2) | 0.0 (5.0) | 0.0 (5.0) | 0.0 (5.0) |
| | ILE | 0.0 (0.0) | 0.0 (0.0) | 0.0 (0.0) | 0.0 (0.0) | - | 0.0 (0.0) | 0.0 (0.1) | 0.0 (0.0) | 0.0 (0.0) | 0.0 (0.0) |
| | LEU | 0.0 (0.0) | 0.0 (0.0) | 0.0 (0.0) | 0.0 (0.0) | - | 0.0 (0.0) | 0.7 (0.0) | 0.0 (0.0) | 0.0 (0.0) | 0.1 (0.0) |
| | LYS | 0.0 (0.0) | 0.0 (0.0) | 0.0 (0.0) | 0.0 (0.0) | - | 0.0 (0.0) | 0.0 (0.0) | 0.0 (0.0) | 0.0 (0.0) | 0.0 (0.0) |

FIGURE 7R

| Position | Substrate | A/235 | A/236 | A/237 | A/239 | A/266 | A/267 | A/325 | A/327 | A/328 | Average |
|---|---|---|---|---|---|---|---|---|---|---|---|
| | MET | 0.0 (0.0) | 0.0 (0.0) | 0.0 (0.0) | 0.0 (0.0) | - | 0.2 (0.0) | 0.9 (0.5) | 0.0 (0.0) | 0.0 (0.0) | 0.1 (0.1) |
| | PHE | 0.0 (8.0) | 0.0 (8.0) | 0.0 (8.0) | 0.0 (8.0) | - | 0.0 (8.0) | 0.2 (8.7) | 0.0 (8.0) | 0.0 (8.0) | 0.0 (8.1) |
| | SER | 0.0 (0.0) | 0.0 (0.0) | 0.0 (0.0) | 0.0 (0.0) | - | 0.2 (0.0) | 0.6 (0.0) | 0.0 (0.0) | 0.2 (0.0) | 0.1 (0.0) |
| | THR | 0.0 (0.0) | 0.0 (0.0) | 0.0 (0.0) | 0.0 (0.0) | - | 0.2 (0.0) | 0.6 (0.2) | 0.0 (0.0) | 0.0 (0.0) | 0.1 (0.0) |
| | TRP | 0.0 (7.0) | 0.0 (7.0) | 0.0 (7.0) | 0.0 (7.0) | - | 0.0 (7.0) | 0.0 (10.0) | 0.0 (7.0) | 0.0 (7.0) | 0.0 (7.4) |
| | TYR | 0.0 (17.0) | 0.0 (17.0) | 0.0 (17.0) | 0.0 (17.0) | - | 0.0 (17.0) | 0.5 (17.9) | 0.0 (17.0) | 0.0 (17.0) | 0.1 (17.1) |
| | VAL | 0.0 (0.0) | 0.0 (0.0) | 0.0 (0.0) | 0.0 (0.0) | - | 0.0 (0.0) | 0.7 (0.1) | 0.0 (0.0) | 0.0 (0.0) | 0.1 (0.0) |
| A/267 | | 0.0 (2.4) | 0.0 (2.4) | 0.0 (2.4) | 0.0 (2.4) | 0.0 (0.0) | 0.1 (2.4) | 0.4 (2.7) | 0.0 (2.4) | 0.0 (2.4) | |
| | ALA | 0.0 (0.0) | 0.0 (0.0) | 0.0 (0.0) | 0.0 (0.0) | 0.0 (0.0) | - | 0.0 (0.0) | 0.0 (0.0) | 0.0 (0.0) | 0.0 (0.0) |
| | ARG | 0.0 (0.0) | 0.0 (0.0) | 0.0 (0.0) | 0.0 (0.0) | 0.0 (0.0) | - | 0.0 (0.0) | 0.4 (0.0) | 0.0 (0.0) | 0.0 (0.0) |
| | ASN | 0.0 (0.0) | 0.0 (0.0) | 0.0 (0.0) | 0.0 (0.0) | 0.0 (0.0) | - | 0.0 (0.0) | 0.6 (0.0) | 0.0 (0.0) | 0.1 (0.0) |
| | ASP | 0.0 (0.0) | 0.0 (0.0) | 0.0 (0.0) | 0.0 (0.0) | 0.2 (0.0) | - | 0.5 (0.0) | 0.4 (0.0) | 0.2 (0.0) | 0.2 (0.0) |
| | CYS | 0.0 (0.0) | 0.0 (0.0) | 0.0 (0.0) | 0.0 (0.0) | 0.0 (0.0) | - | 0.0 (0.0) | 0.0 (0.0) | 0.0 (0.0) | 0.0 (0.0) |
| | GLN | 0.3 (0.0) | 0.9 (0.0) | 0.5 (0.0) | 0.7 (0.0) | 0.7 (0.0) | - | 0.8 (0.0) | 1.2 (0.0) | 0.8 (0.0) | 0.7 (0.0) |
| | GLU | 0.0 (0.0) | 0.3 (0.0) | 0.0 (0.0) | 0.0 (0.0) | 0.4 (0.0) | - | 1.0 (0.1) | 1.3 (0.5) | 0.2 (0.0) | 0.4 (0.1) |
| | GLY | 0.0 (0.0) | 0.0 (0.0) | 0.0 (0.0) | 0.0 (0.0) | 0.0 (0.0) | - | 0.0 (0.0) | 0.0 (0.0) | 0.0 (0.0) | 0.0 (0.0) |
| | HID | 0.0 (0.0) | 0.2 (0.0) | 0.0 (0.0) | 0.0 (0.0) | 0.3 (0.0) | - | 0.2 (0.0) | 1.0 (1.3) | 0.0 (0.0) | 0.2 (0.2) |
| | HIE | 0.2 (0.0) | 0.3 (0.0) | 0.0 (0.0) | 0.0 (0.0) | 0.3 (0.0) | - | 0.2 (0.0) | 1.0 (1.4) | 0.0 (0.0) | 0.3 (0.2) |
| | HIP | 0.0 (0.0) | 0.0 (0.0) | 0.0 (0.0) | 0.0 (0.0) | 0.0 (0.0) | - | 0.2 (0.0) | 1.1 (1.4) | 0.0 (0.0) | 0.2 (0.2) |
| | ILE | 0.0 (0.0) | 0.0 (0.0) | 0.0 (0.0) | 0.0 (0.0) | 0.5 (0.0) | - | 0.8 (0.0) | 0.3 (0.0) | 0.0 (0.0) | 0.2 (0.0) |
| | LEU | 0.0 (0.0) | 0.0 (0.0) | 0.0 (0.0) | 0.0 (0.0) | 0.0 (0.0) | - | 0.0 (0.0) | 0.7 (0.0) | 0.0 (0.0) | 0.1 (0.0) |
| | LYS | 0.0 (0.0) | 0.0 (0.0) | 0.0 (0.0) | 0.0 (0.0) | 0.0 (0.0) | - | 0.0 (0.0) | 0.8 (0.1) | 0.0 (0.0) | 0.1 (0.0) |
| | MET | 0.6 (0.0) | 0.8 (0.0) | 0.0 (0.0) | 0.5 (0.0) | 0.6 (0.0) | - | 0.3 (0.0) | 0.7 (0.0) | 0.5 (0.0) | 0.6 (0.0) |
| | PHE | 0.0 (0.0) | 0.0 (0.0) | 0.4 (0.0) | 0.0 (0.0) | 0.0 (0.0) | - | 0.2 (0.0) | 0.6 (2.4) | 0.0 (0.0) | 0.1 (0.3) |
| | SER | 0.4 (0.0) | 0.8 (0.0) | 0.8 (0.0) | 0.2 (0.0) | 0.9 (0.0) | - | 0.8 (0.0) | 1.0 (0.0) | 0.8 (0.0) | 0.7 (0.0) |
| | THR | 0.0 (0.0) | 0.0 (0.0) | 0.0 (0.0) | 0.0 (0.0) | 0.2 (0.0) | - | 0.2 (0.1) | 0.2 (0.0) | 0.0 (0.0) | 0.1 (0.0) |
| | TRP | 0.0 (0.0) | 0.0 (0.0) | 0.0 (0.0) | 0.0 (0.0) | 0.0 (0.0) | - | 0.0 (0.0) | 0.5 (2.3) | 0.0 (0.0) | 0.1 (0.3) |
| | TYR | 0.0 (2.0) | 0.0 (2.1) | 0.0 (2.0) | 0.0 (2.0) | 0.0 (2.0) | - | 0.0 (2.0) | 0.4 (3.6) | 0.0 (2.0) | 0.1 (2.2) |
| | VAL | 0.0 (0.0) | 0.0 (0.0) | 0.0 (0.0) | 0.0 (0.0) | 0.0 (0.0) | 0.0 (0.0) | 0.4 (0.0) | 0.0 (0.0) | 0.0 (0.0) | 0.1 (0.0) |
| | | 0.1 (0.1) | 0.2 (0.1) | 0.1 (0.1) | 0.1 (0.1) | 0.2 (0.1) | 0.0 (0.0) | 0.3 (0.1) | 0.6 (0.6) | 0.1 (0.1) | |

FIGURE 7S

| Position | Substate | A/235 | A/236 | A/237 | A/239 | A/266 | A/267 | A/325 | A/327 | A/328 | Average |
|---|---|---|---|---|---|---|---|---|---|---|---|
| A/325 | ALA | 0.0 (0.0) | 0.0 (0.0) | 0.0 (0.0) | 0.0 (0.0) | 0.0 (0.1) | 0.0 (0.0) | - | 0.0 (0.0) | 0.0 (0.1) | 0.0 (0.0) |
| | ARG | 0.0 (6.0) | 0.0 (6.0) | 0.0 (6.0) | 0.0 (6.0) | 0.7 (3.9) | 0.4 (5.6) | - | 0.0 (6.0) | 0.9 (1.7) | 0.2 (5.2) |
| | ASN | 0.0 (0.0) | 0.0 (0.0) | 0.0 (0.0) | 0.0 (0.0) | 0.8 (0.2) | 0.0 (0.0) | - | 0.2 (0.0) | 0.5 (0.1) | 0.2 (0.0) |
| | ASP | 0.0 (0.0) | 0.0 (0.0) | 0.0 (0.0) | 0.0 (0.0) | 1.0 (0.5) | 0.0 (0.0) | - | 0.5 (0.0) | 1.2 (0.2) | 0.3 (0.1) |
| | CYS | 0.0 (0.0) | 0.0 (0.0) | 0.0 (0.0) | 0.0 (0.0) | 0.3 (0.2) | 0.0 (0.0) | - | 0.0 (0.0) | 0.6 (0.1) | 0.1 (0.0) |
| | GLN | 0.0 (5.0) | 0.0 (5.0) | 0.0 (5.0) | 0.0 (5.0) | 0.5 (4.8) | 0.0 (5.0) | - | 0.4 (4.8) | 1.4 (1.7) | 0.3 (4.5) |
| | GLU | 0.0 (0.0) | 0.0 (0.0) | 0.0 (0.0) | 0.0 (0.0) | 0.5 (0.6) | 0.0 (0.0) | - | 0.2 (0.1) | 0.8 (1.0) | 0.2 (0.2) |
| | GLY | 0.0 (0.0) | 0.0 (0.0) | 0.0 (0.0) | 0.0 (0.0) | 0.0 (0.0) | 0.0 (0.0) | - | 0.0 (0.0) | 0.0 (0.0) | 0.0 (0.0) |
| | HID | 0.0 (1.0) | 0.0 (1.0) | 0.0 (1.0) | 0.0 (1.0) | 0.4 (2.0) | 0.2 (1.5) | - | 0.0 (1.0) | 0.2 (0.2) | 0.1 (1.1) |
| | HIE | 0.0 (1.0) | 0.0 (1.0) | 0.0 (1.0) | 0.0 (1.0) | 0.4 (2.0) | 0.0 (1.0) | - | 0.0 (1.0) | 0.3 (0.2) | 0.1 (1.0) |
| | HIP | 0.0 (1.0) | 0.0 (1.0) | 0.0 (1.0) | 0.0 (1.0) | 0.4 (2.0) | 0.0 (1.0) | - | 0.0 (1.0) | 0.2 (0.2) | 0.1 (1.0) |
| | ILE | 0.0 (0.0) | 0.0 (0.0) | 0.0 (0.0) | 0.0 (0.0) | 0.5 (0.4) | 0.0 (0.0) | - | 0.0 (0.0) | 0.0 (0.0) | 0.1 (0.0) |
| | LEU | 0.0 (1.0) | 0.0 (1.0) | 0.0 (1.0) | 0.0 (1.0) | 0.8 (1.2) | 0.2 (1.0) | - | 0.4 (1.0) | 0.8 (1.0) | 0.2 (1.0) |
| | LYS | 0.0 (1.0) | 0.0 (1.0) | 0.0 (1.0) | 0.0 (1.0) | 1.1 (1.6) | 0.3 (0.1) | - | 0.4 (1.0) | 0.7 (0.3) | 0.3 (0.9) |
| | MET | 0.0 (0.0) | 0.0 (0.0) | 0.0 (0.0) | 0.0 (0.0) | 0.5 (0.5) | 0.2 (0.0) | - | 0.0 (0.0) | 0.7 (0.4) | 0.2 (0.1) |
| | PHE | 0.0 (5.0) | 0.0 (5.0) | 0.0 (5.0) | 0.0 (5.0) | 0.2 (5.8) | 0.0 (5.0) | - | 0.0 (5.0) | 0.3 (1.5) | 0.1 (4.7) |
| | SER | 0.0 (0.0) | 0.0 (0.0) | 0.0 (0.0) | 0.0 (0.0) | 0.8 (0.1) | 0.3 (0.0) | - | 0.2 (0.0) | 0.6 (0.1) | 0.2 (0.0) |
| | THR | 0.0 (0.0) | 0.2 (0.0) | 0.3 (0.0) | 0.3 (0.0) | 0.9 (0.2) | 0.2 (0.0) | - | 0.2 (0.0) | 1.0 (0.0) | 0.4 (0.0) |
| | TRP | 0.0 (17.0) | 0.0 (17.0) | 0.0 (17.0) | 0.0 (17.0) | 0.0 (15.7) | 0.0 (17.0) | - | 0.2 (16.6) | 0.3 (3.6) | 0.1 (15.1) |
| | TYR | 0.0 (10.0) | 0.0 (10.0) | 0.0 (10.0) | 0.0 (10.0) | 0.0 (10.9) | 0.0 (10.0) | - | 0.0 (10.0) | 0.3 (9.5) | 0.0 (10.0) |
| | VAL | 0.0 (0.0) | 0.0 (0.0) | 0.0 (0.0) | 0.0 (0.0) | 0.4 (0.2) | 0.0 (0.0) | - | 0.0 (0.0) | 0.5 (0.0) | 0.1 (0.0) |
| A/327 | ALA | 0.0 (2.3) | 0.0 (2.3) | 0.0 (2.3) | 0.0 (2.3) | 0.5 (2.5) | 0.1 (2.3) | 0.0 (0.0) | 0.1 (2.3) | 0.5 (1.0) | 0.0 (0.0) |
| | ARG | 0.0 (0.0) | 0.0 (0.0) | 0.0 (0.0) | 0.0 (0.0) | 0.0 (0.0) | 0.0 (0.0) | 0.0 (0.0) | - | 0.0 (0.0) | 0.0 (0.0) |
| | ASN | 0.3 (0.0) | 0.0 (0.0) | 0.0 (0.0) | 0.0 (0.0) | 0.0 (0.0) | 1.6 (0.2) | 0.0 (0.0) | - | 0.0 (0.0) | 0.3 (0.0) |
| | ASP | 0.0 (0.0) | 0.2 (0.0) | 0.2 (0.0) | 0.0 (0.0) | 0.0 (0.0) | 1.3 (0.2) | 0.3 (0.0) | - | 0.3 (0.0) | 0.3 (0.0) |
| | CYS | 0.0 (0.0) | 0.0 (0.0) | 0.0 (0.0) | 0.0 (0.0) | 0.0 (0.0) | 0.8 (0.8) | 0.2 (0.0) | - | 0.0 (0.0) | 0.1 (0.1) |
| | GLN | 0.0 (0.0) | 0.0 (0.0) | 0.0 (0.0) | 0.0 (0.0) | 0.0 (0.0) | 0.7 (0.3) | 0.0 (0.0) | - | 0.0 (0.0) | 0.1 (0.0) |
| | GLU | 0.0 (0.0) | 0.0 (0.0) | 0.0 (0.0) | 0.0 (0.0) | 0.0 (0.0) | 1.1 (0.6) | 0.0 (0.0) | - | 0.0 (0.0) | 0.1 (0.1) |
| | GLY | 0.0 (0.0) | 0.0 (0.0) | 0.0 (0.0) | 0.0 (0.0) | 0.0 (0.0) | 1.2 (0.2) | 0.0 (0.0) | - | 0.0 (0.0) | 0.0 (0.0) |

FIGURE 7T

| Position | Substate | A/235 | A/236 | A/237 | A/239 | A/266 | A/267 | A/325 | A/327 | A/328 | Average |
|---|---|---|---|---|---|---|---|---|---|---|---|
| | HID | 0.0 (1.0) | 0.0 (1.0) | 0.0 (1.0) | 0.0 (1.0) | 0.0 (1.0) | 0.5 (1.6) | 0.0 (1.0) | - | 0.0 (1.0) | 0.1 (1.1) |
| | HIE | 0.0 (1.0) | 0.0 (1.0) | 0.0 (1.0) | 0.0 (1.0) | 0.0 (1.0) | 0.5 (1.6) | 0.0 (1.0) | - | 0.0 (1.0) | 0.1 (1.1) |
| | HIP | 0.0 (1.0) | 0.0 (1.0) | 0.0 (1.0) | 0.0 (1.0) | 0.0 (1.0) | 0.5 (1.7) | 0.0 (1.0) | - | 0.0 (1.0) | 0.1 (1.1) |
| | ILE | 0.0 (0.0) | 0.0 (0.0) | 0.0 (0.0) | 0.0 (0.0) | 0.0 (0.0) | 0.8 (0.8) | 0.0 (0.0) | - | 0.0 (0.0) | 0.1 (0.1) |
| | LEU | 0.0 (1.0) | 0.0 (1.0) | 0.0 (1.0) | 0.0 (1.0) | 0.0 (1.0) | 0.6 (1.0) | 0.0 (1.0) | - | 0.0 (1.0) | 0.1 (1.0) |
| | LYS | 0.3 (0.0) | 0.5 (0.0) | 0.5 (0.0) | 0.3 (0.0) | 0.8 (0.0) | 1.7 (0.2) | 0.8 (0.0) | - | 0.4 (0.0) | 0.7 (0.0) |
| | MET | 0.2 (0.0) | 0.0 (0.0) | 0.0 (0.0) | 0.0 (0.0) | 0.0 (0.0) | 1.3 (0.4) | 0.5 (0.0) | - | 0.0 (0.0) | 0.2 (0.0) |
| | PHE | 0.0 (2.0) | 0.0 (2.0) | 0.0 (2.0) | 0.0 (2.0) | 0.0 (2.0) | 0.6 (3.0) | 0.0 (2.0) | - | 0.0 (2.0) | 0.1 (2.1) |
| | SER | 0.4 (0.0) | 0.6 (0.0) | 0.9 (0.0) | 0.0 (0.0) | 0.4 (0.0) | 1.4 (0.1) | 0.6 (0.0) | - | 0.8 (0.0) | 0.6 (0.0) |
| | THR | 0.2 (0.0) | 0.0 (0.0) | 0.0 (2.0) | 0.0 (0.0) | 0.2 (0.0) | 1.2 (0.4) | 0.4 (0.0) | - | 0.0 (0.0) | 0.2 (0.0) |
| | TRP | 0.0 (2.0) | 0.0 (2.0) | 0.0 (2.0) | 0.0 (2.0) | 0.0 (2.0) | 0.2 (3.1) | 0.0 (2.0) | - | 0.0 (2.0) | 0.0 (2.1) |
| | TYR | 0.0 (4.0) | 0.0 (4.0) | 0.0 (4.0) | 0.0 (4.0) | 0.0 (4.0) | 0.3 (5.0) | 0.0 (4.0) | - | 0.0 (4.0) | 0.0 (4.1) |
| | VAL | 0.0 (0.0) | 0.0 (0.0) | 0.0 (0.0) | 0.0 (0.0) | 0.0 (0.0) | 0.5 (0.4) | 0.0 (0.0) | - | 0.0 (0.0) | 0.1 (0.0) |
| A/328 | ALA | 0.1 (0.6) | 0.1 (0.6) | 0.1 (0.6) | 0.0 (0.6) | 0.1 (0.6) | 0.8 (1.0) | 0.1 (0.6) | 0.0 (0.0) | 0.1 (0.6) | |
| | ARG | 0.0 (0.0) | 0.0 (0.0) | 0.0 (0.0) | 0.0 (0.0) | 0.0 (0.0) | 0.0 (0.0) | 0.0 (0.0) | 0.0 (0.0) | - | 0.0 (0.0) |
| | ASN | 0.3 (0.0) | 0.5 (0.0) | 0.8 (0.9) | 0.0 (0.0) | 0.4 (0.0) | 0.0 (0.0) | 0.6 (0.3) | 0.0 (0.0) | - | 0.2 (0.1) |
| | ASP | 0.0 (0.0) | 0.0 (0.0) | 0.4 (2.8) | 0.5 (0.0) | 0.0 (0.0) | 0.7 (0.0) | 1.7 (1.6) | 0.9 (0.0) | - | 0.7 (0.5) |
| | CYS | 0.0 (0.0) | 0.0 (0.0) | 0.9 (0.4) | 0.0 (0.0) | 0.0 (0.0) | 0.0 (0.0) | 1.4 (0.9) | 0.0 (0.0) | - | 0.3 (0.2) |
| | GLN | 0.0 (0.0) | 0.0 (0.0) | 0.2 (0.0) | 0.0 (0.0) | 0.0 (0.0) | 0.0 (0.0) | 0.7 (0.0) | 0.0 (0.0) | - | 0.1 (0.0) |
| | GLU | 0.0 (0.0) | 0.0 (0.0) | 0.9 (0.6) | 0.0 (0.0) | 0.0 (0.0) | 0.0 (0.0) | 1.3 (0.3) | 0.0 (0.0) | - | 0.3 (0.1) |
| | GLY | 0.0 (0.0) | 0.0 (0.0) | 0.7 (1.3) | 0.0 (0.0) | 0.0 (0.0) | 0.0 (0.0) | 1.1 (0.9) | 0.0 (0.0) | - | 0.2 (0.3) |
| | HID | 0.0 (0.0) | 0.0 (0.0) | 0.0 (0.0) | 0.0 (0.0) | 0.0 (0.0) | 0.0 (0.0) | 0.0 (0.0) | 0.0 (0.0) | - | 0.0 (0.0) |
| | HIE | 0.0 (0.0) | 0.0 (0.0) | 0.8 (2.4) | 0.0 (0.0) | 0.0 (0.0) | 0.0 (0.0) | 0.9 (0.9) | 0.0 (0.0) | - | 0.2 (0.4) |
| | HIP | 0.0 (0.0) | 0.0 (0.0) | 0.8 (2.2) | 0.0 (0.0) | 0.0 (0.0) | 0.0 (0.0) | 1.0 (1.0) | 0.0 (0.0) | - | 0.2 (0.4) |
| | ILE | 0.0 (0.0) | 0.0 (0.0) | 0.8 (0.0) | 0.0 (0.0) | 0.0 (0.0) | 0.0 (0.0) | 0.8 (0.9) | 0.0 (0.0) | - | 0.2 (0.4) |
| | LEU | 0.0 (0.0) | 0.0 (0.0) | 0.6 (0.3) | 0.0 (0.0) | 0.0 (0.0) | 0.0 (0.0) | 0.5 (0.3) | 0.0 (0.0) | - | 0.1 (0.1) |
| | LYS | 0.0 (0.0) | 0.0 (0.0) | 0.7 (0.0) | 0.0 (0.0) | 0.0 (0.0) | 0.0 (0.0) | 1.0 (0.0) | 0.0 (0.0) | - | 0.2 (0.0) |
| | MET | 0.0 (0.0) | 0.0 (0.0) | 0.5 (0.0) | 0.0 (0.0) | 0.0 (0.0) | 0.0 (0.0) | 1.1 (0.2) | 0.0 (0.0) | - | 0.2 (0.0) |
| | PHE | 0.0 (4.0) | 0.0 (4.0) | 0.0 (0.0) | 0.0 (4.0) | 0.0 (4.0) | 0.0 (4.0) | 0.0 (4.0) | 0.0 (4.0) | - | 0.0 (4.0) |

FIGURE 7U

| Position | Substrate | A/235 | A/236 | A/237 | A/239 | A/266 | A/267 | A/325 | A/327 | A/328 | Average |
|---|---|---|---|---|---|---|---|---|---|---|---|
| | SER | 0.0 (0.0) | 0.0 (0.0) | 1.0 (0.0) | 0.2 (0.0) | 0.0 (0.0) | 0.0 (0.0) | 1.2 (0.0) | 0.4 (0.0) | - | 0.3 (0.0) |
| | THR | 0.0 (0.0) | 0.2 (0.0) | 0.7 (0.5) | 0.0 (0.0) | 0.3 (0.0) | 0.3 (0.0) | 1.1 (0.4) | 0.3 (0.0) | - | 0.4 (0.1) |
| | TRP | 0.0 (4.7) | 0.0 (4.7) | 0.5 (7.8) | 0.0 (4.7) | 0.0 (4.8) | 0.0 (4.7) | 0.7 (8.2) | 0.0 (4.7) | - | 0.1 (5.5) |
| | TYR | 0.0 (2.0) | 0.0 (2.0) | 0.0 (2.0) | 0.0 (2.0) | 0.0 (2.0) | 0.0 (2.0) | 0.0 (2.0) | 0.0 (2.0) | - | 0.0 (2.0) |
| | VAL | 0.0 (0.0) | 0.0 (0.0) | 0.4 (0.1) | 0.0 (0.0) | 0.0 (0.0) | 0.0 (0.0) | 0.6 (0.4) | 0.0 (0.0) | - | 0.1 (0.1) |
| | | 0.0 (0.5) | 0.0 (0.5) | 0.5 (1.3) | 0.0 (0.5) | 0.0 (0.5) | 0.0 (0.5) | 0.8 (1.1) | 0.1 (0.5) | 0.0 (0.0) | |

US 10,002,231 B2

SIMPLIFYING RESIDUE RELATIONSHIPS IN PROTEIN DESIGN

CROSS-REFERENCE TO RELATED APPLICATIONS

This application claims priority to U.S. Patent Application 61/388,208, filed Sep. 30, 2010, which is incorporated by reference.

TECHNICAL FIELD

The invention resides in the field of computational protein structure study and design.

BACKGROUND

A number of methods are known for calculating protein structure and dynamics. For a review on the application of energy functions, see Pokala N and Handel T M, "Energy functions for protein design: adjustment with protein-protein complex affinities, models for the unfolded state, and negative design of solubility and specificity", J Mol. Biol., 2005 Mar. 18, 347(1): 203-27. For a discussion of the concept of developing a library of rotamers for use in protein design, see Lovell S C, Word J M, Richardson J S and Richardson D C, "The penultimate rotamer library", Proteins, 2000 Aug. 15, 40(3): 389-408. To appreciate the efforts made to develop shortcuts in computational requirements, namely on the topic of hot spot prediction & correlated residues, see Tuncbag N, Salman F S, Keskin O and Gursoy A, "Analysis and network representation of hotspots in protein interfaces using minimum cut trees", Proteins, 2010 Aug. 1, 78(10): 2283-94.

Computational protein chemistry necessarily involves many routines and shortcuts to allow limited computer resources to address complex calculations. One property of proteins, known to be useful in protein design, but difficult and expensive to understand, is the coupling of structural units pertaining to proteins, such as side-chains, backbone and ligands. In particular, mutations imply a structural change at one location of the protein that through aforementioned couplings can lead to significant structural and physical changes at a site remote to the site of mutation.

The complexity of the interactions within and between proteins necessarily means that these couplings are hard to determine and approximate computational methods have been shown to be one way to effectively approach the subject. The methods described herein address these and other problems in the field.

SUMMARY OF INVENTION

Provided herein are various coupled residue methods, referred to individually or collectively as "FastPair", which determine either positions in a polypeptide (or protein) that are likely to be intrinsically coupled, irrespective of the amino acid type at that position, or the coupling between specific amino acids in the polypeptide sequence. The methods of the invention accomplish this without the user having to run full computational chemistry calculations.

FastPair optimizes a given subset of residues in a constrained environment and from that calculation derives information on the degree of coupling of that subset of residues. The constraint placed on the environment leads to a significant reduction of the computational effort vis-à-vis the calculation to optimize the given subset of residues in an environment allowed to relax to the optimization of the pair of residues. The latter, more expensive type of calculation is referred to as a "full packing" or "traditional packing" calculation in the remainder of this document. For an overview of traditional packing methods, see Lippow SM and Tidor B, "Progress in computational protein design", Current Opinion in Biotechnology, 2007, 18: 305-311. The constrained environment in FastPair might imply a loss of accuracy compared to the full packing calculation, yet experiments have shown that the reduction of accuracy is small compared to the significant gain in computational speed.

Consequently, with FastPair, information on couplings between subsets of residues can be obtained for a more complete set of residues in a protein than with the full packing calculation using the same amount of computational resources.

Generally, there is provided a method of determining the relationship between two or more residues in a peptide, the method comprising the steps of: taking a set of two or more residues, R; applying theoretical perturbations, P, to the residues; monitoring the dependence of the properties of residues forming a subset $r_2$ of R on the properties of residues forming a subset $r_1$ of R, in some idealized or constrained environment, E; and measuring the dependence of the properties of the residues relative to each other. In any embodiment described herein, the sets $r_1$ and $r_2$ may contain common elements. In some embodiments, the properties of one or both of said residue subsets are monitored for conformance to predetermined criteria. In some embodiments, the relative dependence between the properties of the residues is used to draw conclusions pertaining to the coupling of said residues. In some embodiments, relations between structural perturbations are used to optimize or in some way alter the properties of a protein at locations other than the site of structural modification.

FastPair can be used to measure the effect of system perturbations on protein-ligand binding affinity, protein-protein affinity, protein stability and side-chain coupling. The system can then be re-engineered to provide proteins that are improved in these respects.

Accordingly, in one aspect, the invention provides a computer implemented method of determining changes in a first set of residues $r_1$ due to changes in a second set of residues $r_2$ in a protein system comprising one or more proteins comprising $r_1$ and $r_2$, the method comprising: (a) applying a perturbation selected from a first set of perturbations $P_1=\{p_1, \ldots, p_n\}$ to $r_2$, wherein n is a user-defined number of perturbations; (b) optimizing a quality function Q by modifying one or more properties of $r_1$ and $r_2$ in a constrained environment in which all degrees of freedom of the system except those directly involved in the potential coupling between $r_1$ and $r_2$ are removed; (c) applying a measure M to a subset of $r_1$ thereby providing a property value v; and (d) repeating steps (a) through (c), each time applying a different perturbation selected from the perturbations $P_1$ until all perturbations in $P_1$ have been applied, thereby providing a set of property values $V_1=\{v_1, \ldots, v_n\}$. In exemplary embodiments, the method is performed on a computer system comprising (1) a clock, (2) a memory, and (3) a processor and each step of the method is performed utilizing the processor.

BRIEF DESCRIPTION OF THE DRAWINGS

FIG. 3A and FIG. 3B show a tabulation of the data validating the accuracy of the FastPair method in selecting optimal rotamers evaluated on a pair basis. The first number in each cell is the pair success rate in the full background limit, the second number is the success rate in the zero background limit, and the third number is the success rate in the mixed background limit.

FIG. 4(a) shows results in the full background limit, (b) results in the zero background limit, and (c) results in the mixed background limit.

FIG. 5A-FIG. 5C shows graphical representation of distributions of a site coupling metric as computed by the FastPair method in the (a) full background limit (b) mixed background limit and (c) the zero background limit.

FIG. 6A-FIG. 6C shows graphical representations of pair entropy as computed by the FastPair method in the (a) full background limit (b) mixed background limit and (c) the zero background limit.

FIG. 7A to FIG. 7U show Tables 1, 2 and 3, which tabulate Shannon entropy and heavy atom clash counts using the zero, mixed and full ("infinite friction limit") background, respectively. HID refers to the H-Nδ tautomer of the histidine side-chain, HIE the H-Nε tautomer, and HIP the doubly protonated tautomer.

DESCRIPTION OF EMBODIMENTS

Figure 1:
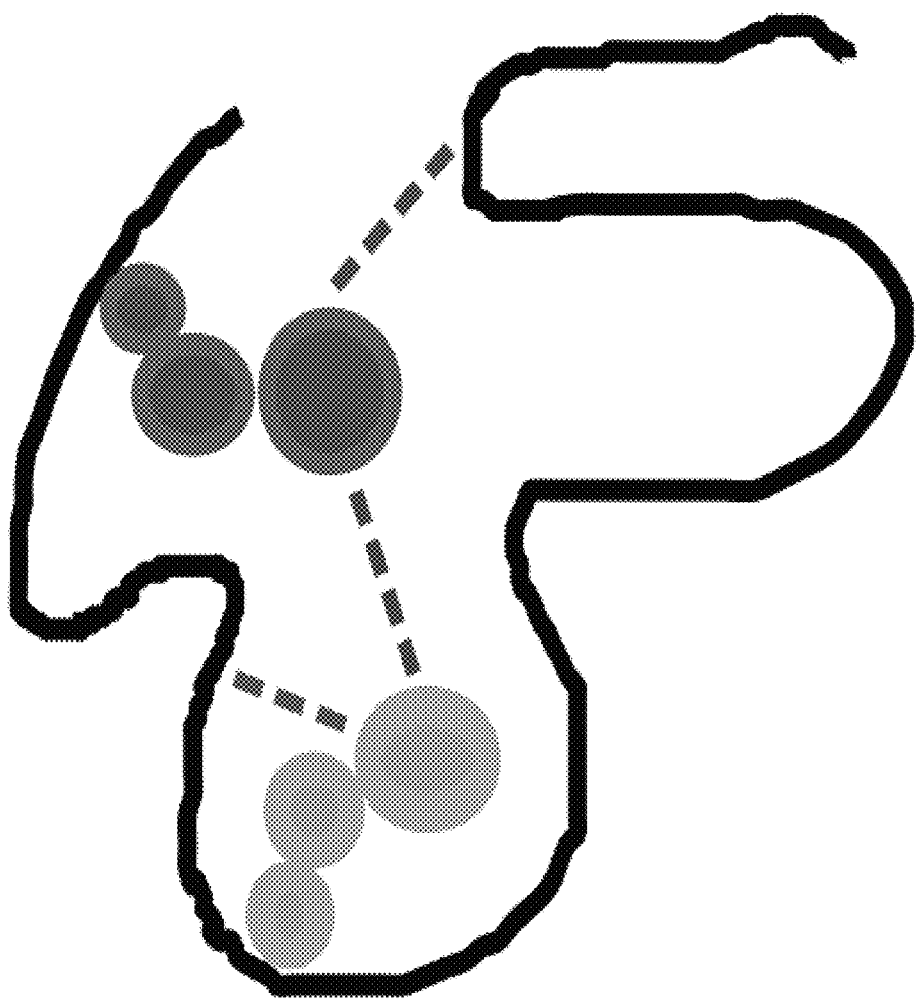
FIG. 1 shows an artist's rendition of two residues (dark gray and light gray circles) in a protein to show context. The pair-wise interaction between the two residues in question is shown as a dashed line. Other dashed lines represent the interactions between the residues and their environment. In embodiments of the methods described herein, optimization of the side-chain conformation takes all interactions in FIG. 1 into account. Environmental influences in some cases might overwhelm the coupling between two residues that would otherwise be strong in the absence of environmental influences.

In one aspect, the invention provides a method of determining changes in a first set of residues $r_1$ due to changes in a second set of residues $r_2$ in a protein system comprising one or more proteins comprising $r_1$ and $r_2$, the method comprising (a) applying a perturbation selected from a set of perturbations $P_1=\{p_1, \ldots, p_n\}$ to $r_2$, wherein n is a user-defined number of perturbations; (b) optimizing a quality function Q by modifying one or more properties of $r_1$ and $r_2$ in a constrained environment in which all degrees of freedom except those directly involved in the potential coupling between $r_1$ and $r_2$ are removed; (c) applying a measure M to a subset of $r_1$, thereby providing a property value v; and (d) repeating steps (a) through (c), each time applying a different perturbation selected from the perturbations $P_1$ until all perturbations in $P_1$ have been applied, thereby providing a set of property values $V_1=\{v_1, \ldots, v_n\}$. In exemplary embodiments, the method is performed on a computer programmed to perform the steps of the method. In exemplary embodiments, the method is performed on a computer system comprising (1) a clock, (2) a memory, and (3) a processor and each step of the method is performed utilizing the processor.

The protein system studied can comprise one or more proteins, each comprising a plurality of residues or amino acids. In some embodiments, the protein system comprises two proteins, for example, two proteins that are bound to each other. Accordingly, in some embodiments, the protein system comprises a receptor and a ligand.

$r_1$ and $r_2$ each refer to a set of residues of the system. $r_1$ can consist of one or more residues. $r_2$ can consist of one or more residues. In exemplary embodiments, $r_1$ is one residue. In exemplary embodiments, $r_2$ is one residue. In exemplary embodiments, $r_1$ and $r_2$ comprise common elements. In some embodiments, $r_1$ and $r_2$ consist of common elements. In some embodiments, $r_1$ and $r_2$ are completely distinct. In some embodiments, $r_1$ and $r_2$ are partially distinct.

A perturbation can be any change to any property of a residue. For example, a perturbation can be a change in structure (e.g., a change in one or more dihedral angles, bond angles or bond lengths, in any combination), amino acid type (i.e., a mutation), the model used to represent a residue or the model used to represent the interaction between the residue and its environment. In some embodiments, at least one of the perturbations is selected from an alteration to the structure of one or more residues of $r_2$, an alteration of the amino acid type of one or more residues of $r_2$, an alteration to the model used to represent the one or more residues of $r_2$ and an alteration to the model used to represent the interactions between $r_1$ and $r_2$.

In exemplary embodiments, the perturbations comprise one or more mutations. In exemplary embodiments, the first set of residues is a single residue and the second set is another single residue. In these embodiments, the method can be represented by the following pseudocode:

```
def pair_coupling(system, filter_a, filter_b):
    # Filter the system to get the two residues.
    residue_a=filter_a.filter_system(system)
    residue_b=filter_b.filter_system(system)
    # Loop over valid residue-types for the two positions
    properties={ }
    for residue_type_a in all_residue_types:
        system=MutateSequence(system, residue_a, residue_type_a)
        for residue_type_b in all_residue_types:
            system=MutateSequence(system, residue_b, residue_type_b)
            # Find the optimal side-chain conformations
            system=FindOptimalConformation(system, filter_a, filter_b)
            # Compute any additional properties of the system
            properties [(residue_type_a, residue_type_b)]
                =Properties (system) return properties
```

The filters in the pseudocode represent criteria for selecting the residues of interest. In some embodiments, the design target could be to increase the binding strength between two proteins. Thus, one typical filter is to let one set of residues of a given protein be at the binding interface to some other protein. The filter to select the second set of residues could be used to select interface residues, but also to select residues one or more layers from the interface. The goal could be to find residues in the second, third or further layer that couple to the interface residues. Thus, filters could be used to expand the "space" within which the design target is optimized.

The methods comprise optimizing a quality function Q by modifying one or more properties of $r_1$ and $r_2$ in a constrained environment. In other words, one or more properties of $r_1$ and $r_2$ are varied until the value of Q reaches an optimal value. These may thus be considered optimized residues. In exemplary embodiments, the quality function comprises a free energy term, for example, a free energy of stability, a free energy of interaction or the like, as commonly understood in the art. In some embodiments, the quality function comprises one or more measures selected from a measure of protein volume, a measure of protein surface area, a measure of relative particle coordinates and atom types a measure of contact between multiple proteins or parts of a single protein, a measure of protein surface area exposed to a solvent and a measure of protein shape.

A constrained or idealized environment is one in which all degrees of freedom of the system except those directly involved in the potential coupling between $r_1$ and $r_2$ are removed. As such, in exemplary embodiments, the optimizing step excludes the modification of properties of spectator residues, that is, residues that are not involved in $r_1$-$r_2$ coupling or that are only indirectly involved in $r_1$-$r_2$ coupling. Thus, in some embodiments, a residue in close contact with $r_1$ is fixed during optimization. "In close contact" can mean, for example, having a heavy (i.e., non-hydrogen) atom less than 6 Å (or other similar distance) from $r_1$. In some embodiments, "in close contact" means having a heavy atom less than about a distance from $r_1$, wherein the distance is selected from 3.6, 3.8, 4.0, 4.2, 4.4, 4.6, 4.8, 5.0, 5.2, 5.4, 5.6, 5.8, 6.0, 6.2, 6.4, 6.6, 6.8 and 7.0 Å. In some embodiments, "in close contact" means having a heavy atom less than about 3.66 Å from $r_1$. In some embodiments, the properties of residues outside $r_1$ and $r_2$ are held constant.

In exemplary embodiments, where $r_1$ and $r_2$ represent a pair of residues, a constrained environment is selected from any of the three types of background limits given below:
  a. "Full background" wherein all other residues in the system apart from the given pair have their backbone and side-chain fixed in the conformation given by the wild-type (or other parent) structure input to the method;
  b. "Zero background" wherein all other residues in the system apart from the given pair have been mutated to ALA, which implies that the backbone and the C-beta atoms are fixed (exceptions are GLY and PRO, which are not mutated to ALA in case they are the wild-type residue for a certain position); and
  c. The full background for one molecule, such as a receptor, zero background for another molecule, such as a ligand, for example, an antibody. This calculation is referred to as the "mixed background".

Thus, in some embodiments, the full background is one in which all of residues of the protein system apart from $r_1$ and $r_2$ have their backbone and side-chain fixed. In some embodiments, In some embodiments, the zero background is one in which all residues of the protein system apart from $r_1$, $r_2$, glycine and proline are mutated to alanine. In some embodiments, the protein system comprises a receptor and a ligand, and wherein the constrained environment is a mixed background wherein the receptor provides a full background and the ligand provides a zero background. In some embodiments, all of residues of the receptor apart from $r_1$ and $r_2$ have their backbone and side-chain fixed, and all of the residues of the ligand apart from $r_1$, $r_2$, glycine, proline are mutated to alanine.

These background limits are such that the degrees of freedom of the residue in the complement to the pair (i.e., residues of the system other than the pair) are fixed and are not altered when optimizing the quality function Q. This provides the advantage of reducing the complexity of the optimization problem, thus enabling a much more comprehensive scan of double mutation combinations. It can of course be appreciated that instead of pairs, more than two residues can be optimized against a full, zero, mixed or other constrained background as described above.

A set of properties are obtained for at least one of the optimized residues. Thus, the methods comprise applying a measure M to one or more residues (e.g., optimized residues, such as those in $r_1$) to provide a property value v. Properties can be, but are not limited to, residue-type, conformation of side-chain or backbone, or another modeled physical property of the residue. This dictionary of data is then further analyzed for whatever property is of interest. In some embodiments, the measure M comprises an enumeration of the residues in $r_1$ that exhibit an altered property after application of one or more perturbations to the residues of $r_2$ and optimization of Q. In some embodiments, the measure M comprises a determination of rotamer conformation.

Analyzing the Resulting Data

The properties that are measured above can be further analyzed to determine coupling between residues. For example, the properties can be used to generate one or more coupling measures or metrics, as described below. Thus, in some embodiments, the method comprises calculating a first coupling measure $M_{c1}$ based on two or more property values selected from $V_1$. In some embodiments, calculating the first coupling measure $M_{c1}$ comprises calculating a mean, the total, an extremum or a variability measure of $V_1$. In some embodiments, the variability measure is selected from an entropy, a variance and an absolute deviation. In some embodiments, the entropy is Shannon entropy.

The methods herein can be used to determine the effect of perturbations at one protein site on another site and vice versa. Thus, in some embodiments, $r_1$ is a residue at a position $s_1$ and $r_2$ is a residue at a position $s_2$ of the protein system. In some embodiments, the method is repeated according to a second set of perturbations $P_2$, wherein $r_1$ is a residue at the position $s_2$ and $r_2$ is a residue at the position $s_1$, thereby providing values $V_2$; and the method further comprises calculating a second coupling measure $M_{c2}$ based on two or more property values selected from $V_2$. In some embodiments, the perturbations $P_2$ comprise one or more residue mutations.

In some embodiments, the method further comprises calculating a third coupling measure $M_{c3}$ based on the first coupling measure and the second coupling measure. In some embodiments, the third coupling measure is the sum of the first coupling measure and the second coupling measure. In exemplary embodiments, $V_1$, $V_2$ or both comprise property values based on rotamer conformation.

In one example, if nine positions are studied, there are 9×4=36 unique pairs of positions. For each unique pair there are 21×21=441 (for 21 possible amino acids) combinations of residue type pairs (three histidine tautomers, excluding proline). In total 15876 data points are generated along these four dimensions.

From all these data points, quantitative conclusions about the coupling between residue positions and particular types of pairs can be made. The choices depend on what properties of the coupling we are interested in. In some examples, two properties were studied, namely:
1. the degree of side-chain flexibility in a given position as a function of the residue type in another position; and
2. the extent of non-hydrogen atom clashes between a side-chain in a given position and the environment and the other residue in the pair.

Accordingly, in exemplary embodiments, the side-chain flexibility of a residue at a position of a protein system is measured. In some embodiments, the flexibility is quantified according to an entropy function. In exemplary embodiments, the entropy function is Shannon entropy. Shannon entropy is a measure of "randomness", introduced by Claude E. Shannon, "A Mathematical Theory of Communication", Bell System Technical Journal, 1948 Jul. 27: 379-423; 1948 Oct. 27: 623-656. Shannon's entropy is defined as:

$$S = \sum_k -P_k \ln(P_k)$$

where $P_k$ is the probability that the kth rotamer is observed. In the case where only one rotamer m is observed, all $P_k$ are zero, except $P_m$, which is equal to 1. This leads to S=0 and signifies the lowest possible flexibility.

The flexibility of a residue thus can be determined by calculating a measure of variability, such as an entropy, over a set of observed conformations, such as side-chain rotamers. Each possible rotamer of a residue can be assigned an index. Accordingly, in some embodiments, a rotamer index of a residue is determined. In this embodiment, the rotamer index is computed for a given residue at a given position as the residues at a different position are scanned over a set of residue types. For example, when the residues at the different position are scanned over a set of 21 residue types, a rotamer list of 21 elements can be produced for the given residue:

rot_list=[0, 4, 4, 4, 5, 0, 0, 0, 0, 0, 4, 5, 5, 5, 5, 5, 5, 5, 5, 5, 5]

in which each element in the list is a rotamer index corresponding to a specific rotamer of the given residue when the residue at a different position in the protein is one of 21 different possibilities. The rotamer list can be used to calculate flexibility as well as other properties.

For the rotamer list given above, the Shannon entropy is

S=−6/21 ln(6/21)−4/21 ln(4/21)− 11/21 ln(11/21)≈0.44

In the case where only one rotamer is different from all others, the Shannon entropy is:

S=−20/21 ln(20/21)−1/21 ln(1/21)≈0.08

In this case, with at most 21 different rotamers, the maximum entropy is obtained if the distribution is uniform:

$$S = \sum_{i=1}^{21} \frac{-1}{21} \ln\left(\frac{1}{21}\right) = \ln(21) = 3.04$$

In some embodiments, a measured residue property is a non-hydrogen or "heavy" atom clash. A heavy atom clash count is computed by counting the number of heavy atom contacts that are below 2.5 Å (or some similarly suitable number, such as 1.8, 1.9, 2.0, 2.1, 2.2, 2.3, 2.4, 2.6, 2.7, 2.8, 2.9, 3.0, 3.1, 3.2, 3.3, 3.4 or 3.5 Å) for the side-chain atoms of a given residue and all other atoms in the environment. In exemplary embodiments, counting the number of heavy atom contacts can comprise simple counting, that is, determining an integer number of heavy atoms within some distance, e.g., 2.5 Å. In some embodiments, a close contact function could be used. A large heavy atom clash count is an indication that despite the lowest energy conformation being obtained, many clashes occur. This can be a reason why a residue has a low flexibility, and not because it is weakly interacting with the other partner residue in the pair.

Coupling measures can be used to determine coupled residues. Coupling measures for different residues or sites can be combined in various ways, for example through addition, to provide additional coupling measures. Two or more residues could be considered coupled if alterations to a subset of the residues produces an alteration in a property of the rest of the residues. For example, pairs of residues or positions that have been found to strongly couple have a non-zero entropy measure. In exemplary embodiments, the larger the entropy measure, the stronger the coupling. Mutations at strongly coupled sites can be introduced into a protein system, which can then be made using art-known methods to provide engineered proteins with improved binding, stability or other such property compared to a parent system.

Applications

The methods and systems described herein have a number of useful biological applications. In particular, the methods and systems may be used to engineer any number of molecules with improved characteristics, such as improved stability, packing or binding affinity to binding partners.

Thus, in one aspect, the invention provides a method of engineering a variant of a protein, the method comprising (a) performing a method of the invention on the protein to provide one or more coupling measures; and (b) making a variant of the protein characterized by a mutation at one or more sites selected based on the one or more coupling measures. In some embodiments, the mutation is at one or more sites for which a non-zero entropy has been calculated.

A "protein" is any polypeptide, typically having a definite three-dimensional structure under physiological conditions. A "variant" protein is a protein that contains one or more mutations (e.g., insertions, deletions and substitutions) in its sequence relative to a reference "parent" protein. In exemplary embodiments, the mutation is a substitution. In exemplary embodiments, a variant protein is characterized by substituting 1%, 2%, 3%, 4%, 5%, 6%, 7%, 8%, 9%, 10%, 11%, 12%, 13%, 14%, 15%, 16%, 17%, 18%, 19% or 20% of the amino acids (or residues) of a parent protein. In some embodiments, the parent protein is a wild-type protein.

The invention also provides proteins, protein complexes and other molecules that are made according to the methods disclosed herein.

Implementation in a Computer System

The methods described may be implemented as computer programs that are executed on a computer system comprising a processor, a memory (or data storage system) and a clock. A computer program is a set of instructions that can be used, directly or indirectly, in a computer to perform a certain activity or to bring about a certain result. A computer program can be written in any form of programming language, including compiled or interpreted languages, and it can be deployed in any form, including as a stand-alone program or as a module, component, subroutine, function, procedure or other unit suitable for use in a computing environment. The methods thus are performed on a computer system programmed to perform the steps of the method.

The processor is used to control the operation of the computer system. The processor comprises one or more components. For a multi component processor, one or more components may be located remotely relative to the others, or configured as a single unit. Furthermore, a processor can be embodied in a form having more than one processing unit, such as a multi-processor configuration, and should be understood to collectively refer to such configurations as well as a single-processor-based arrangement. One or more components of the processor may be of an electronic variety defining digital circuitry, analog circuitry, or both. A processor can be of a programmable variety responsive to software instructions, a hardwired state machine, or a combination of these.

It will be appreciated by one of skill in the art that a processor comprising instructions for performing any method disclosed herein is physically distinct from a processor that does not comprise such instructions. In other words, any given processor must be physically transformed to comprise instructions for performing any method disclosed herein.

Among its many functions, the memory in conjunction with the processor is used to store data as a process is being effected. A memory can include one or more types of solid state memory, magnetic memory, or optical memory, just to name a few. By way of nonlimiting example, the memory can include solid state electronic random access memory (RAM), sequential access memory (SAM), such as first-in, first-out (FIFO) variety or last-in, first-out (LIFO) variety, programmable read only memory (PROM), electronically programmable read only memory (EPROM), or electronically erasable programmable read only memory (BEPROM); an optical disc memory (such as a DVD or CD-ROM); a magnetically encoded hard disc, floppy disc, tape, or cartridge media; or a combination of these memory types. In addition, the memory may be volatile, non-volatile, or a hybrid combination of volatile, non-volatile varieties. The memory may further include removable memory which can be in the form of a non-volatile electronic memory unit, optical memory disk (such as a DVD or CD-ROM); a magnetically encoded hard disk, floppy disk, tape, or cartridge media; or a combination of these or other removable memory types.

The processor and memory can be supplemented by or incorporated in application-specific integrated circuits (ASICs). When read into the processor of the computer, which is thus physically transformed, and executed or further processed before execution, the instructions of the program cause the programmable computer to carry out the various operations described herein. The processor and the memory are typically connected by a bus.

The clock is used to time events in the system. As should be appreciated, the clock can be incorporated into the processor or can be a stand-alone component. Further, the clock can be hardware and/or software based.

To provide for interaction with a user, the invention can be implemented on a computer system comprising a display device such as, for example, a cathode ray tube (CRT) or liquid crystal display (LCD) monitor for displaying information to the user. The user can provide input, for example, via a keyboard, a touch screen or a pointing device such as a mouse or a trackpad.

The different aspects and embodiments described herein can be implemented in a computer system that includes a backend component such as a data server, a middleware component such as an application server or an Internet server, or a front end component such as a client computer having a user interface, Internet browser or any combination thereof. The components of the system can be connected by any form or medium of digital data communication.

The present system and methods can be implemented on hardware in a variety of configurations. Thus, in some embodiments, computational processes are performed in parallel on nodes of a computer cluster, in a distributed computing system or on graphics processing units as these configurations are understood in the art.

In one aspect, the invention provides a computer system for performing any method described herein. In one embodiment, the computer system comprises a clock, a memory and a processor comprising instructions for performing any method described herein.

In one aspect, the invention provides a computer system for determining changes in a first set of residues $r_1$ due to changes in a second set of residues $r_2$ in a protein system comprising one or more proteins comprising $r_1$ and $r_2$, wherein the computer system comprises (1) a clock, (2) a memory and (3) a processor comprising instructions for performing the method, wherein the method comprises: (a) applying a perturbation selected from a first set of perturbations $P_1=\{p_1, \ldots, p_n\}$ to $r_2$, wherein n is a user-defined number of perturbations; (b) optimizing a quality function Q by modifying one or more properties of $r_1$ and $r_2$ in a constrained environment in which all degrees of freedom of the system except those directly involved in the potential coupling between $r_1$ and $r_2$ are removed; (c) applying a measure M to a subset of $r_1$ thereby providing a property value v; and (d) repeating steps (a) through (c), each time applying a different perturbation selected from the perturbations $P_1$ until all perturbations in $P_1$ have been applied, thereby providing a set of property values $V_1=\{v_1, \ldots, v_n\}$.

A computer program disclose herein can be stored on a computer-readable storage system. Examples of storage systems include, without limitation, optical disks such as CD, DVD and Blu-ray Discs (BD); magneto-optical disks; magnetic media such as magnetic tape and internal hard disks and removable disks; semi-conductor memory devices such as EPROM, EEPROM and flash memory; RAM; and other types of memory.

A computer-readable storage system may be physically transformed such that it contains a computer program. It will be appreciated by one of skill in the art that a computer-readable storage system comprising instructions for performing any method disclosed herein is physically distinct from a computer-readable storage system that does not comprise such instructions. In other words, any given computer-readable storage system must be physically transformed to comprise instructions for performing any method disclosed herein. A computer-readable storage system comprising computer executable instructions, such as instructions for performing any method disclosed herein, is physically configured so as to cause a computer interacting with the storage system to perform a process or a method. One of skill in the art will appreciate that a computer-readable storage system comprising computer executable instructions for performing any method disclosed herein, when accessed and read by a general purpose computer, will transform the general purpose computer into a special purpose computer.

Thus, in one aspect, the invention provides a computer-readable storage system comprising computer executable instructions for performing any method described herein. In one embodiment, a computer-readable storage system comprises computer executable instructions for a method of determining changes in a first set of residues $r_1$ due to changes in a second set of residues $r_2$ in a protein system comprising one or more proteins comprising $r_1$ and $r_2$, wherein the method is performed on a computer programmed to perform the steps of the method, the method comprising: (a) applying a perturbation selected from a first set of perturbations $P_1=\{p_1, \ldots p_n\}$ to $r_2$, wherein n is a user-defined number of perturbations; (b) optimizing a quality function Q by modifying one or more properties of $r_1$ and $r_2$ in a constrained environment in which all degrees of freedom of the system except those directly involved in the potential coupling between $r_1$ and $r_2$ are removed; (c) applying a measure M to a subset of $r_1$ thereby providing a property value v; and (d) repeating steps (a) through (c), each time applying a different perturbation selected from the perturbations $P_1$ until all perturbations in $P_1$ have been applied, thereby providing a set of property values $V_1 = \{v_1, \ldots, v_n\}$.

EXAMPLES

Example 1

In proof of concept studies outlined below, human IGG1 Fc fragment-Fc-gamma receptor III complex (PDB Accession Record 1E4K) was used as a representative protein system. The wild-type structure has been described in Sondermann et al., Nature, 2000, 406: 267. Pairs selected from among positions A/235, A/236, A/237, A/239, A/266, A/267, A/325, A/327, and A/328 were considered. The standard AMBER force field was used to optimize rotamer side chains in this example, where it was used in a FastPair calculation, and in the following examples, where it was used in both FastPair and traditional packing methods. For background on AMBER, see J. W. Ponder, D. A. Case "Force fields for protein simulations," Adv. Prot. Chem. 2003 Dec. 15, 66: 27-85. The values of Shannon's entropy and clash count for three different side-chain friction regimes, namely, the zero limit, mixed and infinite limit are shown in Tables 1-3 of FIG. 7. Close contacts values are provided as averages. For example, the clash count for residue position and type A/236.TYR coupling with position A/237 is reported as 14.3. This number was obtained by averaging the counts for the 21 residues at position A/237 over which the method was iterated.

Example 2

Accuracy of Rotamer Selection on a Per Site Basis

In this example, the ability of the FastPair method to correctly identify the optimal rotamer for a site/mutation combination was verified. The example considers full amino acid scans at 38 distinct site pairs of the system described in the previous example. The 38 pairs included:

B237 B328 GLY LEU
B239 B265 SER ASP
B240 B263 VAL VAL
B240 B328 VAL LEU
B240 B332 VAL ILE
B241 B262 PHE VAL
B242 B323 LEU VAL
B242 B334 LEU LYS
B262 B303 VAL VAL
B263 B302 VAL VAL
B263 B328 VAL LEU
B263 B332 VAL ILE
B266 B293 VAL GLU
B266 B323 VAL VAL
B267 B269 SER GLU
B267 B270 SER ASP
B270 B325 ASP ASN
B270 B327 ASP ALA
B274 B322 LYS LYS
B275 B304 PHE SER
B276 B278 ASN TYR
B276 B285 ASN HID
B276 B322 ASN LYS
B278 B320 TYR LYS
B278 B322 TYR LYS
B278 B333 TYR GLU

-continued

B278 B335 TYR THR
B284 B322 VAL LYS
B284 B324 VAL SER
B285 B324 HID SER
B293 B295 GLU GLN
B293 B302 GLU VAL
B295 B300 GLN TYR
B300 B302 TYR VAL
B320 B322 LYS LYS
B323 B334 VAL LYS
B325 B327 ASN ALA
B333 B335 GLU THR where, for example, "B237 B328 GLY LEU" indicates that chain B, sequence id 237 was paired with chain B, sequence id 328, and the wild-type residue type for these positions were glycine and leucine, respectively. This yielded a test set of 30324 mutations (alanine and glycine mutations were excluded from the evaluation set).

This example compares the optimal rotamer predicted by the FastPair method to the rotamer predicted by a procedure that will be referred to as traditional packing. The traditional packing operation is a high-accuracy, high cost computational approach to determining the optimal conformation of a mutated residue. Briefly, traditional packing was performed by first mutating the residue at a particular position of interest to an arginine residue (ARG). The structure of this arginine residue was then scanned through a pre-determined set of possible conformations. For each conformation of the arginine residue, all other residues possessing a heavy (non-hydrogen) atom that was less than 6 Å from a heavy atom on the arginine residue was identified. This step in the procedure is referred to as an arginine scan or ARG scan. After the arginine scan was complete, the residue at the position of interest was mutated to the desired amino acid type, and the conformation of that residue and all residues identified in the arginine scan were simultaneously optimized.

In the present context, a successful rotamer prediction for the FastPair method is defined as the selection of a rotamer for the mutated residue that has a heavy atom root-mean square deviation of less than 0.25 Å (though other thresholds could be used) relative to the rotamer predicted by traditional packing. The performance of the FastPair method is shown in Table 4, which shows fraction of successful rotamer prediction.

TABLE 4

Accuracy of the FastPair Method in Selecting Optimal Rotamers, Evaluated on a Per-Site Basis

| Residue | Total Sampled | Full Background Limit | Zero Background Limit | Mixed Background Limit | Random |
|---------|---------------|-----------------------|-----------------------|------------------------|--------|
| ARG | 1597 | 0.278 | 0.184 | 0.155 | 0.012 |
| ASN | 1596 | 0.554 | 0.305 | 0.238 | 0.056 |
| ASP | 1597 | 0.556 | 0.305 | 0.315 | 0.111 |
| CYS | 1596 | 0.716 | 0.602 | 0.531 | 0.333 |
| GLN | 1594 | 0.456 | 0.279 | 0.241 | 0.028 |
| GLU | 1595 | 0.365 | 0.197 | 0.204 | 0.037 |
| HID | 1597 | 0.630 | 0.405 | 0.385 | 0.111 |
| HIE | 1596 | 0.753 | 0.412 | 0.415 | 0.111 |
| HIP | 1596 | 0.658 | 0.404 | 0.385 | 0.111 |
| ILE | 1596 | 0.658 | 0.680 | 0.660 | 0.111 |
| LEU | 1596 | 0.710 | 0.518 | 0.486 | 0.111 |
| LYS | 1596 | 0.448 | 0.112 | 0.091 | 0.012 |
| MET | 1596 | 0.505 | 0.258 | 0.261 | 0.037 |
| PHE | 1597 | 0.655 | 0.638 | 0.647 | 0.167 |

TABLE 4-continued

Accuracy of the FastPair Method in Selecting Optimal Rotamers, Evaluated on a Per-Site Basis

| Residue | Total Sampled | Full Background Limit | Zero Background Limit | Mixed Background Limit | Random |
|---|---|---|---|---|---|
| SER | 1597 | 0.665 | 0.548 | 0.486 | 0.333 |
| THR | 1597 | 0.756 | 0.706 | 0.672 | 0.333 |
| TRP | 1596 | 0.690 | 0.522 | 0.509 | 0.111 |
| TYR | 1597 | 0.702 | 0.667 | 0.680 | 0.167 |
| VAL | 1597 | 0.712 | 0.736 | 0.706 | 0.333 |
| Average |  | 0.604 | 0.446 | 0.425 | 0.138 |

Figure 2A:
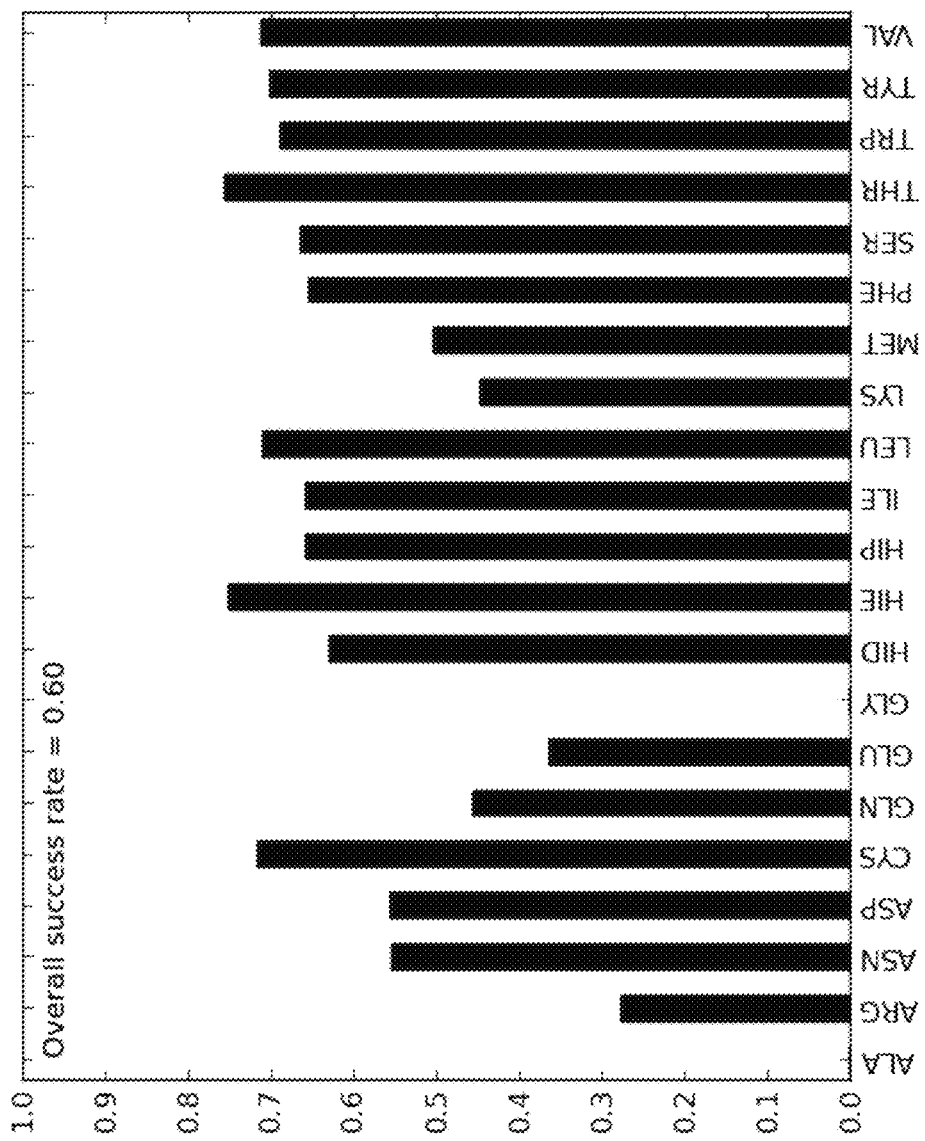
FIG. 2A-FIG. 2C shows a graphical rendition of data demonstrating the accuracy of the FastPair method in selecting optimal rotamers evaluated on a per-site basis. The y-axis is the rate of success (as described herein) in approximating traditional packing results.
Figure 2B:
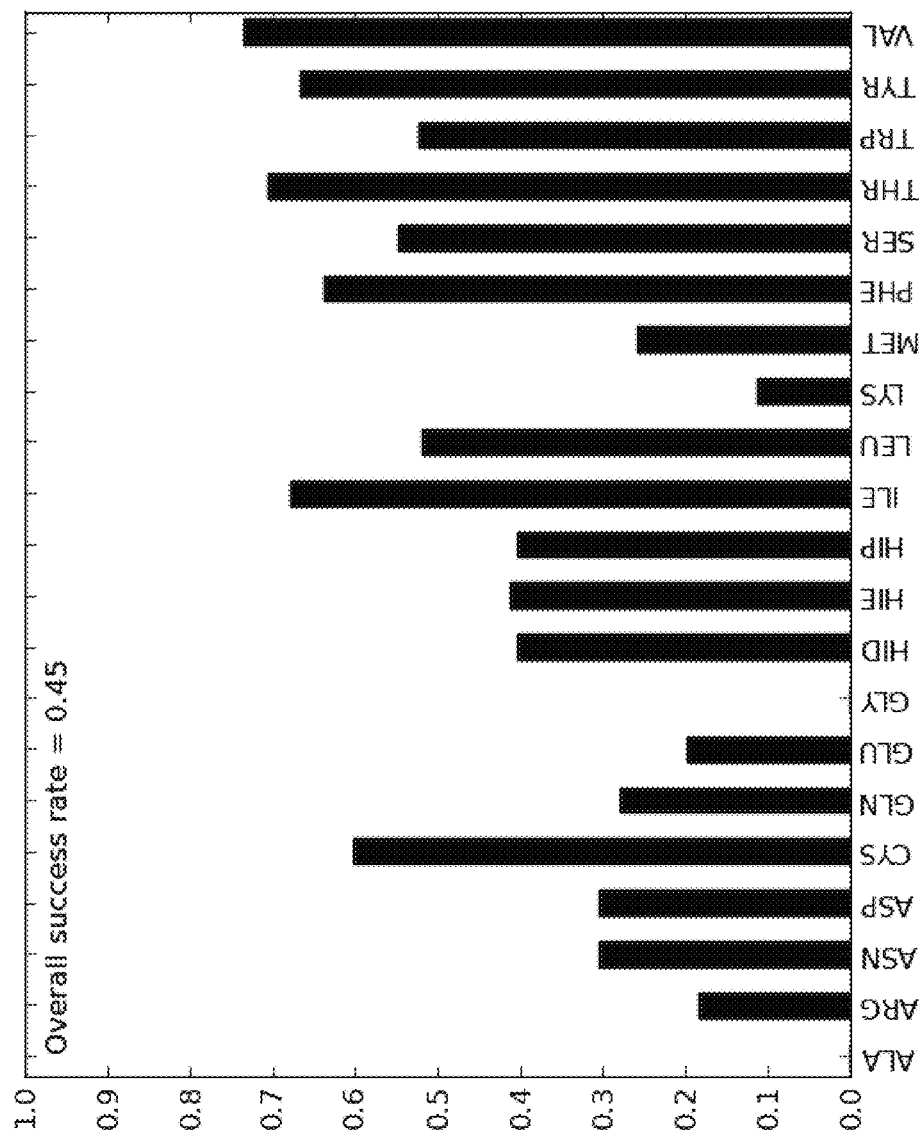
Figure 2C:
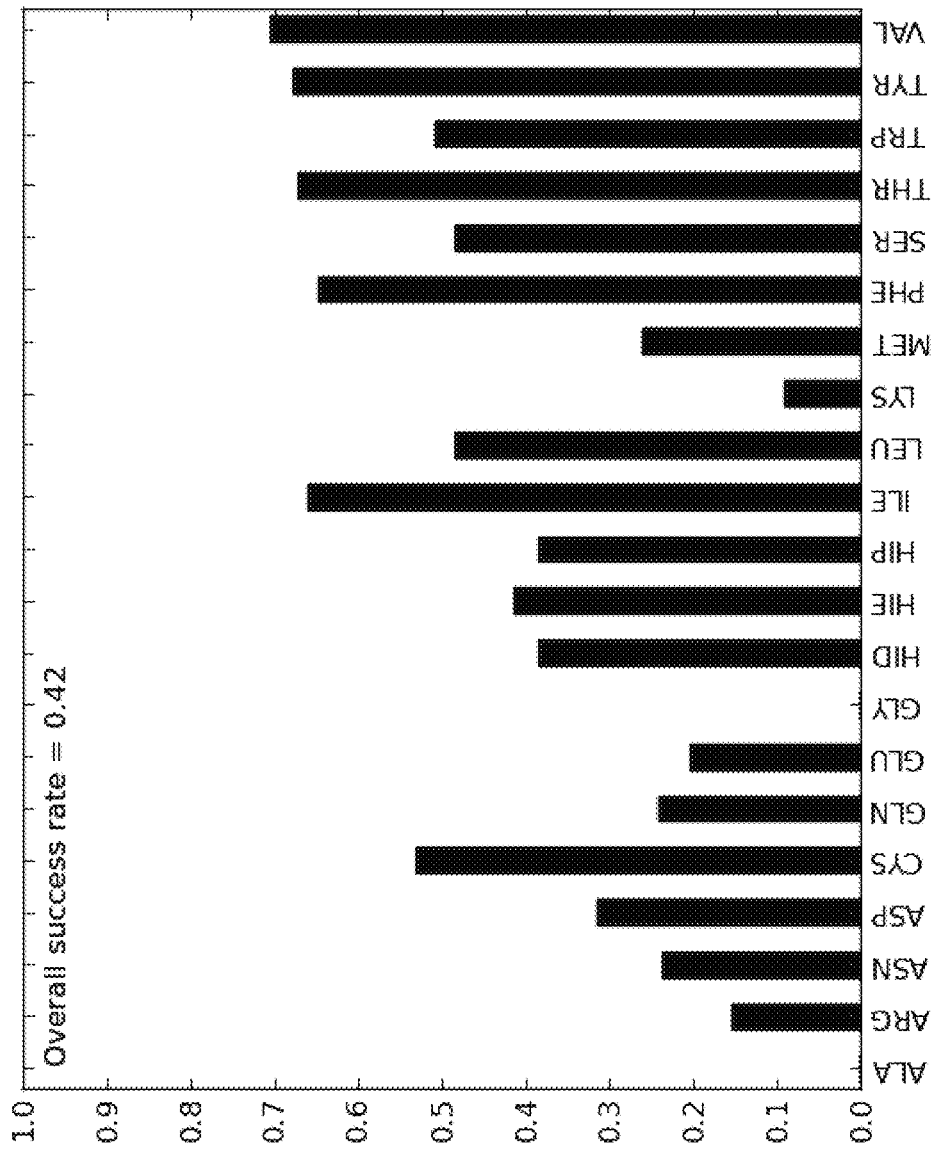

The results of Table 4 and FIG. 2 demonstrate the clear superiority of the method of the invention relative to random guessing, and clearly show the value of maintaining the full atomistic detail of the background residues when employing the method. The loss of excluded volume effects in the zero and mixed background limits is thought to have an effect on the FastPair results for residues such as charged residues, asparagine, glutamine, and methionine, which have a higher than average number of rotamers (i.e. they are relatively large, flexible, residues).

Example 3

Accuracy of Joint Rotamer Configuration

Having demonstrated the utility of the FastPair method in predicting the optimal rotamer for residues involved in pair mutations when treated individually, we now consider the method's performance in correctly predicting the joint configuration for both residues involved in a pair mutation. Specifically, in the results below, the FastPair method was deemed successful when the predicted rotamers for both residues involved in a pair mutation were simultaneously within a 0.25 Å heavy atom root-mean square deviation of the respective rotamers selected by traditional packing. Other similar thresholds may be suitable for determining successful prediction. The reference data were produced by performing traditional packing over complete residue sweeps at the 38 distinct site pairs described above, yielding a total of 13718 pair mutations (38×19×19).

In the table in FIG. 3, the accuracy of FastPair in selecting optimal rotamers is evaluated on a pair basis. The first number in each cell is the pair success rate in the full background limit, the second number is the success rate in the zero background limit, and the third is the success rate in the mixed background limit.

Figure 4A:
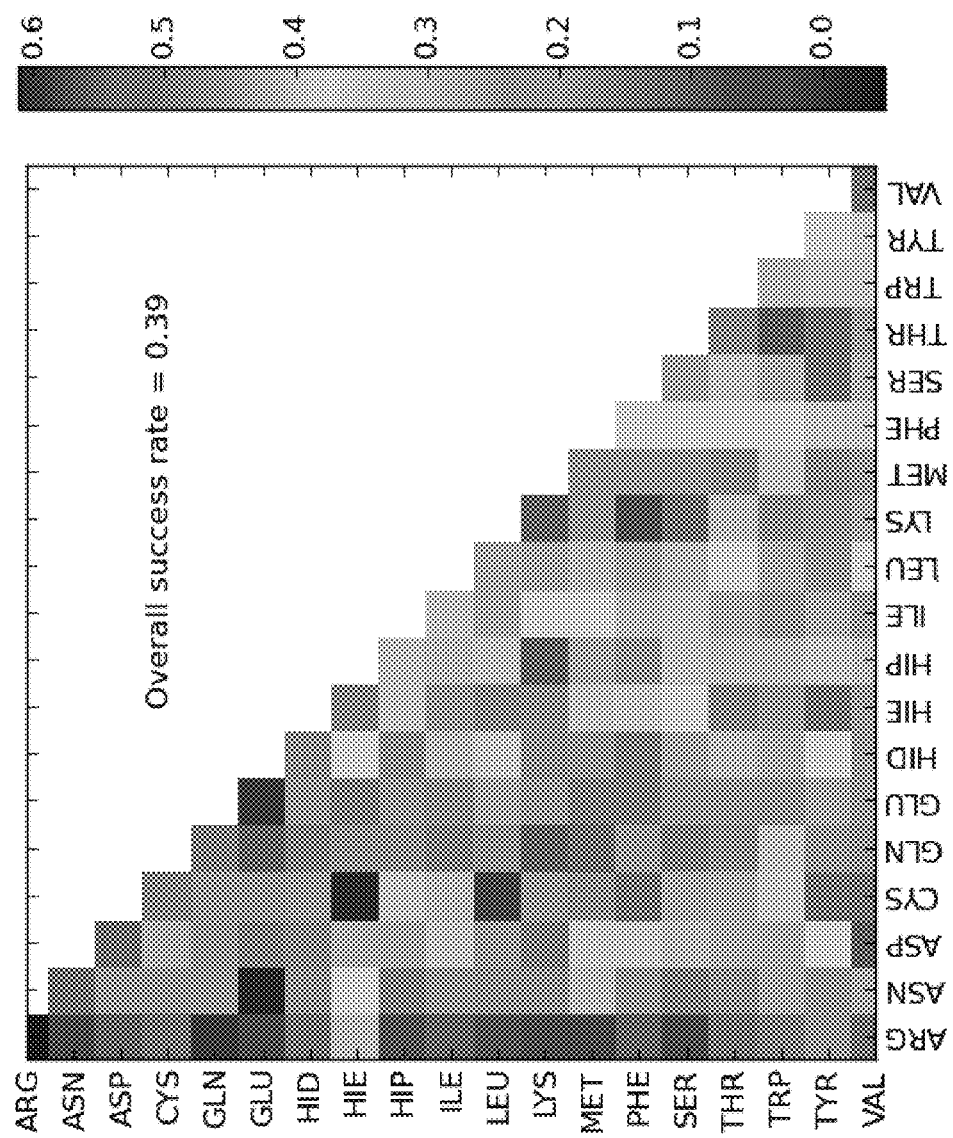
FIG. 4A-FIG. 4C shows graphical representations of success rates of three experiments (a, b, and c) with different background limits.
Figure 4B:
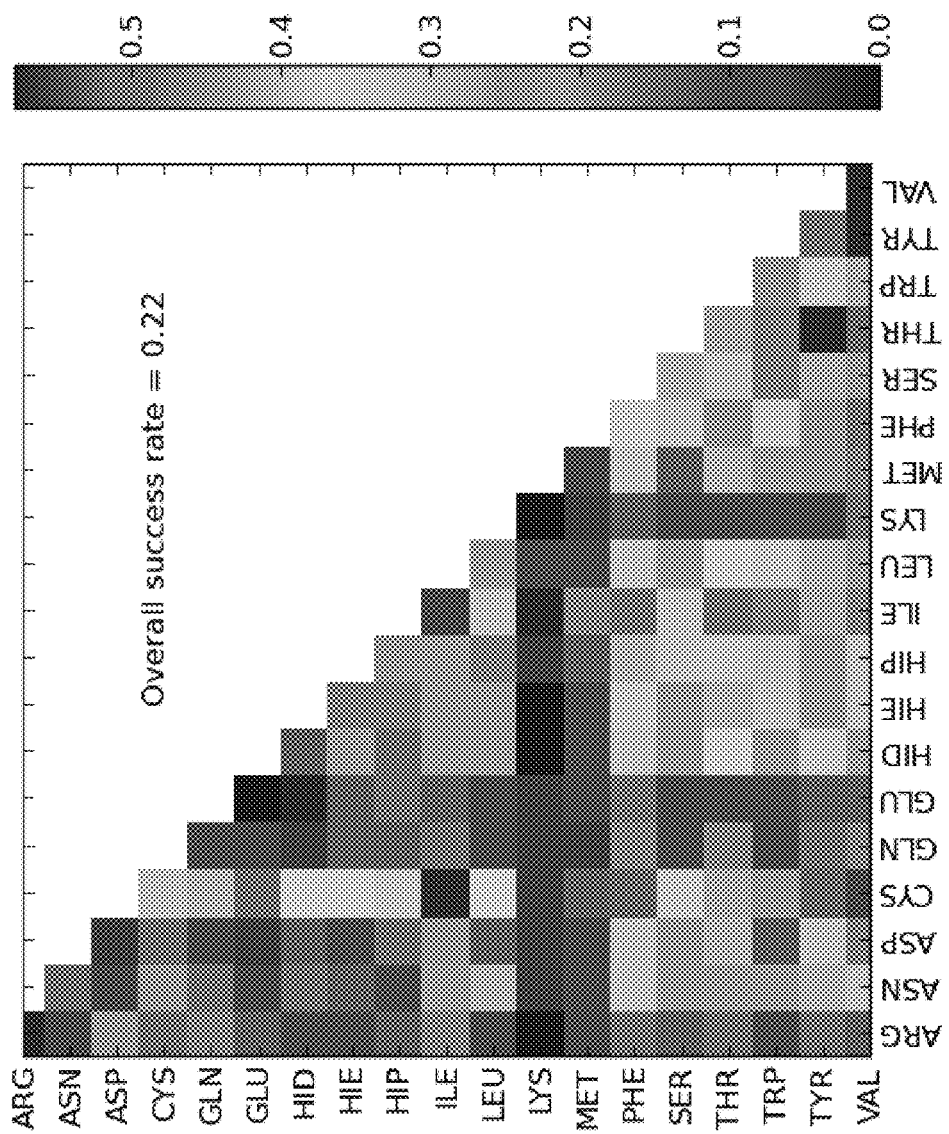
Figure 4C:
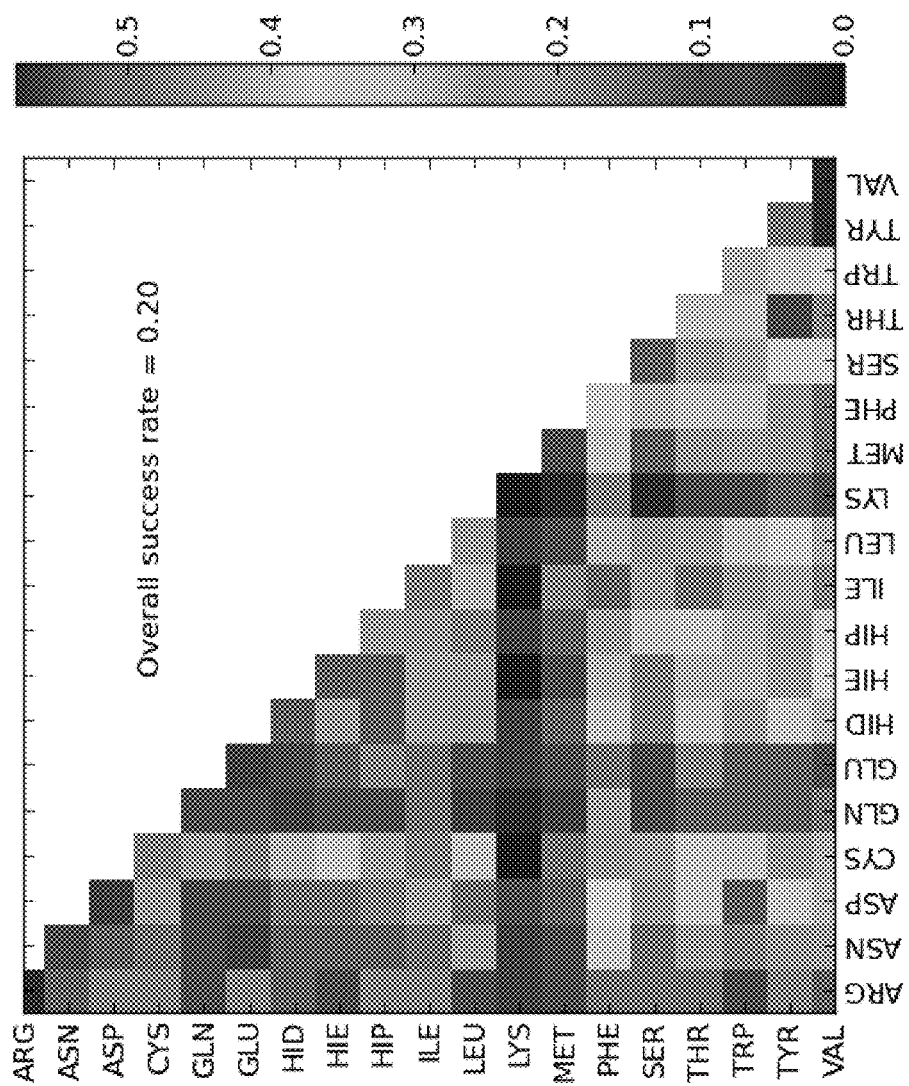

As can be seen from FIG. 4, the overall performance rate for the pair test was 0.39 in the full background limit, and 0.22 in the zero background limit, and 0.20 in the mixed background limit, compared with a random guess rate of approximately 0.02. As before, reducing the influence of excluded volume effects by using the zero background limit affects FastPair results for larger residues.

Example 4

Direct Coupling Rank Correlation

A major goal of the FastPair method is the detection of strongly interacting mutations and sites. The first test of the FastPair method's ability to identify these sites relies on computing the direct coupling energy between the targeted residues in a pair mutation. Note that as no charge screening effects are taken into consideration, interactions between charged residues are likely overestimated in these computations. Moreover, as different residue types are expected to have entirely different interaction energy scales, we make no attempt to analyze these results on a per residue-type basis. Rather, we verify that the FastPair method ranks the pair mutations on the basis of direct interaction, in a manner similar to the ranking derived from traditional packing computations. Given that both methods employ the same force field, this is a valid comparison, and effectively evaluates the similarity of the traditional packing and FastPair configurations from an energetic, rather than a geometric, perspective.

The measure of rank correlation used was the gamma correlation, defined as:

$$\Gamma = \frac{\sum_i \sum_{i>j} \Theta((H_i - H_j)(E_i - E_j))}{\sum_i \sum_{j>i} |\Theta((H_i - H_j)(E_i - E_j))|}$$

where $$\Theta(x) = \begin{cases} 1 & \text{if } x > 0 \\ -1 & \text{if } x < 0 \\ 0 & \text{otherwise} \end{cases}$$

Here, $H_i$ is the interaction energy predicted by traditional packing, and $E_i$ is the interaction energy predicted by FastPair. The reference data used in computing the rank correlation consisted of 5000 pair mutations randomly selected from the data set described in the preceding section. Given that the source data consists of results from complete scans at 38 site pairs, the randomly selected 5000 element test set is approximately uniform in terms of amino-acid swap type and swap location.

TABLE 6

FastPair/Traditional packing direct interaction rank correlations

|  | $\Gamma$ | Probability of rank agreement (excluding ties) |
|---|---|---|
| Full background | 0.69 | 0.88 |
| Mixed background | 0.59 | 0.79 |
| Zero background | 0.59 | 0.80 |

Given that a random relationship would generate a correlation of zero, the results of the above Table 6 show an extremely strong correlation between the rankings produced by the method of the invention and rankings produced by traditional packing. Continuing the trend already observed, the full background limit substantially outperforms the alternative boundary conditions. Taken together, these results suggest that any selection of mutations on the basis of the FastPair estimates of coupling energies would tend to yield a mutation set that would be extremely similar to a set derived from traditional packing. However, FastPair is roughly one order of magnitude faster than a full packing run. To be more precise, an optimization of each pair typically required 5 s with FastPair, compared to 70 s with a full packing (on average). Thus, FastPair provides comparable results to traditional, "full" packing methods but requires fewer computational resources.

Example 5

Responsiveness Rank Correlation

In addition to the direct coupling correlation described above, the correlation between the predicted rankings of pair mutations on the basis of responsiveness was also examined. In brief, the responsiveness of residue type $t_1$ located at site $l_1$ to changes in residue type at site $l_2$ can be defined as $$s(l_1, t_1, l_2) = \frac{-1}{N} \sum_{r_1} n(r_1) \ln\left(\frac{n(r_1)}{N}\right)$$

where N is the total number of mutations performed at $l_2$, and $n(r_1)$ is the number of times rotamer $r_1$ of $t_1$ was found to be the optimal rotamer at $l_1$. Statistics on s taken over the full double mutation data set are shown below:

TABLE 7

Responsiveness statistics: FastPair results for full background, mixed background, and zero background limits

| Residue | fraction with s > 0 (FastPair) | fraction with s > 0 (traditional packing] | <s> (FastPair) | <s> (traditional packing) |
|---|---|---|---|---|
| ARG | 0.632, 0.855, 0.842 | 0.908 | 0.560, 1.049, 1.075 | 1.211 |
| ASN | 0.671, 0.895, 0.921 | 0.842 | 0.593, 0.855, 0.959 | 0.917 |
| ASP | 0.605, 0.763, 0.816 | 0.829 | 0.499, 0.605, 0.644 | 0.815 |
| CYS | 0.408, 0.645, 0.605 | 0.553 | 0.289, 0.381, 0.357 | 0.416 |
| GLN | 0.658, 0.842, 0.868 | 0.882 | 0.571, 0.801, 0.871 | 1.085 |
| GLU | 0.684, 0.947, 0.947 | 0.947 | 0.630, 0.996, 1.023 | 1.255 |
| HID | 0.355, 0.579, 0.579 | 0.645 | 0.264, 0.468, 0.476 | 0.594 |
| HIE | 0.329, 0.632, 0.618 | 0.658 | 0.243, 0.511, 0.515 | 0.615 |
| HIP | 0.408, 0.566, 0.618 | 0.658 | 0.261, 0.459, 0.491 | 0.550 |
| ILE | 0.355, 0.382, 0.382 | 0.605 | 0.289, 0.281, 0.269 | 0.495 |
| LEU | 0.382, 0.355, 0.382 | 0.605 | 0.276, 0.245, 0.229 | 0.534 |
| LYS | 0.658, 0.908, 0.908 | 0.921 | 0.598, 1.093, 1.125 | 1.168 |
| MET | 0.461, 0.724, 0.789 | 0.776 | 0.385, 0.675, 0.693 | 0.917 |
| PHE | 0.276, 0.355, 0.355 | 0.553 | 0.163, 0.193, 0.185 | 0.448 |
| SER | 0.724, 0.776, 0.842 | 0.816 | 0.670, 0.851, 0.855 | 0.798 |
| THR | 0.750, 0.763, 0.829 | 0.816 | 0.613, 0.675, 0.661 | 0.774 |
| TRP | 0.316, 0.434, 0.447 | 0.658 | 0.206, 0.291, 0.294 | 0.616 |
| TYR | 0.526, 0.618, 0.605 | 0.737 | 0.415, 0.449, 0.456 | 0.639 |
| VAL | 0.303, 0.263, 0.303 | 0.539 | 0.208, 0.171, 0.179 | 0.355 |

The results in Table 7 suggest that the full background limit, where every residue has full atomistic detail but where every background atom is fixed in position, might be considered relatively constraining. While this appears to increase the likelihood of selecting the right rotamer configuration, it tends to result in a relatively smaller responsiveness.

Using the full reference data set described in the section on rotamer selection, the responsiveness rank correlations between the FastPair and the traditional packing results are shown in Table 8:

TABLE 8

FastPair/Traditional packing responsiveness rank correlations

|  | Γ | Probability of rank agreement (excluding ties) |
|---|---|---|
| Full background | 0.55 | 0.77 |
| Mixed background | 0.47 | 0.73 |
| Zero background | 0.49 | 0.74 |

While lower than the direct coupling correlation, a correlation of at least 0.47 with a match probability of 0.73 is still very significant, and again suggests that when selecting a subset of mutations on the basis of responsiveness ranking, the mutations selected by the FastPair and traditional packing approaches would be very similar, with FastPair adding a huge benefit in decreased computing demands. As previously described, this decrease is by a factor of about ten.

In addition to the rank correlation, it is worthwhile to consider the sensitivity and specificity of the FastPair method in detecting coupled residues as measured by the responsiveness criteria. In this test, any non-zero entropy is viewed as indicative of a coupling, and under this criteria, the FastPair and traditional packing coupling predictions can be compared yielding the consensus map and sensitivity/specificity data shown below.

TABLE 9

Consensus map for the prediction of coupling as measured by responsivity entropy.

|  | Traditional packing uncoupled | Traditional packing coupled |
|---|---|---|
| FastPair uncoupled (full) | 0.30 | 0.25 |
| FastPair coupled (full) | 0.03 | 0.42 |
| FastPair uncoupled (mixed) | 0.25 | 0.16 |
| FastPair coupled (mixed) | 0.09 | 0.50 |
| FastPair uncoupled (zero) | 0.25 | 0.15 |
| FastPair coupled (zero) | 0.08 | 0.52 |

These results yield sensitivities of 0.63 and specificities of 0.89 in the full background limit, 0.78 and 0.74 respectively in the mixed background limit and 0.75, and 0.75 in the zero background limit.

Example 6

Site Coupling Metrics

The responsiveness metric is most useful in those instances in which the desired mutation at one site is known and we are seeking a second mutation that couples strongly with this known residue type and site position. In common usage however, it is often the case that independent knowledge of a single mutation at a specific site is not known, and what is desired is a broad scan across positions to arrive at sites for mutation where there is a higher than average probability of coupling. To use the FastPair method to locate potentially coupled sites, we introduce a second metric, closely related to the responsiveness metric, but one that is only a function of the positions $(l_1, l_2)$. In interpreting this metric, recall that our goal is to identify coupling between sites, and that this coupling is manifest when, in a double mutation, at least one of the mutated residues assumes a conformation distinct from the one it would assume had that mutation been done in isolation (i.e., as a single site mutation). Consequently we define this site coupling metric for the pair of sites $(l_1, l_2)$ as $$c(l_1, l_2) = \frac{1}{N} \sum_n \sum_m f(t_m, t_n, r_m, r_n, w_m, w_n)$$

where N is the total number or instinct double mutations performed at $(l_i, l_j)$ excluding any mutations where either or both residues retain their wild type value, $(t_m, t_n)$ are the residue types at sites $(l_i, l_j)$ respectively, and $(r_m, r_n)$ are the rotamers selected by the FastPair method when site $l_i$ is mutated to type $t_m$, and site $l_j$ is mutated to type $t_n$. Finally, $w_m$ is the rotamer selected by the FastPair method when $l_i$ is mutated to $t_m$ but the residue at $l_j$ remains as the wild type residue. Similarly, $w_n$ is the rotamer selected by the FastPair method when $l_j$ is mutated to $t_n$, but the residue at $l_i$ is fixed at the wild type value. With these definitions, f can be defined as follows:

$$f = \begin{cases} 1 & \text{if } r_m \neq w_m \text{ or } r_n \neq w_n \\ 0 & \text{otherwise} \end{cases}$$

In other words, for each pair of sites, a complete residue scan is performed using the FastPair approach, and we compute the fraction of double mutations where the conformation of at least one mutated residue differs from the conformation it would have had in a single mutation where the second site is fixed at its wild type value, but free to relax during the optimization process. Applying this metric to the 38 site pairs described earlier, we find the score distributions pictured in FIG. 5.

Figure 5A:
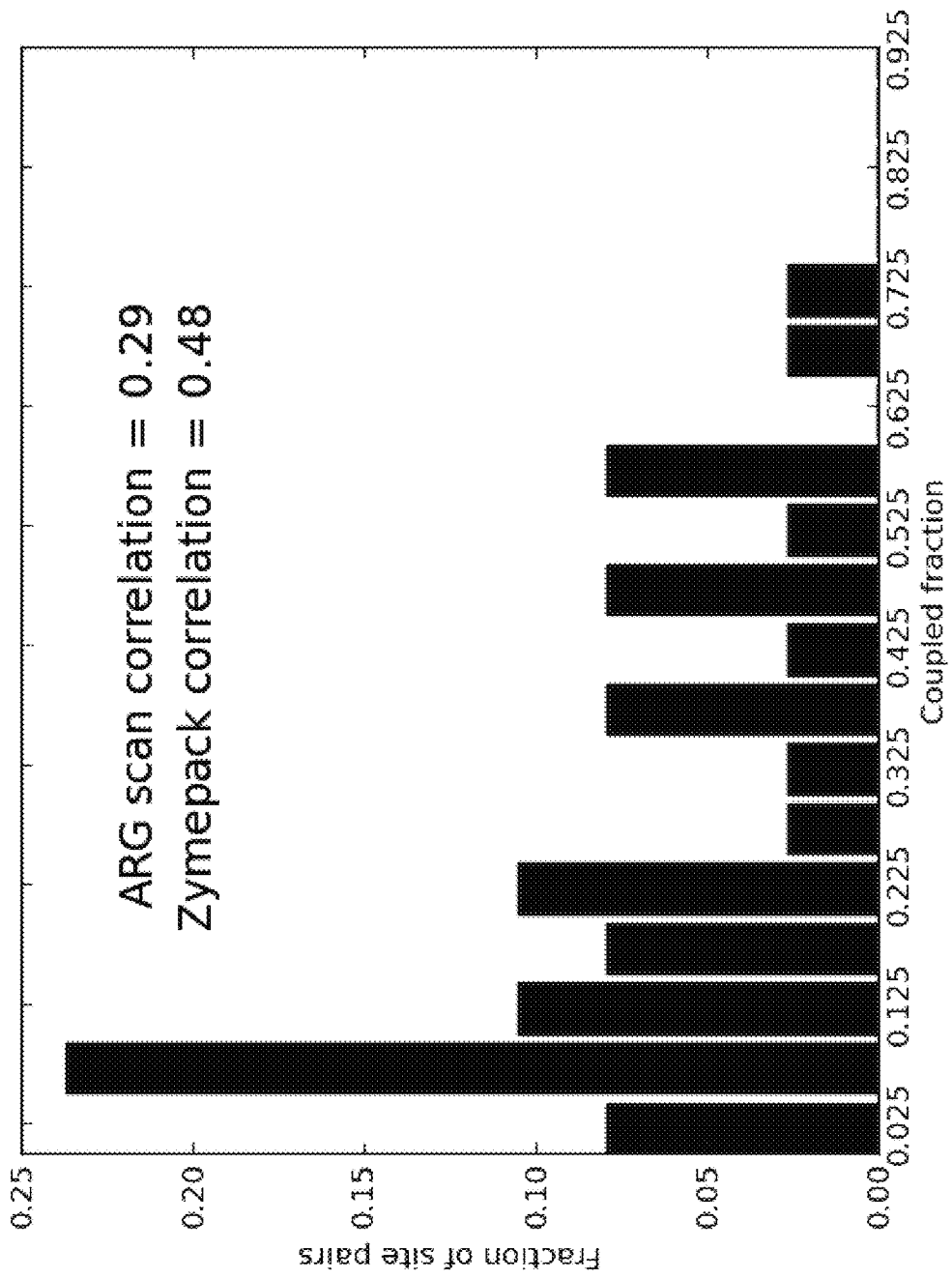
Figure 5B:
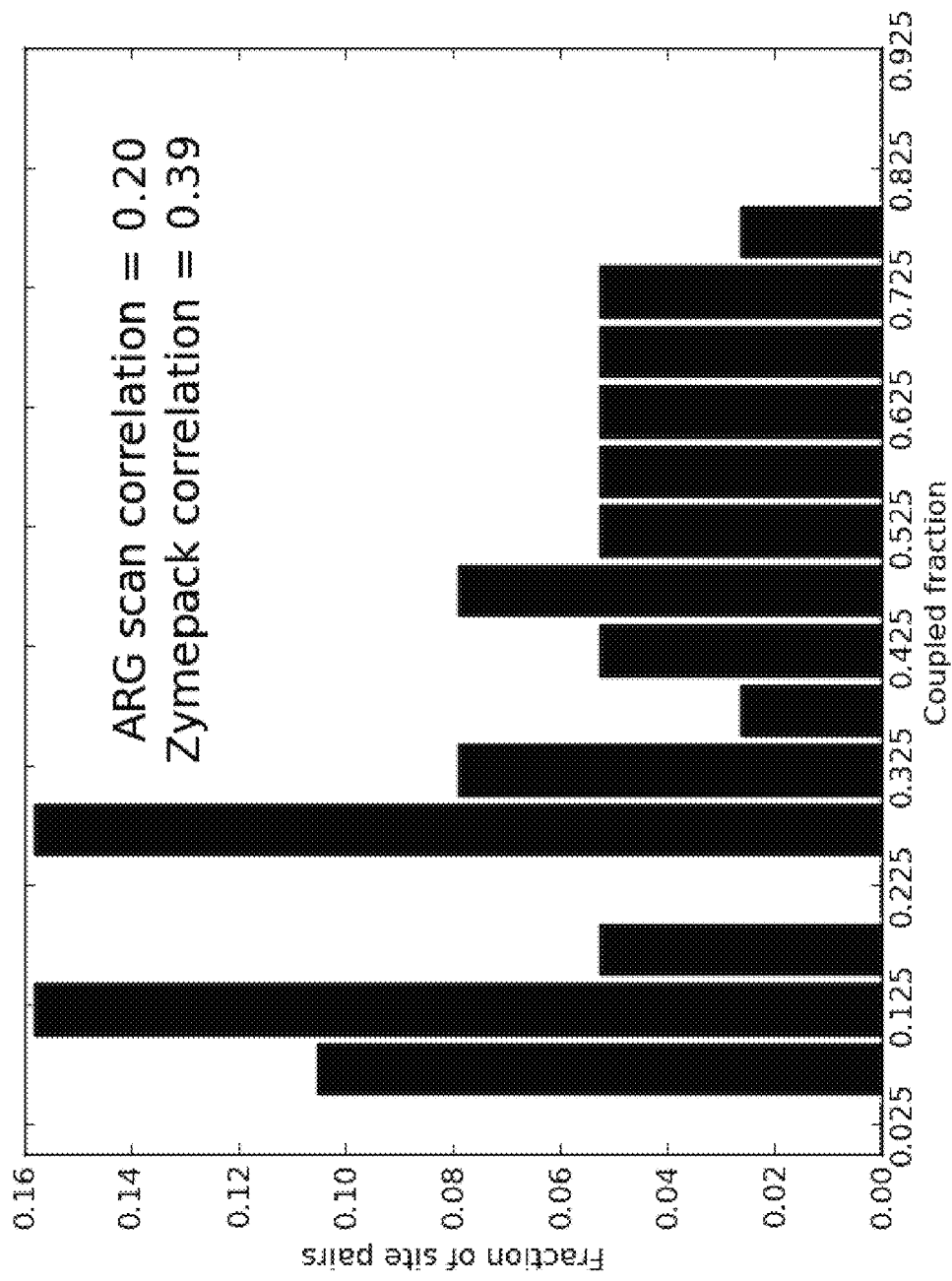

In FIG. 5, the values quoted for the ARG scan correlation refer to the rank correlation between the site coupling score for a site pair, and the overlap score for the same site pair derived from the environment overlap score based on an arginine scan performed at both sites. The environment overlap score is the ratio of number of residues common to the two lists of residues produced by arginine scans performed at each site, to the total number of residues identified by the arginine scans. The traditional packing correlation ("Zymepack correlation") displayed in FIG. 5 refers to the rank correlation between the coupling scores produced by the FastPair method, and those derived from traditional packing runs. Beyond the good correlation between the FastPair and traditional packing scores, FIG. 5 demonstrates that the coupling score is well distributed over its range, suggesting the metric has the ability to resolve sites with different degrees of coupling.

Pair Entropy

While c possesses several favorable features, including being amenable to clear and simple interpretation, it is also interesting to see if the responsiveness score s can be converted into a measure of site coupling. We will call this measure of site coupling the pair entropy $\sigma(l_i, l_j)$. Several simple approaches to construct this measure are apparent; for example, we could take the maximum or minimum of $\{s(l_i, t_i, l_j), s(l_j, t_j, l_i)\}$ over $(t_i, t_j)$. However, the simplest approach is just to average over residue types $$\sigma(l_i, l_j) = \frac{1}{2N}\left(\sum_{t_i} s(l_i, t_i, l_j) + \sum_{t_j} s(l_j, t_j, l_i)\right)$$

where N is the number of possible residue types that can be placed and any site. Applying this site entropy metric to the standard test set of 38 site pairs yields the score distributions shown below.

Figure 6A:
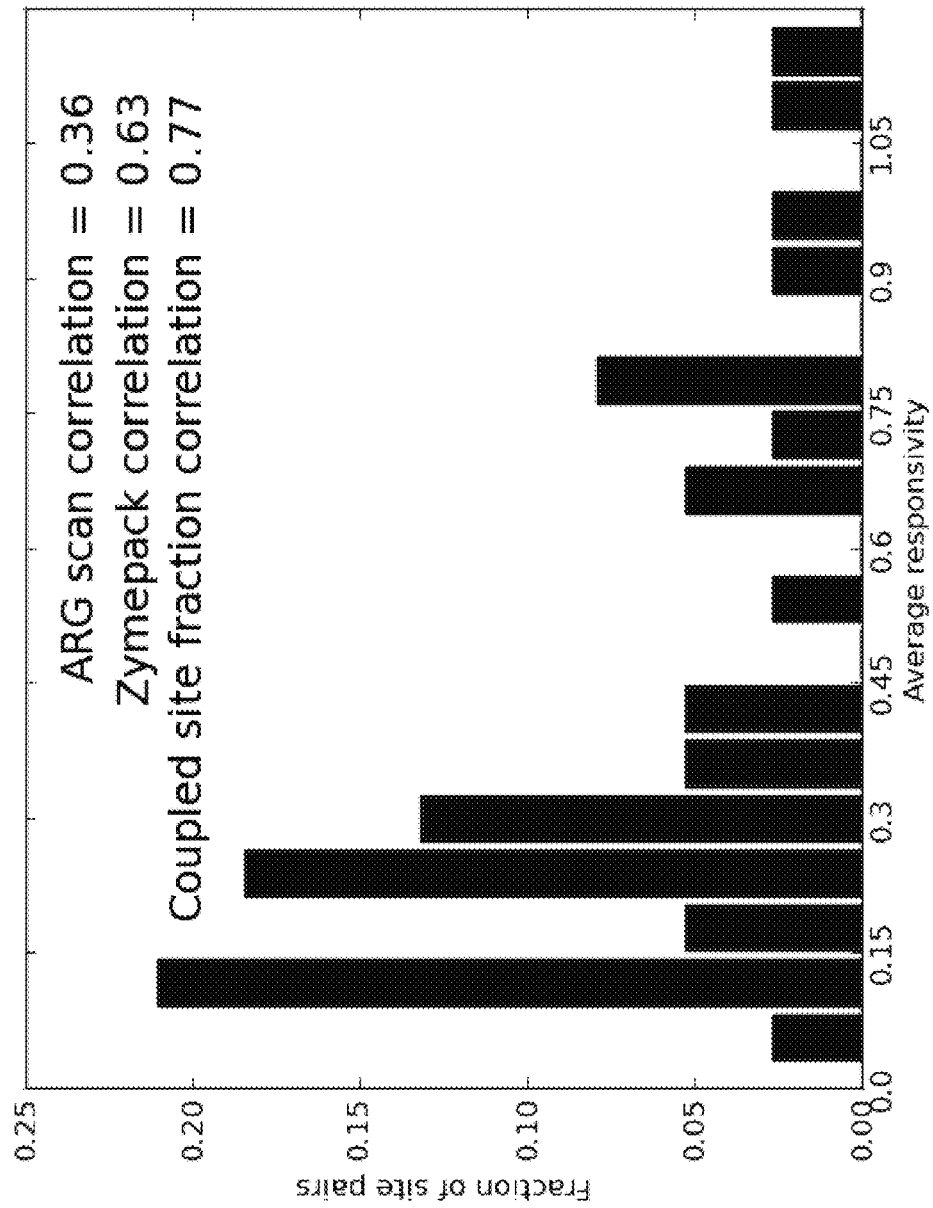
Figure 6C:
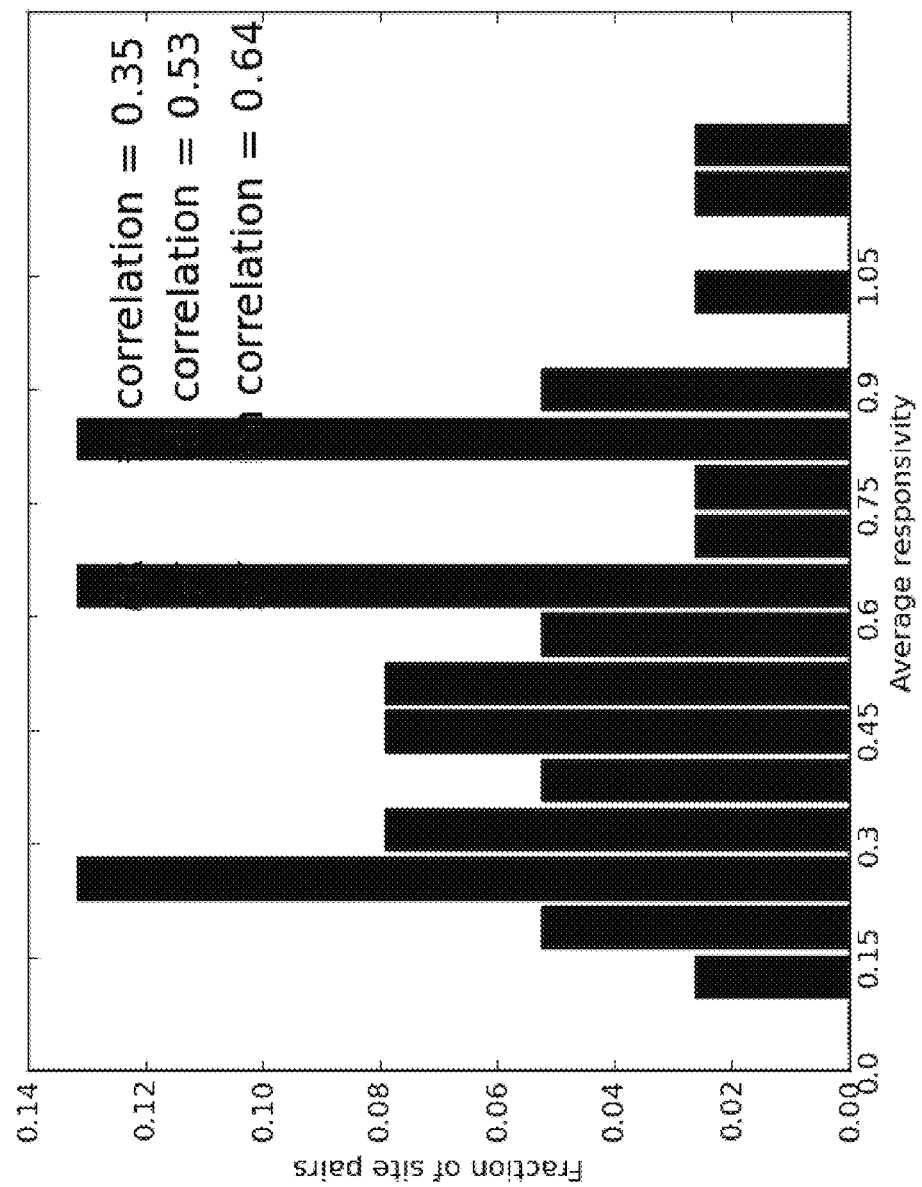

In FIG. 6, it is clear that, as was true for c, σ is also well distributed and clearly capable of differentiating between site pairs. Three comparison measures were used to investigate the behavior of σ; the ARG scan correlation is the rank correlation between σ and the environment overlap score between the residues of a pair, derived from standard arginine rotamer scans. The traditional packing correlation ("Zymepack correlation") is the rank correlation between the FastPair and traditional packing estimates for σ, and the coupled site fraction correlation is the rank correlation between the FastPair values of c and σ for the same site pairs. As can be seen from the very high values of this last metric, c and σ are apparently both capturing the same signal of coupling in the FastPair data. However, the correlation between the FastPair and traditional packing values for σ is significantly higher than the same correlation taken on c. This suggests that the FastPair approximations to the "true" (ie traditional packing derived) values of σ are more accurate than the FastPair predictions of c, and that σ could be used as the primary measure of site coupling.

Example 7

To get a sense of the performance of the FastPair method, two complete double residue scans, consisting of 800 separate double mutations were performed on the FcR system, yielding an average time per double mutation of approximately 5 s. In comparison, a full traditional packing double mutation requires approximately 70 s, suggesting that on average the FastPair method is roughly an order of magnitude faster than full traditional packing optimizations.

Given the order of magnitude increase in speed relative to traditional packing achieved by the FastPair method, the accuracy of the method is more than adequate. In particular, the method has good sensitivity and specificity measures on the determination of coupling, and rank correlations show that the FastPair and traditional packing rankings are strongly correlated. This suggests the methods described herein will be useful for isolating mutations that can subsequently be examined in more detail with full traditional packing optimizations. Even in the less critical area of rotamer prediction, the FastPair method still performs reasonably, with an average prediction accuracy of approximately 0.6 in the full background limit. Collectively, these results suggest the methods of the invention are useful replacements for traditional packing operations in a wide range of protein engineering tasks.

The articles "a," "an" and "the" as used herein do not exclude a plural number of the referent, unless context clearly dictates otherwise. The conjunction "or" is not mutually exclusive, unless context clearly dictates otherwise. The term "include" is used to refer to non-exhaustive examples.

All references, publications, patent applications, issued patents, accession records and databases cited herein, including in any appendices, are incorporated by reference in their entirety for all purposes.

We claim:

1. A computer implemented method of determining changes in a property value of a first set of residues $r_1$ due to perturbations in a second set of residues $r_2$ in a protein system comprising one or more proteins, the protein system comprising $r_1$ and $r_2$, the method comprising:
   for each respective perturbation $p_i$ in a first set of perturbations $P_1 = \{p_1, \ldots, p_n\}$, wherein n is a user-defined number of perturbations of value 2 or greater, performing the method of:
   (a) applying the respective perturbation $p_i$ to $r_2$, wherein the respective perturbation is an alteration to the structure of one or more residues of $r_2$;
   (b) optimizing, responsive to the applying (a) and using an atomistic force field for the entire protein system, a quality function Q by modifying the conformation of residues of $r_1$ and $r_2$ in a constrained environment in which the backbone of all residues in the protein system apart from the residues in $r_2$ and $r_1$ are fixed during the optimization and in which $C_\beta$ atoms of all residues, other than glycine residues and proline residues, in the protein system apart from the residues in $r_2$ and $r_1$ are fixed during the optimization and, wherein the quality function Q comprises a free energy term for $r_1$ and $r_2$; and (c) applying, upon completion of the optimizing (b), a measure M to $r_1$ thereby providing a physical property value $v_i$ of $r_1$, wherein the physical property value is a side-chain conformation value, a backbone conformation value, or a rotamer conformation value, and wherein the measure M comprises an enumeration of the residues in $r_1$ that exhibit an altered property after application of one or more perturbations to the residues of $r_2$ and optimization of Q, thereby obtaining a first set of property values $V_1=\{v_1, \ldots, v_n\}$ for $r_1$, and thereby determining changes in the property values of $r_1$ due to perturbations to $r_2$, wherein the method is performed on a computer system.

2. The method of claim 1 wherein the protein system comprises a receptor and a ligand, and wherein the constrained environment is a mixed background wherein the receptor provides a full background and the ligand provides a zero background.

3. The method of claim 2 wherein all of the residues of the receptor apart from $r_1$ and $r_2$ have their backbone and side-chain fixed, and all of the residues of the ligand apart from $r_1$, $r_2$, glycine, and proline are mutated to alanine during the optimizing (b).

4. The method of claim 1 wherein the free energy term is selected from a free energy of stability of $r_1$ and $r_2$ and a free energy of interaction of $r_1$ and $r_2$.

5. The method of claim 1 wherein the quality function comprises one or more measures selected from a measure of protein volume, a measure of protein surface area, a measure of relative particle coordinates and atom types, a measure of contact between multiple proteins or parts of a protein, a measure of protein system surface area exposed to a solvent, and a measure of protein shape.

6. The method of claim 1 wherein $r_1$ and $r_2$ comprise common elements.

7. The method of claim 1 further comprising calculating a first coupling measure $M_{c1}$ based on two or more property values selected from $V_1$, wherein the coupling measure $M_{c1}$ is a mean, a total, an extremum, an entropy, a variance, an absolute deviation, or a variability measure of $V_1$.

8. The method of claim 7 wherein $r_1$ is a residue at a position $s_1$ and $r_2$ is a residue at a position $s_2$ of the protein system in the applying (a), the optimizing (b), and the applying (c), the method further comprising, with $r_1$ being a residue at the position $s_2$ and $r_2$ being a residue at the position $s_1$, repeating the applying (a), the optimizing (b) and the applying (c) for each respective perturbation $p_i$ in a second set of perturbations $P_2$ until all perturbations in the second set of perturbations have been applied, thereby providing a second set of property values $V_2$ for $r_1$ and, calculating a second coupling measure $M_{c2}$ based on two or more property values selected from $V_2$.

9. The method of claim 8 wherein the second set of perturbations comprise one or more residue mutations.

10. The method of claim 7 further comprising:
making a variant of the protein characterized by a mutation selected based on $M_{c1}$.

11. The method of claim 1, the method further comprising evaluating the first set of property values $V_1=\{v_1, \ldots, v_n\}$ to determine a degree of side-chain flexibility in a first residue position in the protein system as a function of a residue type in a second residue position in the protein system.

12. The method of claim 1, the method further comprising evaluating the first set of property values $V_1=\{v_1, \ldots, v_n\}$ to characterize non-hydrogen atom clashes between a side-chain in a first residue position in the protein system and a residue in the second residue position in the protein system.

13. The method of claim 1, the method further comprising evaluating the first set of property values $V_1=\{v_1, \ldots, v_n\}$ to identify an optimal rotamer position for a side-chain in a first residue position in the protein system.

14. A computer readable medium comprising nontransitory instructions that perform the method of claim 1.

15. A computer system comprising a clock, a memory and a processor, the memory comprising nontransitory instructions that performs the method of claim 1.

* * * * *